United States Patent
Corum et al.

(10) Patent No.: US 10,230,270 B2
(45) Date of Patent: Mar. 12, 2019

(54) POWER INTERNAL MEDICAL DEVICES WITH GUIDED SURFACE WAVES

(71) Applicant: CPG Technologies, LLC, Red Oak, TX (US)

(72) Inventors: James F. Corum, Morgantown, WV (US); Kenneth L. Corum, Plymouth, NH (US); Paul Kendall Carlton, Jr., College Station, TX (US); Joseph F. Pinzone, Cornelius, NC (US)

(73) Assignee: CPG Technologies, LLC, Italy, TX (US)

( * ) Notice: Subject to any disclaimer, the term of this patent is extended or adjusted under 35 U.S.C. 154(b) by 42 days.

(21) Appl. No.: 15/239,507

(22) Filed: Aug. 17, 2016

(65) Prior Publication Data

US 2017/0070094 A1 Mar. 9, 2017

Related U.S. Application Data

(60) Provisional application No. 62/215,868, filed on Sep. 9, 2015.

(51) Int. Cl.
*H02J 50/10* (2016.01)
*H02J 3/16* (2006.01)
(Continued)

(52) U.S. Cl.
CPC .......... *H02J 50/10* (2016.02); *A61B 5/02055* (2013.01); *A61N 1/365* (2013.01);
(Continued)

(58) Field of Classification Search
None
See application file for complete search history.

(56) References Cited

U.S. PATENT DOCUMENTS

| 645,576 A | 3/1900 | Telsa |
| 649,621 A | 5/1900 | Tesla |

(Continued)

FOREIGN PATENT DOCUMENTS

| EP | 0639301 | 2/1995 |
| EP | 1898532 | 3/2008 |

(Continued)

OTHER PUBLICATIONS

Ling et al., The Propagation and Excitation of Surface Waves in an Absorbing Layer, Progress in Electromagnetics Research, 1998, pp. 49-91, vol. 19.

(Continued)

*Primary Examiner* — Erica S Lee
(74) *Attorney, Agent, or Firm* — Thomas | Horstemeyer, LLP

(57) ABSTRACT

Disclosed is an implantable medical device and methods of using the medical device. The medical device may include a guided surface wave receive structure configured to receive a guided surface wave transmitted by a guided surface waveguide probe. The guided surface wave receive structure in the medical device generates an alternating current signal when the guided surface wave is received. The medical device includes a power circuit that is coupled to the guided surface wave receive structure. The power circuit includes a power storage circuit to store the power signal. The medical device includes a medical circuit that comprises a stimulus circuit, a monitoring circuit, and potentially other components. The stimulus circuit provides a stimulus to a human body. The monitoring circuit measures a characteristic of the human body.

24 Claims, 25 Drawing Sheets

(51) Int. Cl.

| | | |
|---|---|---|
| *H02J 50/80* | (2016.01) | |
| *H01P 3/00* | (2006.01) | |
| *A61N 1/36* | (2006.01) | |
| *A61N 1/365* | (2006.01) | |
| *A61N 1/378* | (2006.01) | |
| *A61B 5/0205* | (2006.01) | |
| *A61N 1/372* | (2006.01) | |
| *A61B 5/024* | (2006.01) | |
| *A61B 5/021* | (2006.01) | |
| *A61B 5/08* | (2006.01) | |
| *A61B 5/04* | (2006.01) | |
| *A61B 5/11* | (2006.01) | |
| *A61B 5/053* | (2006.01) | |
| *A61B 5/145* | (2006.01) | |
| *A61N 1/39* | (2006.01) | |
| *A61N 1/362* | (2006.01) | |

(52) U.S. Cl.
 CPC ..... *A61N 1/36007* (2013.01); *A61N 1/36139* (2013.01); *A61N 1/3787* (2013.01); *A61N 1/37211* (2013.01); *H01P 3/00* (2013.01); *H02J 3/16* (2013.01); *H02J 50/80* (2016.02); *A61B 5/021* (2013.01); *A61B 5/024* (2013.01); *A61B 5/04001* (2013.01); *A61B 5/053* (2013.01); *A61B 5/0816* (2013.01); *A61B 5/1107* (2013.01); *A61B 5/14542* (2013.01); *A61B 2560/0219* (2013.01); *A61N 1/362* (2013.01); *A61N 1/39* (2013.01)

(56) References Cited

U.S. PATENT DOCUMENTS

| | | | |
|---|---|---|---|
| 685,012 A | | 10/1901 | Tesla |
| 685,953 A | | 11/1901 | Tesla |
| 685,954 A | | 11/1901 | Tesla |
| 685,955 A | | 11/1901 | Tesla |
| 685,956 A | | 11/1901 | Tesla |
| 723,188 A | | 3/1903 | Tesla |
| 725,605 A | | 4/1903 | Tesla |
| 787,412 A | | 4/1905 | Tesla |
| 851,336 A | | 4/1907 | Von Arco |
| 1,119,732 A | | 12/1914 | Tesla |
| 1,452,849 A | | 4/1923 | Round |
| 1,652,516 A | | 12/1927 | Conrad |
| 1,691,338 A | | 11/1928 | Conrad |
| 1,947,256 A | | 2/1934 | Friis |
| 2,685,068 A | | 7/1954 | Goubau |
| 2,921,277 A | | 1/1960 | Goubau |
| 3,123,767 A | | 3/1964 | Ghose |
| 3,219,954 A | | 11/1965 | Rutelli |
| 3,445,844 A | | 5/1969 | Grossi, et al. |
| 3,582,838 A | | 6/1971 | DeVries |
| 3,670,247 A | | 6/1972 | Gutton et al. |
| 3,742,509 A | | 6/1973 | De Bettencourt, et al. |
| 3,742,511 A | | 6/1973 | Smith et al. |
| 4,751,515 A | | 6/1988 | Corum |
| 4,808,950 A | | 2/1989 | Apostolos et al. |
| 5,045,825 A | | 9/1991 | McJunkin |
| 5,074,489 A | | 12/1991 | Gamzon |
| 5,155,495 A | | 10/1992 | Hately et al. |
| 5,293,308 A | | 3/1994 | Boys et al. |
| 5,301,096 A | | 3/1994 | Klontz et al. |
| 5,714,917 A | | 2/1998 | Ella |
| 5,835,067 A | | 11/1998 | Goodman |
| 5,920,261 A | | 7/1999 | Hughes |
| 6,025,813 A | | 2/2000 | Hately et al. |
| 6,075,498 A | | 6/2000 | Talwar |
| 6,100,691 A | * | 8/2000 | Yeung ............. G01R 33/34046 324/318 |
| 6,104,107 A | | 8/2000 | Avramenko et al. |
| 6,107,791 A | | 8/2000 | Lee |
| 6,486,846 B1 | | 11/2002 | Hart |
| 6,515,878 B1 | | 2/2003 | Meins et al. |
| 6,650,556 B2 | | 11/2003 | Dinh |
| 6,864,849 B2 | | 3/2005 | Hart |
| 6,956,535 B2 | | 10/2005 | Hart |
| 7,113,138 B2 | | 9/2006 | Hately |
| 7,307,589 B1 | | 12/2007 | Gregoire |
| 7,561,096 B2 | | 7/2009 | Hellsten |
| 7,741,734 B2 | | 6/2010 | Joannopoulos et al. |
| 7,775,112 B2 | | 8/2010 | Amemiya |
| 7,782,264 B1 | | 8/2010 | Vincent |
| 7,825,543 B2 | | 11/2010 | Karalis et al. |
| 7,890,053 B2 | | 2/2011 | Washiro |
| 7,894,770 B2 | | 2/2011 | Washiro |
| 8,063,717 B2 | | 11/2011 | Bradley et al. |
| 8,076,801 B2 | | 12/2011 | Karalis et al. |
| 8,084,889 B2 | | 12/2011 | Joannopoulos et al. |
| 8,097,983 B2 | | 1/2012 | Karalis et al. |
| 8,299,936 B2 | | 10/2012 | Papadopoulos |
| 8,338,991 B2 | | 12/2012 | Von Novak et al. |
| 8,350,769 B1 | | 1/2013 | Crawley |
| 8,378,524 B2 | | 2/2013 | Mita |
| 8,384,247 B2 | | 2/2013 | Yerazunis et al. |
| 8,395,282 B2 | | 3/2013 | Joannopoulos et al. |
| 8,536,738 B2 | | 9/2013 | Bella |
| 8,587,490 B2 | | 11/2013 | Niver et al. |
| 8,890,472 B2 | | 11/2014 | Mashinsky |
| 8,897,697 B1 | | 11/2014 | Bennett et al. |
| 8,941,448 B2 | | 1/2015 | Yu et al. |
| 9,030,363 B2 | | 5/2015 | Kenington et al. |
| 9,042,812 B1 | | 5/2015 | Bennett et al. |
| 9,154,966 B2 | | 10/2015 | Bennett et al. |
| 9,156,364 B2 | | 10/2015 | Miller et al. |
| 9,178,504 B2 | | 11/2015 | Komori |
| 2003/0080824 A1 | * | 5/2003 | Tanaka ............... H03H 7/38 333/33 |
| 2004/0227667 A1 | | 11/2004 | Sievenpiper |
| 2004/0263409 A1 | | 12/2004 | Hart |
| 2005/0111533 A1 | | 5/2005 | Berkman |
| 2005/0128154 A1 | | 6/2005 | Hately |
| 2006/0281423 A1 | | 12/2006 | Caimi |
| 2007/0035356 A1 | | 2/2007 | Ranta |
| 2007/0132489 A1 | | 6/2007 | Corum |
| 2008/0122449 A1 | | 5/2008 | Besser et al. |
| 2008/0140162 A1 | * | 6/2008 | Goetz ............... G06F 19/3418 607/60 |
| 2008/0273201 A1 | | 11/2008 | Brooks et al. |
| 2010/0194206 A1 | | 8/2010 | Burdo |
| 2010/0259111 A1 | | 10/2010 | Ruocco et al. |
| 2010/0260076 A1 | | 10/2010 | Corman |
| 2010/0264748 A1 | | 10/2010 | Tucker |
| 2011/0049997 A1 | | 3/2011 | Urano |
| 2011/0062916 A1 | | 3/2011 | Farahani |
| 2011/0080050 A1 | | 4/2011 | Thundat et al. |
| 2011/0133564 A1 | | 6/2011 | Teo |
| 2011/0133565 A1 | | 6/2011 | Teo et al. |
| 2011/0156494 A1 | | 6/2011 | Mashinsky |
| 2011/0160542 A1 | * | 6/2011 | Ahn ................. H02J 50/27 600/300 |
| 2011/0169336 A1 | | 7/2011 | Yerazunis |
| 2012/0119575 A1 | | 5/2012 | Kurs |
| 2012/0158091 A1 | * | 6/2012 | Tehrani ............. A61N 1/3601 607/42 |
| 2012/0169568 A1 | | 7/2012 | Oh et al. |
| 2012/0248889 A1 | | 10/2012 | Fukushi |
| 2012/0249449 A1 | | 10/2012 | Tseng |
| 2013/0029595 A1 | | 1/2013 | Widmer et al. |
| 2013/0049674 A1 | | 2/2013 | Davis |
| 2013/0064311 A1 | | 3/2013 | Turner et al. |
| 2013/0099584 A1 | | 4/2013 | Von Novak |
| 2013/0250579 A1 | * | 9/2013 | Athalye ............. F21V 21/00 362/296.05 |
| 2014/0015344 A1 | | 1/2014 | Mohamadi |
| 2014/0062813 A1 | | 3/2014 | Alrabadi |
| 2014/0104132 A1 | | 4/2014 | Bakalski et al. |
| 2014/0252865 A1 | * | 9/2014 | Corum ............... H02J 17/00 307/104 |
| 2014/0252886 A1 | | 9/2014 | Corum et al. |
| 2014/0308901 A1 | | 10/2014 | Turner et al. |
| 2014/0319922 A1 | | 10/2014 | Shinohara |

(56) References Cited

U.S. PATENT DOCUMENTS

| | | | |
|---|---|---|---|
| 2015/0042172 | A1 | 2/2015 | Howard |
| 2015/0109181 | A1 | 4/2015 | Hyde |
| 2015/0145339 | A1 | 5/2015 | Chiyo et al. |
| 2015/0196766 | A1* | 7/2015 | Rosenberg ......... A61N 1/36139 607/42 |
| 2015/0207334 | A1 | 7/2015 | Mitcheson et al. |
| 2015/0207335 | A1 | 7/2015 | Madawala |
| 2015/0280444 | A1 | 10/2015 | Smith et al. |
| 2017/0005529 | A1 | 1/2017 | Burling |
| 2017/0018852 | A1 | 1/2017 | Adriazola et al. |

FOREIGN PATENT DOCUMENTS

| | | |
|---|---|---|
| EP | 1965223 | 9/2008 |
| EP | 2221743 | 8/2010 |
| EP | 2568528 | 3/2013 |
| GB | 20981 | 11/1896 |
| GB | 24421 | 3/1898 |
| GB | 11293 | 11/1901 |
| GB | 13563 | 11/1901 |
| GB | 14579 | 4/1902 |
| GB | 8200 | 4/1906 |
| GB | 142352 | 8/1912 |
| GB | 1471860 | 4/1977 |
| GB | 2215524 | 9/1989 |
| GB | 2330695 B | 6/2002 |
| GB | 2387969 B | 11/2005 |
| JP | H06225481 | 8/1994 |
| JP | 2007244015 | 9/2007 |
| RU | 2143775 | 12/1999 |
| RU | 2161850 | 1/2001 |
| RU | 2183376 | 6/2002 |
| RU | 2255406 | 6/2005 |
| RU | 2273939 | 4/2006 |
| RU | 2310964 | 11/2007 |
| RU | 2340064 | 11/2008 |
| RU | 2341860 | 12/2008 |
| RU | 2342761 | 12/2008 |
| RU | 2366057 | 8/2009 |
| RU | 2366058 | 8/2009 |
| RU | 2409883 | 1/2011 |
| RU | 2423772 | 7/2011 |
| RU | 2459340 | 8/2012 |
| RU | 2473160 | 1/2013 |
| RU | 2474031 | 1/2013 |
| RU | 2488207 | 7/2013 |
| RU | 2488208 | 7/2013 |
| RU | 2533060 | 11/2014 |
| RU | 2544380 | 3/2015 |
| RU | 2548571 | 4/2015 |
| RU | 2554723 | 6/2015 |
| WO | 3313495 | 7/1993 |
| WO | WO9323907 | 11/1993 |
| WO | 9529516 A1 | 11/1995 |
| WO | 0191238 A1 | 11/2001 |
| WO | 2007146164 | 12/2007 |
| WO | 2009120490 | 10/2009 |
| WO | 2010020813 | 2/2010 |
| WO | 2010111541 | 9/2010 |
| WO | 2010129369 | 11/2010 |
| WO | 2011097046 | 8/2011 |
| WO | 2013093922 | 6/2013 |

OTHER PUBLICATIONS

Wise, W. Howard, Note on the Accuracy of Rolf's Graphs of Sommerfeld's Attenuation Formula, Proceedings of the Institute of Radio Engineers, Nov. 1930, pp. 1971-1972, vol. 18, No. 11.
Barlow et al., Surface Waves, The Proceedings of the Institution of Electrical Engineers, Nov. 1953, pp. 329-347, vol. 100, part iii.
Barlow et al., An Investigation of the Characteristics of Cylindrical Surface Waves, The Proceedings of the Institution of Electrical Engineers, Nov. 1953, pp. 321-328, vol. 100, Part III, No. 68.

Brown et al., The Launching of Radial Cylindrical Surface Waves by a Circumferential Slot, The Proceedings of the Institution of Electrical Engineers, Mar. 1959, pp. 123-128, vol. 106, Part B.
Burrows, Charles R., Radio Propagation Over Plane Earth-Field Strength Curves, Bell System Technical Journal, Jan. 1937, pp. 45-75, vol. 16, No. 1.
Burrows, Charles R., Addendum to: Radio Propagation Over Plane Earth-Field Strength Curves, Bell System Technical Journal, Oct. 1937, pp. 574-577, vol. 16, No. 4.
Burrows, Charles R., Existence of a Surface Wave in Radio Propagation, Nature, Aug. 15, 1936, p. 284, vol. 138, Nature Publishing Group.
Burrows, Charles R., The Surface Wave in Radio Propagation Over Plane Earth, Proceedings of the Institute of Radio Engineers, Feb. 1937, pp. 219-229, vol. 25, No. 2.
Collin, R.E., Hertzian Dipole Radiating Over a Lossy Earth or Sea: Some Early and Late 20th-Century Controversies, IEEE Antennas and Propagation Magazine, Apr. 2004, pp. 64-79, vol. 46, No. 2.
Jones, E.M.T., An Annular Corrugated-Surface Antenna, Proceedings of the I.R.E., Jun. 1952, pp. 721-725, vol. 40.
Fernando et al., An Investigation of the Properties of Radial Cylindrical Surface Waves Launched Over Flat Reactive Surfaces, The Proceedings of the Institution of Electrical Engineers, May 1956, pp. 307-318, vol. 103, Part B.
Belrose, John S., A Radioscientist's Reaction to Marconi's First Transatlantic Wireless Experiment—Revisited, Conference Digest, Jul. 2001, pp. 22-25, vol. 1, IEEE Antennas & Propagation Society International Symposium, Boston, MA, US.
Marconi, Guglielmo, Wireless Telegraphic Communication, Nobel Lecture, Dec. 11, 1909, pp. 196-222.
Morton, K.A., Propagation of Radio Waves Over a Plane Earth, Nature, Jun. 8, 1935, pp. 954-955, Nature Publishing Group.
Kukushkin, A.V., On the Existence and Physical Meaning of the Zenneck Wave, Physics—Uspekhi, 2009, pp. 755-756, vol. 52, No. 7, Uspekhi Fizicheskikh Nauk, Russian Academy of Sciences.
Michaels, Charles J., A Load-Tracking L Network, QST, Apr. 1992, p. 74, American Radio Relay League, Inc.
Feldman, C.B., The Optical Behavior of the Ground for Short Radio Waves, Proceedings of the IRE, Jun. 1933, pp. 764-801, vol. 21, No. 6.
Rolf, Bruno, Graphs to Prof. Sommerfeld's Attenuation Formula for Radio Waves, Proceedings of the Institute of Radio Engineers, Mar. 1930, pp. 391-402, vol. 18, No. 3.
Wait, James R., The Ancient and Modern History of EM Ground-Wave Propagation, IEEE Antennas and Propagation Magazine, Oct. 1998, pp. 7-24, vol. 40, No. 5.
Zucker, Francis J., Surface-Wave Antennas, Antenna Engineering Handbook, 2007, pp. 10.1-10.32, Chp. 10, McGraw-Hill.
Smith, Carl E., Short Low Loss AM Antenna, IEEE Transactions on Broadcasting, Jun. 1989, pp. 237-240, vol. 35, No. 2, IEEE.
Belrose, John S., An Electrically Small Umbrella Antenna for 160 Meters, ARRL Antenna Compendium, 2002, pp. 3-8, vol. 7.
Belrose, John S., Characteristics of the Crossed Field Antenna Obtained by Numerical and Experimental Modelling, IEEE Antennas and Propagation Society International Symposium, 2005, pp. 21-24, vol. 1B.
Belrose, John S., Radiation Characteristics of an Electrically Small MF Broadcast Antenna—by Simulation, 11th International Conference on Antennas and Propagation, Apr. 17-20, 2001, pp. 90-94, IEEE Conference Publication No. 480.
Cobos et al., A Modified Goubau-Type Antenna with Two Octaves of Impedance Bandwidth, Antennas and Propagation Society International Symposium, Jun. 2004, pp. 3051-3054, vol. 3, IEEE.
Goubau, Georg, Surface Waves and Their Application to Transmission Lines, Journal of Applied Physics, Nov. 1950, pp. 1119-1128, vol. 21.
Ravipati et al., The Goubau Multi Element Monopole Antenna—Revisited, Antennas and Propagation Society International Symposium, Jun. 2007, pp. 233-236, IEEE.
Pinzone et al., A New Low Profile Anti-Skywave Antenna for AM Broadcasting, NAB Engineering Conference Proceedings, 1988, 7-15.

(56) References Cited

OTHER PUBLICATIONS

Underhill, Mike, All sorts of small antennas—they are better than you think—heuristics shows why!, Lecture Presentation to the Adelaide Hills Amateur Radio Society, Feb. 2008, pp. 1-144.
Belrose, John S., The Crossed Field Antenna—Analyzed by Simulation and Experiment, ICAP-JINA Millennium Conference on Antennas and Propagation, Apr. 9-12, 2000, pp. 1-4, Davos, Switzerland.
Belrose, John S., The Truth and Untruth About Electrically Small Antennas, Amateur Radio Technical Session, QCWA 2004 International Convention, Oct. 15, 2004, pp. 1-8, Ottawa, ON, Canada.
Hately et al., An Operational MF Broadcast Antenna Using Poynting Vector Synthesis, IEEE ICAP Seventh International Conference 1991, Apr. 1991, pp. 645-648, Conference Publication 333, Part 2.
Kabbary et al., Phasing and Matching Units for the CFA, URSI Seventeenth National Radio Science Conference, Feb. 22-24, 2000, pp. B22.1-B22.8, Minufiya University, Egypt.
Underhill, M.J., The Estimation and Measurement of the Efficiency and Effectiveness of Small Antennas in an Environment, HF Radio 2003—Ninth International IEE Conference on HF Radio Systems and Techniques, Jun. 23-26, 2003, pp. 1-6, University of Bath, UK.
Trainotti et al., On the Crossed Field Antenna Performance, IEEE Transactions on Broadcasting, Sep. 2006, pp. 299-317, vol. 52, No. 3.
Trainotti, Valentin, Short Medium Frequency AM Antennas, IEEE Transactions on Broadcasting, Sep. 2001, pp. 263-284, vol. 47, No. 3.
Underhill, Mike, Tuneable Coupled (Multi-) Mode Small Antennas—CFA, CFL, EH etc?, Lecture Presentation at the Radio Society of Great Britain Convention, Oct. 2010, pp. 1-167.
Letter to James Corum from John Musselman regarding the Antenna Installation at Kodiak, Alaska, Jun. 2011.
Smith, Carl E., Antenna Coupling Unit Network Fig. 2.4, Installed at Radio Station KVOK, exact date unknown, installed some time around or before 1980, Kodiak, Alaska.
Rice, S.O., Series for the Wave Functions of a Radiating Dipole at the Earth's Surface, BSTJ, Jan. 1937, pp. 101-109, vol. 16, No. 1.
McDonald, Kirk T., "Crossed-Field" and "EH" Antennas Including Radiation from the Feed Lines and Reflection from the Earth's Surface, Published at http://www.physics.princeton.edu/~mcdonald/examples/crossedfield.pdf, Jul. 2006; updated Mar. 2010, pp. 1-11.
McDonald, Kirk T., "Crossed-Field" and "EH" Antennas Including Radiation from the Feed Lines and Reflection from the Earth's Surface, Published at http://www.physics.princeton.edu/~mcdonald/examples/crossedfield.pdf, Jul. 2006; updated Jun. 2008, pp. 1-18.
Belrose, John S., On the EH Antenna, antenneX Online, Apr. 2003, pp. 1-4, Issue No. 72.
Stewart, Brian G., Planning Application submitted by Isle of Man International Broadcasting plc to construct a Crossed Field Antenna at Cranstal, near Bride, Isle of Man, Department of Engineering Glasgow Caledonian University, Aug. 2000, pp. 1-19.
Hendry et al., Surface Waves for Communication Systems, 3rd SEAS DTC Technical Conference, 2008, A18, Edinburgh, Scotland.
Watson, W.H., The Physical Principles of Wave Guide Transmission and Antenna Systems, 1947, p. 25, Oxford at the Clarendon Press.
Pover et al., The Silsden Crossed Field Antenna, Extracts from the report on the performance of an elevated 8 Metre CFA constructed and tested at Silsden in West Yorkshire on Sep. 23-26, 2009.
Holland, Ralph, Egyptian Daytime Wave Pockets—Speculative Causes, antenneX Online, Apr. 2002, pp. 1-38, Issue No. 60.
Corum et al., Multiple Resonances in RF Coils and the Failure of Lumped Inductance Models, Sixth International Symposium Nikola Tesla, Oct. 18-20, 2006, Belgrade, SASA, Serbia.
Fujimoto et al., Small Antennas, Research Studies Press, 1987, p. 4.
Corum et al., Class Notes: Tesla Coils and the Failure of Lumped-Element Circuit Theory, published on the World Wide Web at http://www.teslatechnologyresearch.com/corum/, 1999.
Corum et al., RF Coils, Helical Resonators and Voltage Magnification by Coherent Spatial Modes, Microwave Review, Sep. 2001, pp. 36-45.

Burrows, Charles R., The Surface Wave in Radio Propagation, Proceedings of the Radio Club of America, Aug. 1937, pp. 15-18, vol. 14, No. 2.
Burrows, Charles R., The History of Radio Wave Propagation Up to the End of World War I, Proceedings of the IRE, May 1962, pp. 682-684, vol. 50, Issue 5.
Wolff, Edward A., Antenna Analysis, 1966, p. 33, John Wiley & Sons, Inc.
Vogler, L.E., A Note on the Attenuation Function for Propagation Over a Flat Layered Ground, IEEE Transactions on Antennas and Propagation, Mar. 1964, pp. 240-242, vol. AP-12, No. 2.
Banos, A., Dipole Radiation in the Presence of a Conducting Half-Space, 1966, pp. 148-158, Pergamon Press.
Barlow et al., Radio Surface Waves, 1962, pp. 1-5, 10-12, 29-33, Oxford University Press.
Brainerd et al., Ultra High Frequency Techniques, 1942, pp. 477-480, D. Van Nostrand Company, Inc., New York.
Bronwell et al., Theory and Application of Microwaves, 1947, pp. 384-387, 390, McGraw-Hill.
Clemmow, P.C., The Plane Wave Spectrum Representation of Electromagnetic Fields, 1966, pp. 30-31, Pergamon Press.
Collin, R.E., Field Theory of Guided Waves, 1960, pp. 453-454, McGraw-Hill.
Collin et al., Electromagnetic Fields, Antenna Theory—Part 1, 1969, p. 18, vol. 7, McGraw-Hill.
Collin, R.E., Antennas and Radiowave Propagation, 1985, pp. 377-385, McGraw-Hill.
Everitt et al., Communication Engineering, 3rd edition, 1956, p. 407, McGraw-Hill.
Felsen et al., Radiation and Scattering of Waves, 1973, pp. 506-513, 554-559, Prentice-Hall.
Friedman, B., Principles and Techniques of Applied Mathematics, 1956, pp. 213-214, 283-286, 290, 298-300, Wiley.
Hansen, R.C., Electrically Small, Superdirective, and Superconducting Antennas, 2006, pp. 62-64, Wiley Interscience.
Hansen et al., Small Antenna Handbook, 2011, pp. 147-150, Wiley, New Jersey.
Harrington, R.F., Time-Harmonic Electromagnetic Fields, 1961, pp. 460-463, McGraw-Hill.
Ishimaru, A., Electromagnetic Wave Propagation, Radiation and Scattering, 1991, pp. 456-461, Prentice-Hall, New Jersey.
Wise, W.H., The Grounded Condenser Antenna Radiation Formula, Proc. IRE, Sep. 1931, pp. 1684-1689, vol. 19, No. 9.
Kraus, J.D., Antennas, 1950, pp. 33-34, 452-453, 461-463, McGraw-Hill.
Wise, W.H., Asymptotic Dipole Radiation Formulas, Bell System Technical Journal, Oct. 1929, pp. 662-671, vol. 8.
Ramo et al., Fields and Waves in Communication Electronics, 3rd Edition, 1994, pp. 435-437, Wiley.
Ryder, J.D., Networks, Lines and Fields, 1949, pp. 422-425, Prentice Hall, New York.
Reich et al., Microwave Theory and Techniques, 1953, pp. 291-293, Van Nostrand.
Sarbacher et al., Hyper and Ultrahigh Frequency Engineering, 1943, pp. 201-202, Wiley & Sons, Inc.
Schelkunoff, S.A., Electromagnetic Waves, 1943, pp. 49, 428-437, Van Nostrand Company, New York.
Tesla, N., The Problem of Increasing Human Energy with Special References to the Harnessing of the Sun's Energy, The Century Illustrated Monthly Magazine, Jun. 1900, pp. 1-35.
Van Der Pol, B., On Discontinuous Electromagnetic Waves and the Occurrence of a Surface Wave, IEEE Transactions on Antennas and Propagation, Jul. 1956, pp. 288-293, vol. AP-4.
Eckert, Robert P., Modern Methods for Calculating Ground-Wave Field Strength Over a Smooth Spherical Earth, Report to the Federal Communications Division, Feb. 1986.
Wait et al., Radiation from a Vertical Dipole over a Stratified Ground (Part II), IRE Transactions on Antennas and Propagation, Oct. 1954, pp. 144-146, vol. AP-3, No. 4.
Tesla, N., From Colorado Springs to Long Island, Nikola Tesla Museum, 2008, pp. 485, 487, Nikola Tesla Museum.

(56) References Cited

OTHER PUBLICATIONS

Cross et al., An Advanced VHF/UHF Short Range, Groundwave Propagation Model for Paths with Near-Earth Antennas, MegaWave Corporation, Nov. 1, 2006, Boylston, MA.
Tyras, G., Radiation and Propagation of Electromagnetic Waves, 1969, pp. 33-36, Academic Press.
Wait, J.R., Wave Propagation Theory, 1981, pp. 67-75, 117-127, Pergamon Press.
Wait, J.R., Electromagnetic Wave Theory, 1985, pp. 254-259, Harper and Row, Publishers, New York.
Wait, J.R., Electromagnetic Waves in Stratified Media, 1996, pp. 8-10, IEEE Press, Reprint from 1962 edition, Pergamon Press.
Hessel, A., General Characteristics of Traveling-Wave Antennas, Antenna Theory—Part 2, Chapter 19, Appendix B, 1969, pp. 238-241, McGraw-Hill Book Company, New York.
Sarkar et al., Electromagnetic Macro Modeling of Propagation in Mobile Wireless Communication: Theory and Experiment, IEEE Antennas and Propagation Magazine, Dec. 2012, pp. 17-43, vol. 54, No. 6.
Wait, J.R., Characteristics of Antennas over Lossy Earth, Antenna Theory—Part 2, Chapter 23, 1969, pp. 386-391, McGraw-Hill Book Company, New York.
Wait, J.R., Theory of Ground Wave Propagation, Electromagnetic Probing in Geophysics, Chapter 5, 1971, pp. 163-172, 204-207, Golem Press, Boulder, Colorado.
Smith, M.S., Conventional Explanation for Crossed-Field Antenna, Electronics Letters, Feb. 13, 1992, pp. 360-361, vol. 28, No. 4.
Tesla, N., The Transmission of Electrical Energy Without Wires as a Means of Furthering Peace, Electrical World and Engineer, Jan. 7, 1905, pp. 21-24.
Wait et al., Excitation of the HF Surface Wave by Vertical and Horizontal Antennas, Radio Science, Sep.-Oct. 1979, pp. 767-780, vol. 14, No. 5.
Wait, J.R., A Note on Surface Waves and Ground Waves, IEEE Transactions on Antennas and Propagation, Nov. 1965, pp. 996-997, vol. AP-13.
Nikola Tesla, Nikola Tesla on His Work With Alternating Currents and Their Application to Wireless Telegraphy, Telephony, and Transmission of Power, 2002, pp. 1-240, Twenty First Century Books, Breckenridge, Colorado.
Tesla, N., Colorado Springs Notes: 1899-1900, 1978, pp. 1-437, Nolit, Beograd, Yugoslavia.
Jahnke et al., Tables of Functions with Formulae and Curves, 1945, p. 145, 4th Edition, Dover Publications, New York.
Milligan, T., Modem Antenna Design, 1985, pp. 8-9, 1st Edition, McGraw-Hill, New York.
Reinartz, J. L., 1XAM's transmitter, QST, Jan. 1924, pp. 26-27.
Sommerfeld, A., Problems of Radio, Partial Differential Equations in Physics —Lectures on Theoretical Physics, 1949, pp. 246-257, vol. VI, Academic Press, New York.
Stratton, J. A., Electromagnetic Theory, 1941, p. 516, McGraw-Hill, New York.
Stutzman et al., Antenna Theory and Design, 1981, p. 82, 92-93, Wiley & Sons, New York.
Wait, J. R., Complex Image Theory—Revisited, IEEE Antennas and Propagation Magazine, Aug. 1991, pp. 27-29, vol. 33, No. 4.
Counterpoises, QST, Sep. 1920, pp. 24-25.
Ashe, G. B., A Counterpoise Investigation, QST, Dec. 1924, pp. 34-35.
Bannister, P. R., Summary of Image Theory Expressions for the Quasi-Static Fields of Antennas at or Above the Earth's Surface, Jul. 1979, pp. 1001-1008, vol. 67, No. 7, Proceedings of the IEEE.
Banos et al., Sommerfeld Surface Wave, Summary of Normal Mode Theory Symposium, IRE Transactions on Antennas and Propagation, Jan. 1956, p. 92, vol. AP-4, No. 1.
Barlow, H. M., Launching a Surface Wave over the Earth, Electronics Letters, Jul. 1967, pp. 304-305, vol. 3, No. 7.
Westman, H. P., Antenna—Counterpoise Fundamentals, QST, May 1926, p. 46.
Beverage, H.H., Improving the CW Ground System, OST, Nov. 1921, pp. 25-26.
Bucher, E. E., The Alexanderson System for Radio Communication, General Electric Review, Oct. 1920, pp. 813-839 (See Fig. 11, p. 820.) vol. 23, No. 10.
Paknys, R., Evaluation of Hankel Functions with Complex Argument and Complex Order, IEEE Transactions on Antennas and Propagation, May 1992, pp. 569-578, vol. 40, No. 5.
Burrows, C. R., Radio Propagation Over Spherical Earth, Proc. IRE, May 1935, pp. 470-480, vol. 23, No. 5; Reprinted in Bell System Tech. Jour., Jul. 1935, pp. 477-488, vol. 14, No. 3.
Wise, W. H., The Physical Reality of Zenneck's Surface Wave, Bell System Technical Journal, No. 1, Jan. 1937, pp. 35-44, vol. 16, No. 1.
Burrows, C. R., Addendum to the Effect of the Earth's Curvature on Ground Wave Propagation, IEEE Transactions on Antennas and Propagation, Nov. 1964, pp. 789-791, vol. 12, No. 6.
Burrows, C. R., Radio Gain, IEEE Transactions on Antennas and Propagation, May 1967, pp. 404-410, vol. AP-15, No. 3.
Chu et al., Electromagnetic Waves in Hollow Metal Tubes of Rectangular Cross Section, Proceedings of the IRE, Dec. 1938, pp. 1520-1555, vol. 26, No. 12.
Ufimtsev et al., Transformation of Surface Waves in Homogeneous Absorbing Layers, IEEE Transactions on Antennas and Propagation, Feb. 2000, pp. 214-222, vol. 48, No. 2.
Corum et al., Toroidal Helix Antenna, IEEE Antennas and Propagation Society International Symposium, Jun. 14-19, 1987, pp. 832-835, vol. 25.
Pinzone et al., A Novel Structure for Improved Directivity, 1988 Antennas and Propagation Society International Symposium Digest, Jun. 1988, pp. 824-827, vol. 2, IEEE, Syracuse, NY.
Corum et al., Experimental Validation of the Improved Directivity Element—Elevation Plane Control, 1989 Antennas and Propagation Society International Symposium Digest, Jun. 1989, pp. 702-705, vol. 2, IEEE, San Jose, CA.
Corum et al., A Concentric Array for Low and Medium Frequencies, 1990 Antennas and Propagation Society International Symposium Digest, May 1990, pp. 832-835, vol. 2, IEEE, Dallas, Texas.
Deminco, N., Propagation Prediction Techniques and Antenna Modeling (150 to 1750 kHz) for Intelligent Transportation Systems (ITS) Broadcast Applications, IEEE Antennas and Propagation Magazine, Aug. 2000, pp. 9-34, vol. 42, No. 4.
Eckert, R. P., History of Ground Wave Propagation Prediction Curves for AM Standard Broadcast, IEEE Transactions on Broadcasting, Mar. 1986, pp. 1-4, vol. BC-32, No. 1.
Epstein, P., Radio-Wave Propagation and Electromagnetic Surface Waves, Proc. National Academy of Sciences, Jun. 1947, pp. 195-199, vol. 33, No. 6.
Epstein, P., On the Possibility of Electromagnetic Surface Waves, Proc. National Academy of Sciences, Dec. 1954, pp. 1158-1165, vol. 40, No. 12.
Norton, K. A., The Physical Reality of Space and Surface Waves in the Radiation Field of Radio Antennas, Proceedings of the IRE, Sep. 1937, pp. 1192-1202, vol. 25, No. 9.
Goubau, G., Single Conductor Surface Wave Transmission Lines, Proc. IRE, Jun. 1951, pp. 619-624, vol. 39, No. 6.
Norton, K.A., The Propagation of Radio Waves over the Surface of the Earth and in the Upper Atmosphere: Part II The Propagation from Vertical, Horizontal, and Loop Antennas Over a Plane Earth of Finite Conductivity, Proceedings of the IRE, Sep. 1937, pp. 1203-1236, vol. 25, No. 9.
Hately et al., CFA: Working Assumption, Electronics World + Wireless World, Dec. 1990, pp. 1094-1099, vol. 96.
Hill et al., Excitation of the Zenneck Surface Wave by a Vertical Aperture, Radio Science, Nov.-Dec. 1978, pp. 969-977, vol. 13, No. 6.
Kabbary et al., Maxwell's Equations and the Crossed-Field Antenna, Electronics World + Wireless World, Mar. 1989, pp. 216-218, vol. 95.
Trainotti et al., Short Low and Medium Frequency Antenna Performance, IEEE Antennas and Propagation Magazine, Oct. 2005, pp. 66-90, vol. 47, No. 5.

(56) References Cited

OTHER PUBLICATIONS

Kabbary et al., Four Egyptian MW Broadcast Crossed-Field Antennas, Proceedings of the National Association of Broadcasters 1999 Engineering Conference, Apr. 1999, pp. 235-241, Las Vegas, Nevada.

Kahan et al., On the Existence of a Surface Wave in Dipole Radiation over a Plane Earth, Proc. IRE, Jul. 1950, pp. 807-812, vol. 38, No. 7.

Karbowiak, A. E., Theory of Composite Guides: Stratified Guides for Surface Waves, Proc. IEE (British), 1954, pp. 238-242, vol. 101, No. 72.

Tesla, N., The True Wireless, Electrical Experimenter, May 1919, pp. 1-13.

King et al., Groundwave Attenuation Function for Propagation Over a Highly Inductive Earth, Radio Science, Jul. 1967, pp. 687-693, vol. 2, No. 7.

Li, R., The Accuracy of Norton's Empirical Approximations for Ground Wave Attenuation, IEEE Trans. Antennas and Propagation, Jul. 1983, pp. 624-628, vol. AP-31, No. 4.

Lindell et al., Exact Image Theory for the Sommerfeld Half-Space Problem, Part I: Vertical Magnetic Dipole, IEEE Transactions on Antennas and Propagation, Feb. 1984, pp. 126-133, vol. AP-32, No. 2.

Lindell et al., Exact Image Theory for the Sommerfeld Half-Space Problem, Part II: Vertical Electric Dipole, IEEE Transactions on Antennas and Propagation, Aug. 1984, pp. 841-847, vol. AP-32, No. 8.

Lindell et al., Exact Image Theory for the Sommerfeld Half-Space Problem, Part III: General Formulation, IEEE Transactions on Antennas and Propagation, Oct. 1984, pp. 1027-1032, vol. AP-32, No. 10.

Lodge et al., Syntonic Wireless Telegraphy; with Specimens of Large-scale Measurements, Proceedings of the Royal Society—London, Series A, May 26, 1909, pp. 227-256, vol. 82, No. 554.

Marincic, A. S., Nikola Tesla and the Wireless Transmission of Energy, IEEE Transactions on Power Apparatus and Systems, Oct. 1982, pp. 4064-4068, vol. PAS-101, No. 10.

Mason, H. F., The Nodal Point Explained, QST, Sep. 1923, pp. 11-14.

Norton, K. A., The Calculation of Ground-Wave Field Intensity Over a Finitely Conducting Spherical Earth, Proceedings of the IRE, Dec. 1941, pp. 623-639, vol. 29, No. 12.

Niessen, K.F., Zur Entscheidung zwischen den beiden Sommerfeldschen Formeln für die Fortpflanzung von drahtlosen Wellen, Ann. der Physik, 1937, pp. 585-596, vol. 29 (Includes English Translation and German Original).

Niessen, K.F., Über die entfernten Raumwellen eines vertikalen Dipolsenders oberhalb einer ebenen Erde von beliebiger Dielektrizitätskonstante und beliebiger Leitfähigkeit, Ann. der Physik, Dec. 24, 1933, pp. 893-912, Series 5, vol. 18 (Includes English Translation and German Original).

Niessen, K.F., Bemerkung zu einer Arbeit von Murray und einer Arbeit von van der Pol und Niessen über die Ausbreitung elektromagnetischer Wellen, Ann. der Physik, Apr. 3, 1933, pp. 810-820, Series 5, vol. 16 (Includes English Translation and German Original).

Hack, F., Die Ausbreitung ebener elektromagnetischer Wellen längs eines geschichteten Leiters, besonders in den Fällen der drahtlosen Telegraphie, Annalen der Physik, 1908, pp. 43-63, vol. 27 (Includes English Translation and German Original).

True, H., Über die Erdströme in der Nähe einer Sendeantenne für drahtlose Telegraphie, Jahrbuch der drahtlosen Telegraphie und Telephonie, Feb. 1911, pp. 125-175, vol. 5, No. 2 (Includes English Translation and German Original).

Van Der Pol et al., Über die Ausbreitung elektromagnetischer Wellen über eine ebene Erde, Ann. der Physik, Aug. 22, 1930, pp. 273-294, Ser. 5, vol. 6 (Includes English Translation and German Original).

Van Der Pol, B., Über die Ausbreitung elektromagnetischer Wellen, Jahrbuch der drahtlosen Telegraphie und Telephonie, Apr. 1931, pp. 152-156, vol. 37 (Includes English Translation and German Original).

Zenneck, J., "Über die Fortpflanzung ebener elektromagnetischer Wellen längs einer ebenen Leiterfläche und ihre Beziehung zur drahtlosen Telegraphie," (On the propagation of plane electromagnetic waves along a flat conducting surface and their relation to wireless telegraphy), Annalen der Physik, Sep. 20, 1907, pp. 846-866, Serial 4, vol. 23 (Includes English Translation and German Original).

Sommerfeld, A., Über die Ausbreitung der Wellen in der drahtlosen Telegraphie, Annalen der Physik, 1909, pp. 665-737, vol. 28, No. 4 (Includes English Translation and German Original).

Weyl, H., Ausbreitung elektromagnetischer Wellen über einem ebenen Leiter (Propagation of Electromagnetic Waves Over a Plane Conductor), Annalen der Physik, Nov. 1919, pp. 97-109, vol. 60 (Includes English Translation and German Original).

Sommerfeld, A., Ausbreitung der Wellen in der drahtlosen Telegraphie. Einfluss der Bodenbeschaffenheit auf gerichtete und ungerichtete Wellenzüge, Jahrbuch der drahtlosen Telegraphie und Telephonie, Dec. 1910, pp. 157-176 (Includes English Translation and German Original).

Van Der Pol et al., Über die Raumwellen von einem vertikalen Dipolsender auf ebener Erde, Ann. der Physik, Jul. 21, 1931, pp. 485-510, Ser. 5, vol. 10 (Includes English Translation and German Original).

Sommerfeld, A., Über die Fortpflanzung elektrodynamischer Wellen längs eines Drahtes, Annalen der Physik, 1899, pp. 233-290, vol. 67 (Includes English Translation and German Original).

Sommerfeld, A., Über die Ausbreitung der Wellen in der drahtlosen Telegraphie, Annalen der Physik, Dec. 1926, pp. 1135-1153, vol. 81 (Includes English Translation and German Original).

Weyl, H., Erwiderung auf Herrn Sommerfelds Bemerkungen über die Ausbreitung der Wellen in der drahtlosen Telegraphie, Annalen der Physik, 1920, pp. 110-112, vol. 62 (Includes English Translation and German Original).

Sommerfeld, A., Über die Ausbreitung der Wellen in der drahtlosen Telegraphie, Annalen der Physik, 1920, pp. 95-96, vol. 367, No. 9 (Includes English Translation and German Original).

Wolff, Christian, "Over the Horizon Oceanography Radar WERA," Oct. 13, 2011, https://web.archive.org/web/20111013010047/http://www.radartutorial.eu/19.kartei/karte712.en.html.

Kume, Hideyoshi, "Dengyo Converts Microwave Into Electricity with High Efficiency," Nikkei Electronics, May 17, 2011, http://techon.nikkeibp.co.jp/english/NEWS_EN/20110517/191846/.

Examination Report issued in New Zealand Application No. 712566 dated Jun. 10, 2016.

Examination Report issued in New Zealand for Application No. 720048 dated Jun. 28, 2016.

Singh A. K. et al., Excitation of surface electromagnetic waves on water, App Optics, Nov. 1, 1978, pp. 3459-3465, vol. 17, No. 21.

Olivier Balosso et al., Brief overview about Surface Wave theory and applications, 2012 15th International Symposium on Antenna Technology and Applied Electromagnetics (Antem), Jun. 25, 2012, pp. 1-7, IEEE.

International Search Report and Written Opinion for PCT/US2015/035598 dated Jul. 21, 2014.

Menelle M et al., Full digital high frequency surface wave radar: French trials in the Biscay bay, 2008 International Conference on RADAR, Sep. 2, 2008, pp. 224-229, IEEE, Piscataway, NJ, USA.

J. O. Hinz et al., A MIMO FMCW radar approach to HFSWR, Advances in Radio Science: ARS, Jul. 29, 2011, pp. 159-163, retrieved from the Internet: http://www.adv-radio-sci.net/9/159/2011/ars-9-159-2011.pdf (retrieved on Dec. 4, 2015), Katlenburg-Lindau, Germany.

Guohua Wang et al., High Resolution MIMO-HFSWR Radar Using Sparse Frequency Waveforms, Wireless Sensor Network, Oct. 1, 2009, pp. 152-162, vol. 1, No. 3.

International Search Report and Written Opinion for PCT/US2015/049505 dated Dec. 14, 2015.

International Search Report and Written Opinion for PCT/US2015/049394 dated Dec. 14, 2015.

(56) References Cited

OTHER PUBLICATIONS

International Search Report and Written Opinion for PCT/US2015/049064 dated Dec. 11, 2015.
International Search Report and Written Opinion for PCT/US2015/049509 dated Dec. 18, 2015.
H. M. Barlow et al., Surface Waves, Proceedings of the IRE, Nov. 1, 1953, pp. 329-341, vol. 100, No. 68, US.
International Search Report and Written Opinion for PCT/US2015/049171 dated Dec. 16, 2015.
International Search Report and Written Opinion for PCT/US2015/049435 dated Dec. 22, 2015.
International Search Report and Written Opinion for PCT/US2015/049424 dated Dec. 18, 2015.
International Search Report and Written Opinion for PCT/US2015/049151 dated Dec. 17, 2015.
International Search Report and Written Opinion for PCT/US2015/049161 dated Dec. 17, 2015.
International Search Report and Written Opinion for PCT/US2015/049518 dated Dec. 18, 2015.
International Search Report and Written Opinion for PCT/US2015/049154 dated Dec. 15, 2015.
Hambling, David, "Skimming the Surface: The Return of Tesla's Surface Waves", Published by Popular Mechanics on the Internet at http://www.popularmechanics.com/technology/infrastructure/a8778/ skimming-the-surface-the-return-of-teslas-surface-waves-153222501, Apr. 8, 2013, Popular Mechanics.
Barfield, R. H., "The Attenuation of Wireless Waves Over Land," Journal of the I.E.E. (British), Jan. 1928, pp. 204-214, vol. 66.
Michalski, K. A. et al., "The Sommerfeld half-space problem revisited: from radio frequencies and Zenneck waves to visible light and Fano modes," Journal of Electromagnetic Waves and Applications, Jan. 2016, pp. 1-42, vol. 30, No. 1, Taylor & Francis.
Noether, F., "Spreading of Electric Waves Along the Earth," published in the book translation Theory of Functions as Applied to Engineering Problems, Technology Press, 1942, pp. 167-184, Part 2, Section E, MIT. [Originally published by Springer, Berlin, in 1931 under the title Funktionentheorie and Ihre Anwendung in der Technik, Part II, R. Rothe, F. Ollendorf, and K. Pohlhausen, editors.].
Wu, Ke et al., Wireless Power Transmission, Technology, and Applications, Proceedings of the IEEE, Jun. 2013, pp. 1271-1275, vol. 101, No. 6.
Massa, Andrea et al., Array Designs for Long-Distance Wireless Power Transmission: State-of-the-Art and Innovative Solutions, Proceedings of the IEEE, Jun. 2013, pp. 1464-1481, vol. 101, No. 6.
Norton, K. A., The Propagation of Radio Waves Over the Surface of the Earth and in the Upper Atmosphere: Part I Ground-Wave Propagation from Short Antennas, Proc. IRE, Oct. 1936, pp. 1367-1387, vol. 24, No. 10.
Shinohara, Naoki, Beam Control Technologies with a High-Efficiency Phased Array for Microwave Power Transmission in Japan, Proceedings of the IEEE, Jun. 2013, pp. 1448-1463, vol. 101, No. 6.
Miyakoshi, Junji, Cellular and Molecular Responses to Radio-Frequency Electromagnetic Fields, Proceedings of the IEEE, Jun. 2013, pp. 1494-1502, vol. 101, No. 6.
Kim, Jiseong et al., Coil Design and Shielding Methods for a Magnetic Resonant Wireless Power Transfer System, Proceedings of the IEEE, Jun. 2013, pp. 1332-1342, vol. 101, No. 6.
Shoki, Hiroki, Issues and Initiatives for Practical Deployment of Wireless Power Transfer Technologies in Japan, Proceedings of the IEEE, Jun. 2013, pp. 1312-1320, vol. 101, No. 6.
Covic, Grant A. et al., Inductive Power Transfer, Proceedings of the IEEE, Jun. 2013, pp. 1276-1289, vol. 101, No. 6.
Strassner, Bernd et al., Microwave Power Transmission: Historical Milestones and System Components, Proceedings of the IEEE, Jun. 2013, pp. 1379-1396, vol. 101, No. 6.
Christ, Andreas et al., Assessing Human Exposure to Electromagnetic Fields from Wireless Power Transmission Systems, Proceedings of the IEEE, Jun. 2013, pp. 1482-1493, vol. 101, No. 6.
Jaffe, Paul et al., Energy Conversion and Transmission Modules for Space Solar Power, Proceedings of the IEEE, Jun. 2013, pp. 1424-1437, vol. 101, No. 6.
Tesla, Nikola, The Transmission of Electrical Energy Without Wires, Electrical World & Engineer, Mar. 5, 1904, pp. 429-431.
Hui, S. Y., Planar Wireless Charging Technology for Portable Electronic Products and Qi, Proceedings of the IEEE, Jun. 2013, pp. 1290-1301, vol. 101, No. 6.
Sasaki, Susumu et al., Microwave Power Transmission Technologies for Solar Power Satellites, Proceedings of the IEEE, Jun. 2013, pp. 1438-1447, vol. 101, No. 6.
Wang, Bingnan et al., Wireless Power Transfer: Metamaterials and Array of Coupled Resonators, Proceedings of the IEEE, Jun. 2013, pp. 1359-1368, vol. 101, No. 6.
Sample, Alanson P. et al., Enabling Seamless Wireless Power Delivery in Dynamic Environments, Proceedings of the IEEE, Jun. 2013, pp. 1343-1358, vol. 101, No. 6.
Visser, Hubregt J. et al., RF Energy Harvesting and Transport for Wireless Sensor Network Applications: Principles and Requirements, Proceedings of the IEEE, Jun. 2013, pp. 1410-1423, vol. 101, No. 6.
Popovic, Zoya et al., Low-Power Far-Field Wireless Powering for Wireless Sensors, Proceedings of the IEEE, Jun. 2013, pp. 1397-1409, vol. 101, No. 6.
Mayordomo, Iker et al., An Overview of Technical Challenges and Advances of Inductive Wireless Power Transmission, Proceedings of the IEEE, Jun. 2013, pp. 1302-1311, vol. 101, No. 6.
Garnica, Jaime et al., Wireless Power Transmission: From Far Field to Near Field, Proceedings of the IEEE, Jun. 2013, pp. 1321-1331, vol. 101, No. 6.
Ho, John S. et al., Midfield Wireless Powering for Implantable Systems, Proceedings of the IEEE, Jun. 2013, pp. 1369-1378, vol. 101, No. 6.
O'Neill, John J., Prodigal Genius: The Life of Nikola Tesla, 2008, pp. 121-217, Adventures Unlimited Press, Kempton, Illinois.
Cheney, Margaret, Tesla: Man Out of Time, 1981, pp. 171-191, Touchstone, New York, NY.
Burrows, C. R., The Surface Wave in Radio Transmission, Bell Laboratories Record, Jun. 1937, pp. 321-324, vol. 15.
Valone, Thomas, Harnessing the Wheelwork of Nature, Tesla's Science of Energy, 2002, pp. 147-269, Adventures Unlimited Press, Kempton, Illinois.
Tesla, Nikola, My Inventions, The Autobiography of Nikola Tesla, 2013, pp. 61-72, Lexington, KY.
Tesla, Nikola, From Colorado Springs to Long Island, Research Notes: Colorado Springs 1899-1900 New York 1900-1901, 2008, Nikola Tesla Museum **This reference has been uploaded in 3 parts due to size.
McMichael, I., A Note on the Brewster Angle in Lossy Dielectric Media, Night Vision and Electronic Sensors Directorate, Oct. 2010, pp. 1-11, US Army RDECOM CERDEC NVESD, Fort Belvior, Virginia.
Karalis, A., et al., Efficient Wireless Non-radiative Mid-range Energy Transfer, Annals of Physics, 2008, pp. 34-48, No. 323, Elsevier, Inc. (also made available online on Apr. 27, 2007).
Wadsworth, D., Approximate Integration Methods Applied to Wave Propagation (Thesis), Department of Geology and Geophysics, Massachusetts Institute of Technology, Thesis Submitted in Feb. 1958, pp. 1-128, Massachusetts Institute of Technology, Cambridge, Massachusetts, United States.
Pover, B., Report on the Performance of the Silsden 8 Metre Crossed Field Antenna, Published on the Internet at ok1mjo.com/all/ostatni/t-dab_dvb-t.../CFA_antena_silsden-report.pdf, Oct. 2009, pp. 1-28.
Corum, J. et al., The Application of Transmission Line Resonators to High Voltage RF Power Processing: History, Analysis and Experiment, IEEE 19th Southeastern Symposium on System Theory, Mar. 1987, pp. 45-50, Held at Clemson University, Clemson, South Carolina, United States.

(56) References Cited

OTHER PUBLICATIONS

Search Report and Written Opinion, PCT/US2014/019477, International Publication No. WO 2014/137817, entitled Excitation and Use of Guided Surface Waves on Lossy Media, International Publication Date: Sep. 12, 2014, International Filing Date: Feb. 28, 2014.

Wait, J. R., Excitation of Surface Waves on Conducting, Stratified, Dielectric-clad and Corrugated Surfaces, Research of the National Bureau of Standards, Dec. 1957, pp. 365-377, vol. 59, No. 6.

Marincic, A. S., Nikola Tesla and the Wireless Transmission of Energy, IEEE Transactions on Power Apparatus and Systems, Oct. 1982, pp. 58-59, vol. PAS-101, No. 10, IEEE, University of Belgrade, Belgrade, Yugoslavia.

Valentinuzzi, M.E., Nikola Tesla: Why Was He so Much Resisted and Forgotten?, IEEE Engineering in Medicine and Biology Magazine, Jul./Aug. 1998, pp. 74-75, vol. 17, No. 4, IEEE, Inst. de Bioingenieria, Univ. Nacional de Tucuman, Mexico.

Leyh, G.E. et al., Efficient Wireless Transmission of Power Using Resonators with Coupled Electric Fields, Power Symposium, 2008. NAPS '08. 40th North American, pp. 1-4, IEEE, Nevada Lightning Lab., NV, USA.

Marincic, A. et al., Tesla's Contribution to Radiowave Propagation, Telecommunications in Modern Satellite, Cable and Broadcasting Service, Sep. 2001, pp. 327-331, vol. 1, IEEE, Belgrade, Serbia.

Garnica, J. et al., Wireless Power Transmission: From Far Field to Near Field, Proceedings of the IEEE, Apr. 4, 2013, pp. 1321-1331, vol. 101, No. 6, IEEE, Gainesville, FL, USA.

Poljak, D. et al., Full Wave Model versus Transmission Line Representation of Tesla's Wave Propagation: 155th Anniversary of Birth of Nikola Tesla, 2011 19th International Conference on Software, Telecommunications and computer Networks (SoftCOM), Sep. 15-17, 2011, pp. 1-5, IEEE, Split, Croatia.

Li, Joshua Le-Wei et al., Keynote Speakers: Wireless Power Transfer: From Long-Distance Transmission to Short-Range Charging, 2013 IEEE International RF and Microwave Conference (RFM), Dec. 9-11, 2013, IEEE, Penang, Malaysia.

Keller, J. B. et al., Surface Waves Excitation and Propagation, Journal of Applied Physics, Jun. 1960, pp. 1039-1046, vol. 31, No. 6., AIP Publishing.

Chu, L. J., Physical Limitations on Omni-Directional Antennas, Journal of Applied Physics, Dec. 1948, pp. 1163-1175, vol. 19, AIP Publishing.

Wise, W. H., Note on Dipole Radiation Theory, Journal of Applied Physics, Oct. 1933, pp. 354-358, vol. 4, AIP Publishing.

Van Der Pol, B., Theory of the Reflection of the Light from a Point Source by a Finitely Conducting Flat Mirror, with an Application to Radiotelegraphy, Physica, Aug. 1935, pp. 843-853, vol. 2.

Friedman, B., Excitation of Surface Waves, the Institution of Electrical Engineers, Jan. 1958, pp. 252-258, Monograph No. 277 R.

Kabbary, F. M., Extremely Small High Power MW Broadcasting Antennas, IEE International Broadcasting Convention, Sep. 12-16, 1997, Conference Publication No. 447, Amsterdam.

Jordan, E. C. et al., Electromagnetic Waves and Radiating Systems, Second Edition, 1968, pp. 558-560, 730-734, Prentice-Hall, Inc., Englewood Cliffs, New Jersey.

Smythe, W. R., Static and Dynamic Electricity, 1950, pp. 542-547, McGraw-Hill Book Company, Inc., New York.

Zenneck, J., Wireless Telegraphy, Mar. 1918, McGraw-Hill Book Company, Inc., New York, NY, USA. (submitted in 2 parts).

Hendry, J. Surface Waves: what are They? Why are They Interesting?, Roke Manor Research Limited, 2009, pp. 1-10, Romsey, England.

Turner, J., Isolation of the Zenneck Surface Wave: Update, Roke Manor Research Limited, Romsey, England.

Schelkunoff, S. A., Modified Sommerfeld's Integral and Its Applications, Proceedings of the Institute of Radio Engineers, Oct. 1936, pp. 1388-1398, vol. 24, No. 10, IEEE, New York, NY, USA.

Wells, C.B., CFA Experiments, Electronics World + Wireless World, Mar. 1990, pp. 253-255, vol. 96.

Wells, C.B., The Cross-Field Antenna in Practice, Electronics World + Wireless World, Nov. 1989, pp. 1109-1111, vol. 95.

Wait, J.R., Theory of Ground Wave Propagation, Electromagnetic Probing in Geophysics, 1971, pp. 163-207, Golem Press.

Sarkar et al., History of Wireless, Jan. 17, 2006, Wiley-IEEE Press, Hoboken, NJ, USA. (submitted in 4 parts).

Stark III, J.C., Wireless Power Transmission Utilizing a Phased Array of Tesla Coils (Master's Thesis), May 13, 2004, pp. 1-247, MIT, Cambridge, MA, USA. (submitted in 2 parts).

Hardesty et al., Electrical Storms in Tesla's Colorado Springs Notes (& the Transmission of Energy w/o Wires), Tesla Science Center Conference, Nov. 5, 2011, Long Island, NY, USA. (Power Point Presentation).

Corum et al., A Technical Analysis of the Extra Coil as a Slow Wave Helical Resonator, Proceedings of the 2nd International Tesla Symposium, 1986, pp. 2-1 to 2-24, International Tesla Society, Colorado Springs, CO, USA.

Corum et al., Dr. Mahlon Loomis: Terra Alta's Neglected Discoverer of RF Communication, Proceedings of the 1992 International Tesla Symposium, pp. 19-34, International Tesla Society, Colorado Springs, CO, USA.

Corum et al., Summary Notes on Tesla Coils, Tesla Conference 2011, Published as Appendix 8 in Electrical Storms in Tesla's Colorado Springs Notes and the Transmission of Energy Without Wires, Nov. 5, 2011, pp. 1-14, Tesla Science Center at Wardenclyffe, Shoreham, NY, USA.

Hardesty et al., Franklin—Loomis—Tesla: The Origin and Development of Wireless Technology, Tesla Science Foundation Conference, Jul. 9-11, 2010, Philadelphia, PA, USA. (Power Point Presentation).

Hardesty et al., Franklin—Loomis—Tesla: The Origin of Modern Wireless Phenomena, Tesla Science Foundation Conference, Jul. 9-11, 2010, pp. 1-99, Philadelphia, PA, USA.

Corum et al., Goodness, Q and Power Factor in Electrical Science and Machinery, Infinite Energy Magazine, Jan./Feb. 2010, pp. 1-17, vol. 15, No. 89, New Energy Foundation, Concord, NH, USA.

Marriott, R. H., How Radio Grew Up, Radio Broadcast, Dec. 1925, pp. 159-162, vol. VIII, No. 2, Doubleday, Page & Co., Garden City, Ny, USA.

Goubau, G., Über die Zennecksche Bodenwelle (on the Zenneeck Surface Wave), Zeitschrift fur Angewandte Physik, 1951, pp. 103-107, vol. 3, No. 3/4, as translated by James F. Corum.

Pinzone, B.F., Pinzone Antiskywave Design, Radio World, May 15, 1988, pp. 45-46.

Corum et al., Experimental Replication of Loomis' RF Experiments, AAPT Summer Meeting, Jul. 24, 2006, Syracuse, NY, USA. (Power Point Presentation).

Corum et al., Tesla Coil Research, U.S. Army Armament Research, Development and Engineering Center, Contract No. DAAA21-90-C-0084, Jun. 1992.

Lebo, J.R., The Man Before Marconi: A Biography of Dr. Mahlon Loomis, QST, Aug. 1948, pp. 42-44.

Winters, S.R., The Story of Mahlon Loomis: Pioneer of Radio, Radio News, Nov. 1922, pp. 836-837, 966-980.

Kogan, S.H., Distribution of Waves Along an Infinite Helix, Reports of the Academy of Sciences of the USSR, 1949, pp. 1-5, vol. 66, No. 5, as translated by P.J. Pesavento and E. Corum.

U.S. Appl. No. 13/789,525, filed Mar. 7, 2013, Restriction Requirement dated Oct. 7, 2015.

U.S. Appl. No. 13/789,525, filed Mar. 7, 2013, Response to Restriction Requirement dated Oct. 7, 2015.

U.S. Appl. No. 13/789,525, filed Mar. 7, 2013, Non-Final Office Action dated Feb. 11, 2016.

U.S. Appl. No. 13/789,525, filed Mar. 7, 2013, Response to Non-Final Office Action dated Feb. 11, 2016.

U.S. Appl. No. 13/789,525, filed Mar. 7, 2013, Final Office Action dated Sep. 16, 2016.

International Search Report and Written Opinion for PCT/US2015/053242 dated Jan. 25, 2016.

Examination Report issued in New Zealand Application No. 712566 dated Nov. 30, 2015.

Office Action Issued in Chilean Application No. 2506-2015 dated Sep. 29, 2016. (Partial English Translation included).

(56) References Cited

OTHER PUBLICATIONS

"Wireless Transmission Theory, the Tesla Effect," Tesla Radio, Dec. 23, 2011, pp. 1-6.
Peterson, Gary, "Comparing the Hertz-Wave and Tesla Wireless Systems," Feedline, Oct. 27, 2012, pp. 1-7, 9, 21st Century Books, Breckenridge, CO.
International Search Report and Written Opinion for PCT/US2015/035598 dated Sep. 11, 2015.
Examination Report issued in Australian Application No. 2014226221 dated Sep. 22, 2016.
U.S. Appl. No. 13/789,538, filed Mar. 7, 2013, Restriction Requirement dated Oct. 7, 2015.
U.S. Appl. No. 13/789,538, filed Mar. 7, 2013, Response to Restriction Requirement dated Oct. 7, 2015.
U.S. Appl. No. 13/789,538, filed Mar. 7, 2013, Non-Final Office Action dated Feb. 8, 2016.
U.S. Appl. No. 13/789,538, filed Mar. 7, 2013, Response to Non-Final Action dated Feb. 8, 2016.
U.S. Appl. No. 13/789,538, filed Mar. 7, 2013, Notice of Allowance dated Oct. 7, 2016.
Hill, et. al. "On the excitation of the Zenneck surface wave over the ground at 10Hz," May 1980, Ann ales des Telecommunications, vol. 35, Issue 5, pp. 179-182.
U.S. Appl. No. 13/789,525, filed Mar. 7, 2013, Response to Final Office Action dated Sep. 16, 2016.
Peterson, Gary, "Rediscovering the zenneck surface wave," Feb. 8, 2008, Feedline No. 4, 1-5.
U.S. Appl. No. 14/728,492, filed Jun. 2, 2015, Non-Final Office Action dated Dec. 16, 2016.
U.S. Appl. No. 14/728,507, filed Jun. 2, 2015, Non-Final Office Action dated Jan. 3, 2017.
International Search Report and Written Opinion for PCT/US2016/047375, dated Dec. 2, 2016.
Patent Application PCT/US2016/047344 filed Aug. 17, 2016, International Search Report dated Feb. 8, 2017.
Patent Application PCT/US2016/047676 filed on Aug. 19, 2016, International Search Report dated Jan. 31, 2017.
Patent Application PCT/US2016/047672 filed on Aug. 19, 2016, International Search Report dated Nov. 3, 2016.
Patent Application PCT/US2016/046488 filed on Aug. 11, 2016, International Search Report dated Dec. 19, 2016.
Patent Application PCT/US2016/047674 filed on Aug. 19, 2016, International Search Report dated Dec. 20, 2016.
Patent Application PCT/US2016/047167 filed on Aug. 16, 2016, International Search Report dated Oct. 27, 2016.
Patent Application PCT/US2016/047375 filed on Aug. 17, 2016, International Search Report dated Dec. 2, 2016.
Patent Application PCT/US2016/047599 filed on Aug. 18, 2016, International Search Report dated Nov. 23, 2016.
Patent Application PCT/US2016/047673 filed on Aug. 19, 2016, International Search Report dated Nov. 29, 2016.
Patent Application PCT/US2016/047446 filed on Aug. 18, 2016, International Search Report dated Nov. 3, 2016.
Patent Application PCT/US2016/047353 filed on Aug. 17, 2016, International Search Report dated Nov. 16, 2016.
Patent Application PCT/US2016/047170 filed on Aug. 16, 2016, International Search Report dated Nov. 11, 2016.
Patent Application PCT/US2016/047611 filed on Aug. 18, 2016, International Search Report dated Nov. 11, 2016.
Patent Application PCT/US2016/047455 filed on Aug. 18, 2016, International Search Report and Written Opinion dated Nov. 7, 2006.
Patent Application PCT/US2016/047452 filed on Aug. 18, 2016, International Search Report and Written Opinion dated Nov. 17, 2016.
Leonhard, W., Electrical Engineering Between Energy and Information, Power Electronics and Motion Control Conference, 2000. Proceedings. PI EMC 2000. The Third International Aug. 15-18, 2000, IEEE, vol. 1, Aug. 15, 2000, pp. 197-202, Piscataway, NJ, USA.
Patent Application PCT/US2016/047451 filed on Aug. 18, 2016, International Search Report and Written Opinion dated Nov. 17, 2016.
Patent Application PCT/US16/47986 filed on Aug. 22, 2016, International Search Report and Written Opinion dated Nov. 17, 2016.
Patent Application PCT/US2016/047954 filed on Aug. 22, 2016, International Search Report and Written Opinion dated Nov. 24, 2016.
Zoran, B. et al, Some Notes on Transmission Line Representations of Tesla's Transmitters, 16th International Conference on Software, Telecommunications and Computer Networks, Softcom 2008, IEEE. Sep. 25, 2008, pp. 60-69, Piscataway. NJ, USA.
Patent Application PCT/US2016/047957 filed on Aug. 22, 2016, International Search Report and Written Opinion dated Nov. 17, 2016.
Patent Application PCT/US2016/048314 filed on Aug. 24, 2016, International Search Report and Written Opinion dated Nov. 17, 2016.
Patent Application PCT/US2016/047675 filed on Aug. 19, 2016, International Search Report and Written Opinion dated Nov. 25, 2016.
Patent Application PCT/US2016/047955 filed on Aug. 22, 2016, International Search Report and Written Opinion dated Nov. 17, 2016
Patent Application PCT/US2016/047457 filed on Aug. 18, 2016, International Search and Written Opinion dated Nov. 18, 2016.
Patent Application PCT/US2016/047368 filed on Aug. 17, 2016, International Search Report and Written Opinion dated Nov. 4, 2016.
Patent Application PCT/US2016/047338 filed on Aug. 17, 2016, International Search Report and Written Opinion dated Nov. 17, 2016.
Patent Application PCT/US2016/047598 filed on Aug. 18, 2016, International Search Report and Written Opinion dated Nov. 3, 2016.
Patent Application PCT/US2015/049236 filed on Sep. 9, 2015, International Search Report and Written Opinion dated Jan. 4, 2016.
Patent Application PCT/US2015/049511 filed on Sep. 10, 2015, International Search Report and Written Opinion dated Jan. 5, 2016.
Patent Application PCT/US2015/049523 filed on Sep. 10, 2015, International Search Report and Written Opinion dated Jan. 7, 2016.
Patent Application PCT/US2015/049497 filed on Sep. 10, 2015, International Search Report and Written Opinion dated Dec. 23, 2015.
Patent Application PCT/US2015/049520 filed on Sep. 10, 2015, International Search Report and Written Opinion dated Jan. 15, 2016.
Rich, G. J., The Launching of a Plane Surface Wave, Proceedings of the IEEE—Part B: Radio and Electronic Engineering, Mar. 1, 1955, pp. 237-246, vol. 102, No. 2, US.
Ranfagni, A. et al, Observation of Zenneck-type Waves in Microwave Propagation Experiments, Journal of Applied Physics, Jul. 2006, pp. 024910-1-024910-5, vol. 100, No. 2, US.
Mahmoud, S. F. et al, Reflection of Surface Waves on a Dielectic Image Line with Application to 'Guided RADAR', Microwave Symposium, 1972 IEEE GMTT International, May 22, 1972, pp. 139-141, Piscataway, NJ, US.
Examination Report issued in New Zealand Application No. 720048 dated May 12, 2017.
Examination Report issued in New Zealand Application No. 720048 dated Jan. 25, 2017.
Patent Application PCT/US2016/047350 filed on Aug. 17, 2016, International Search Report dated Mar. 9, 2017.
Patent Application PCT/US2015/049171 filed on Sep. 9, 2015, International Search Report and Written Opinion dated Dec. 16, 2015.
International Search Report and Written Opinion for PCT/US2016/047677 dated Oct. 18, 2016.
International Search Report and Written Opinion for PCT/US2016/047956 dated Oct. 21, 2016.
International Preliminary Search Report and Written Opinion for PCT/US2016/047375, dated Oct. 17, 2017.

(56) References Cited

OTHER PUBLICATIONS

Peterson, G., The Application of Electromagnetic Surface Waves to Wireless Energy Transfer, 2015 IEEE Wireless Power Transfer Conference (WPTC), May 1, 2015, pp. 1-4, Shoreham, Long Island, New York, USA.
Kukushkin, A. V., On the Existence and Physical Meaning of the Zenneck Wave, UFN, 2009, vol. 179, No. 7, 801-803.
Kistovich, Yu. V., On the Possibility of Observing Surface Zenneck Waves in the Radiation of a Source with a Small Vertical Aperture, Journal of Technical Physics, 1989, vol. 59(4), 16-21.
Datsko, V.N. and A.A. Kopylov, On Surface Electromagnetic Waves, UFN, 2008, vol. 178, No. 1, 109-110.
Baybakov et al., Experimental Discovery of Zenneck's Surface Electromagnetic Waves, UFN, 1989, vol. 157, 722-724.
Hesse et al., A Single Probe Spatial Averaging Technique for Guided Waves and Its Application to Surface Wave Rail Inspection, IEEE Transactions on Ultrasonics, Ferroelectrics, and Frequency Control, vol. 54, No. 11, Nov. 2007, 2344-2356.
Andriyas, T., Surface Wave Propagation in a Dielectric Waveguide Loaded with an Anistropic, Conductive, and Spatially Dispersive Substrate, Utah State University, May 2009, p. 12.
U.S. Appl. No. 14/483,089, filed Sep. 10, 2014, Non-Final Office Action dated Apr. 6, 2017.
U.S. Appl. No. 14/728,507, filed Jun. 2, 2015, Final Office Action dated Jul. 28, 2017.
Beaty, W., Tesla's Big Mistake?, Sep. 1999, http://amasci.com/tesla/tmistk.html.
Anonymous, Tesla Wireless Technology, Mar. 8, 2007, http://montalk.net/notes/tesla-wireless-technology.
Examination Report issued in Australian Application No. 2014226221 dated Sep. 20, 2017.
U.S. Appl. No. 14/848,653, filed Sep. 9, 2015, Final Office Action dated Sep. 25, 2017.
U.S. Appl. No. 14/849,643, filed Sep. 10, 2015, Non-Final Office Action dated Nov. 17, 2017.
New Zealand Patent Application NZ741388 filed on Aug. 17, 2016, 1st Examination Report dated Sep. 10, 2018.
Australian Patent Application AU2016320690 filed on Aug. 17, 2016, 1st Examination Report dated Aug. 16, 2018.

\* cited by examiner

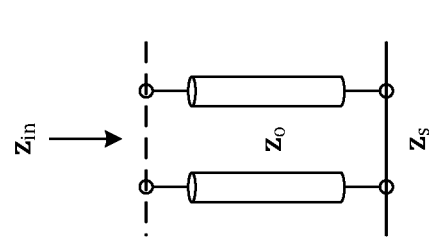
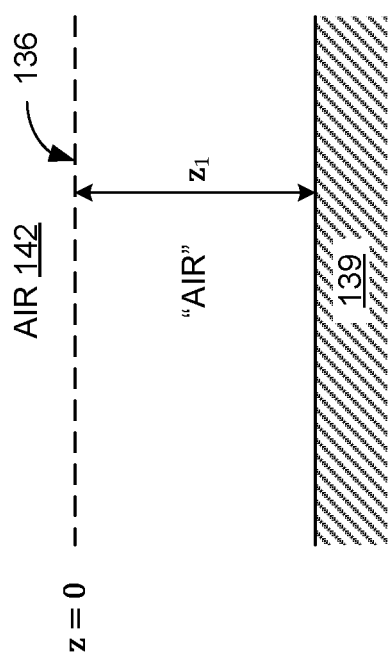
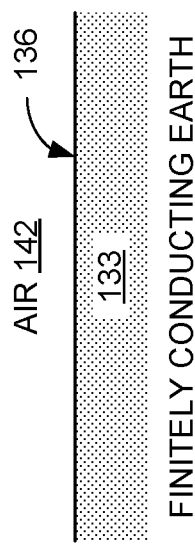
FIG. 8A
FIG. 8B
FIG. 8C

POWER INTERNAL MEDICAL DEVICES WITH GUIDED SURFACE WAVES

CROSS REFERENCE TO RELATED APPLICATIONS

This application claims priority to, and the benefit of, U.S. Provisional Patent Application entitled "Power Internal Medical Devices with Guided Surface Waves, which was filed on Sep. 9, 2015 and assigned Application No. 62/215,868, and which is incorporated herein by reference in its entirety. This application is related to U.S. Non-Provisional Patent Application entitled "Excitation and Use of Guided Surface Wave Modes on Lossy Media," which was filed on Mar. 7, 2013 and assigned application Ser. No. 13/789,538, and was published on Sep. 11, 2014 as Publication Number US2014/0252886 A1, and which is incorporated herein by reference in its entirety. This application is also related to U.S. Non-provisional Patent Application entitled "Excitation and Use of Guided Surface Wave Modes on Lossy Media," which was filed on Mar. 7, 2013 and assigned application Ser. No. 13/789,525, and was published on Sep. 11, 2014 as Publication Number US2014/0252865 A1, and which is incorporated herein by reference in its entirety. This application is further related to U.S. Non-provisional Patent Application entitled "Excitation and Use of Guided Surface Wave Modes on Lossy Media," which was filed on Sep. 10, 2014 and assigned application Ser. No. 14/483,089, and which is incorporated herein by reference in its entirety. This application is further related to U.S. Non-provisional Patent Application entitled "Excitation and Use of Guided Surface Waves," which was filed on Jun. 2, 2015 and assigned application Ser. No. 14/728,507, and which is incorporated herein by reference in its entirety. This application is further related to U.S. Non-provisional Patent Application entitled "Excitation and Use of Guided Surface Waves," which was filed on Jun. 2, 2015 and assigned application Ser. No. 14/728,492, and which is incorporated herein by reference in its entirety.

BACKGROUND

In the medical industry, medical devices are commonly implanted into patients to provide continuous care for patients that are high risk. For instance, a patient with a heart arrhythmia may have a pacemaker implanted within the chest cavity with electronic leads connected to the heart in order to provide an electric impulse to the heart if the patient's heartbeat requires defibrillation. Such devices may need to be replaced every few years due to the fact that batteries in such devices become discharged or worn out. Such replacement can involve surgery that presents a risk to patients.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

FIGS. 8A through 8C are graphical representations illustrating examples of equivalent image plane models of the guided surface waveguide probe of FIGS. 3 and 7 according to various embodiments of the present disclosure.

DETAILED DESCRIPTION

Figure 1:
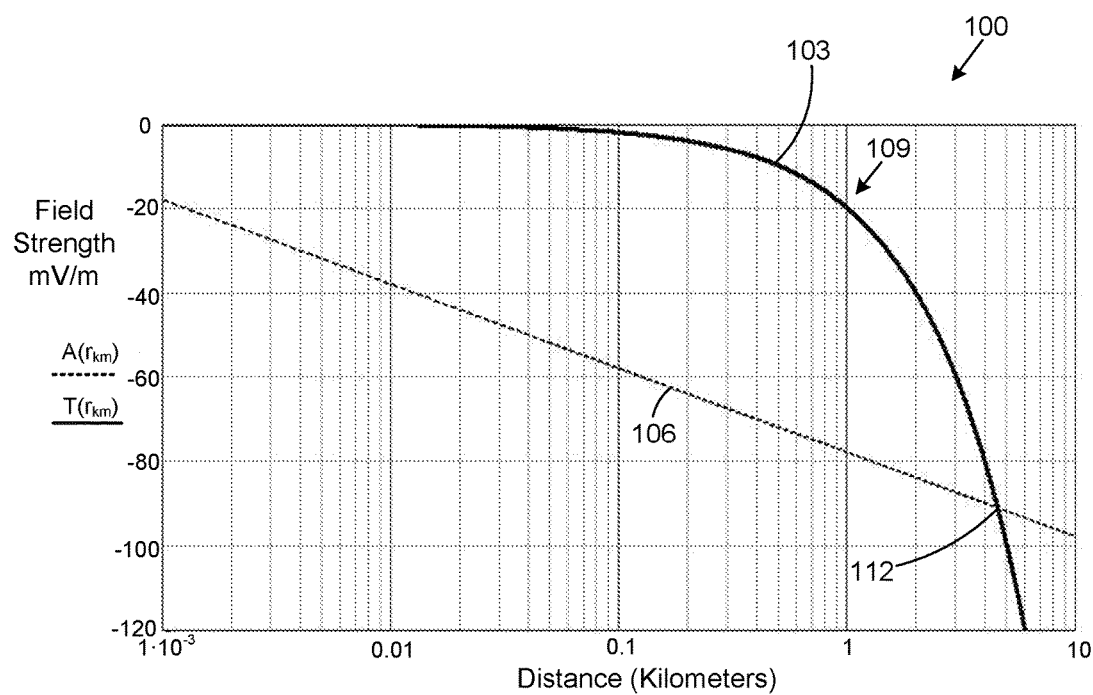
FIG. 1 is a chart that depicts field strength as a function of distance for a guided electromagnetic field and a radiated electromagnetic field.

To begin, some terminology shall be established to provide clarity in the discussion of concepts to follow. First, as contemplated herein, a formal distinction is drawn between radiated electromagnetic fields and guided electromagnetic fields.

As contemplated herein, a radiated electromagnetic field comprises electromagnetic energy that is emitted from a source structure in the form of waves that are not bound to a waveguide. For example, a radiated electromagnetic field is generally a field that leaves an electric structure such as an antenna and propagates through the atmosphere or other medium and is not bound to any waveguide structure. Once radiated electromagnetic waves leave an electric structure such as an antenna, they continue to propagate in the medium of propagation (such as air) independent of their source until they dissipate regardless of whether the source continues to operate. Once electromagnetic waves are radiated, they are not recoverable unless intercepted, and, if not intercepted, the energy inherent in the radiated electromagnetic waves is lost forever. Electrical structures such as antennas are designed to radiate electromagnetic fields by maximizing the ratio of the radiation resistance to the structure loss resistance. Radiated energy spreads out in space and is lost regardless of whether a receiver is present. The energy density of the radiated fields is a function of distance due to geometric spreading. Accordingly, the term "radiate" in all its forms as used herein refers to this form of electromagnetic propagation.

A guided electromagnetic field is a propagating electromagnetic wave whose energy is concentrated within or near boundaries between media having different electromagnetic properties. In this sense, a guided electromagnetic field is one that is bound to a waveguide and may be characterized as being conveyed by the current flowing in the waveguide. If there is no load to receive and/or dissipate the energy conveyed in a guided electromagnetic wave, then no energy is lost except for that dissipated in the conductivity of the guiding medium. Stated another way, if there is no load for a guided electromagnetic wave, then no energy is consumed. Thus, a generator or other source generating a guided electromagnetic field does not deliver real power unless a resistive load is present. To this end, such a generator or other source essentially runs idle until a load is presented. This is akin to running a generator to generate a 60 Hertz electromagnetic wave that is transmitted over power lines where there is no electrical load. It should be noted that a guided electromagnetic field or wave is the equivalent to what is termed a "transmission line mode." This contrasts with radiated electromagnetic waves in which real power is supplied at all times in order to generate radiated waves. Unlike radiated electromagnetic waves, guided electromagnetic energy does not continue to propagate along a finite length waveguide after the energy source is turned off. Accordingly, the term "guide" in all its forms as used herein refers to this transmission mode of electromagnetic propagation.

Referring now to FIG. 1, shown is a graph 100 of field strength in decibels (dB) above an arbitrary reference in volts per meter as a function of distance in kilometers on a log-dB plot to further illustrate the distinction between radiated and guided electromagnetic fields. The graph 100 of FIG. 1 depicts a guided field strength curve 103 that shows the field strength of a guided electromagnetic field as a function of distance. This guided field strength curve 103 is essentially the same as a transmission line mode. Also, the graph 100 of FIG. 1 depicts a radiated field strength curve 106 that shows the field strength of a radiated electromagnetic field as a function of distance.

Of interest are the shapes of the curves 103 and 106 for guided wave and for radiation propagation, respectively. The radiated field strength curve 106 falls off geometrically (1/d, where d is distance), which is depicted as a straight line on the log-log scale. The guided field strength curve 103, on the other hand, has a characteristic exponential decay of $e^{-\alpha d}/\sqrt{d}$ and exhibits a distinctive knee 109 on the log-log scale. The guided field strength curve 103 and the radiated field strength curve 106 intersect at point 112, which occurs at a crossing distance. At distances less than the crossing distance at intersection point 112, the field strength of a guided electromagnetic field is significantly greater at most locations than the field strength of a radiated electromagnetic field. At distances greater than the crossing distance, the opposite is true. Thus, the guided and radiated field strength curves 103 and 106 further illustrate the fundamental propagation difference between guided and radiated electromagnetic fields. For an informal discussion of the difference between guided and radiated electromagnetic fields, reference is made to Milligan, T., *Modern Antenna Design*, McGraw-Hill, 1$^{st}$ Edition, 1985, pp. 8-9, which is incorporated herein by reference in its entirety.

The distinction between radiated and guided electromagnetic waves, made above, is readily expressed formally and placed on a rigorous basis. That two such diverse solutions could emerge from one and the same linear partial differential equation, the wave equation, analytically follows from the boundary conditions imposed on the problem. The Green function for the wave equation, itself, contains the distinction between the nature of radiation and guided waves.

In empty space, the wave equation is a differential operator whose eigenfunctions possess a continuous spectrum of eigenvalues on the complex wave-number plane. This transverse electro-magnetic (TEM) field is called the radiation field, and those propagating fields are called "Hertzian waves." However, in the presence of a conducting boundary, the wave equation plus boundary conditions mathematically lead to a spectral representation of wave-numbers composed of a continuous spectrum plus a sum of discrete spectra. To this end, reference is made to Sommerfeld, A., "Uber die Ausbreitung der Wellen in der Drahtlosen Telegraphie," Annalen der Physik, Vol. 28, 1909, pp. 665-736. Also see Sommerfeld, A., "Problems of Radio," published as Chapter 6 in *Partial Differential Equations in Physics—Lectures on Theoretical Physics: Volume VI*, Academic Press, 1949, pp. 236-289, 295-296; Collin, R. E., "Hertzian Dipole Radiating Over a Lossy Earth or Sea: Some Early and Late 20$^{th}$ Century Controversies," IEEE Antennas and Propagation Magazine, Vol. 46, No. 2, April 2004, pp. 64-79; and Reich, H. J., Ordnung, P. F, Krauss, H. L., and Skalnik, J. G., *Microwave Theory and Techniques*, Van Nostrand, 1953, pp. 291-293, each of these references being incorporated herein by reference in its entirety.

The terms "ground wave" and "surface wave" identify two distinctly different physical propagation phenomena. A surface wave arises analytically from a distinct pole yielding a discrete component in the plane wave spectrum. See, e.g., "The Excitation of Plane Surface Waves" by Cullen, A. L., (*Proceedings of the IEE* (British), Vol. 101, Part IV, August 1954, pp. 225-235). In this context, a surface wave is considered to be a guided surface wave. The surface wave (in the Zenneck-Sommerfeld guided wave sense) is, physically and mathematically, not the same as the ground wave (in the Weyl-Norton-FCC sense) that is now so familiar from radio broadcasting. These two propagation mechanisms arise from the excitation of different types of eigenvalue spectra (continuum or discrete) on the complex plane. The field strength of the guided surface wave decays exponentially with distance as illustrated by curve 103 of FIG. 1 (much like propagation in a lossy waveguide) and resembles propagation in a radial transmission line, as opposed to the classical Hertzian radiation of the ground wave, which propagates spherically, possesses a continuum of eigenvalues, falls off geometrically as illustrated by curve 106 of FIG. 1, and results from branch-cut integrals. As experimentally demonstrated by C. R. Burrows in "The Surface Wave in Radio Propagation over Plane Earth" (*Proceedings of the IRE*, Vol. 25, No. 2, February, 1937, pp. 219-229) and "The Surface Wave in Radio Transmission" (*Bell Laboratories Record*, Vol. 15, June 1937, pp. 321-324), vertical antennas radiate ground waves but do not launch guided surface waves.

To summarize the above, first, the continuous part of the wave-number eigenvalue spectrum, corresponding to branch-cut integrals, produces the radiation field, and second, the discrete spectra, and corresponding residue sum arising from the poles enclosed by the contour of integration, result in non-TEM traveling surface waves that are exponentially damped in the direction transverse to the propagation. Such surface waves are guided transmission line modes. For further explanation, reference is made to Friedman, B., *Principles and Techniques of Applied Mathematics*, Wiley, 1956, pp. 214, 283-286, 290, 298-300.

In free space, antennas excite the continuum eigenvalues of the wave equation, which is a radiation field, where the outwardly propagating RF energy with $E_z$ and $H_\phi$ in-phase is lost forever. On the other hand, waveguide probes excite discrete eigenvalues, which results in transmission line propagation. See Collin, R. E., *Field Theory of Guided Waves*, McGraw-Hill, 1960, pp. 453, 474-477. While such theoretical analyses have held out the hypothetical possibility of launching open surface guided waves over planar or spherical surfaces of lossy, homogeneous media, for more than a century no known structures in the engineering arts have existed for accomplishing this with any practical efficiency. Unfortunately, since it emerged in the early 1900's, the theoretical analysis set forth above has essentially remained a theory and there have been no known structures for practically accomplishing the launching of open surface guided waves over planar or spherical surfaces of lossy, homogeneous media.

According to the various embodiments of the present disclosure, various guided surface waveguide probes are described that are configured to excite electric fields that couple into a guided surface waveguide mode along the surface of a lossy conducting medium. Such guided electromagnetic fields are substantially mode-matched in magnitude and phase to a guided surface wave mode on the surface of the lossy conducting medium. Such a guided surface wave mode can also be termed a Zenneck waveguide mode. By virtue of the fact that the resultant fields excited by the guided surface waveguide probes described herein are substantially mode-matched to a guided surface waveguide mode on the surface of the lossy conducting medium, a guided electromagnetic field in the form of a guided surface wave is launched along the surface of the lossy conducting medium. According to one embodiment, the lossy conducting medium comprises a terrestrial medium such as the Earth.

Figure 2:
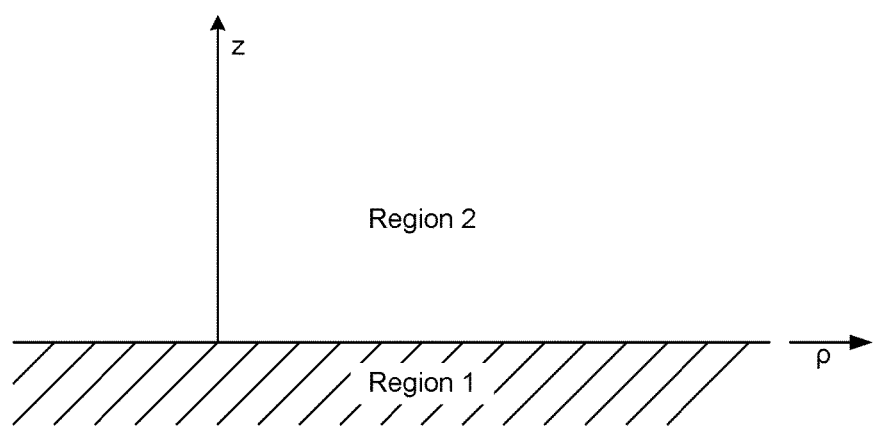
FIG. 2 is a drawing that illustrates a propagation interface with two regions employed for transmission of a guided surface wave according to various embodiments of the present disclosure.

Referring to FIG. 2, shown is a propagation interface that provides for an examination of the boundary value solutions to Maxwell's equations derived in 1907 by Jonathan Zenneck as set forth in his paper Zenneck, J., "On the Propagation of Plane Electromagnetic Waves Along a Flat Conducting Surface and their Relation to Wireless Telegraphy," Annalen der Physik, Serial 4, Vol. 23, Sep. 20, 1907, pp. 846-866. FIG. 2 depicts cylindrical coordinates for radially propagating waves along the interface between a lossy conducting medium specified as Region 1 and an insulator specified as Region 2. Region 1 can comprise, for example, any lossy conducting medium. In one example, such a lossy conducting medium can comprise a terrestrial medium such as the Earth or other medium. Region 2 is a second medium that shares a boundary interface with Region 1 and has different constitutive parameters relative to Region 1. Region 2 can comprise, for example, any insulator such as the atmosphere or other medium. The reflection coefficient for such a boundary interface goes to zero only for incidence at a complex Brewster angle. See Stratton, J. A., *Electromagnetic Theory*, McGraw-Hill, 1941, p. 516.

According to various embodiments, the present disclosure sets forth various guided surface waveguide probes that generate electromagnetic fields that are substantially mode-matched to a guided surface waveguide mode on the surface of the lossy conducting medium comprising Region 1. According to various embodiments, such electromagnetic fields substantially synthesize a wave front incident at a complex Brewster angle of the lossy conducting medium that can result in zero reflection.

To explain further, in Region 2, where an $e^{j\omega t}$ field variation is assumed and where $\rho \neq 0$ and $z \geq 0$ (with z being the vertical coordinate normal to the surface of Region 1, and $\rho$ being the radial dimension in cylindrical coordinates), Zenneck's closed-form exact solution of Maxwell's equations satisfying the boundary conditions along the interface are expressed by the following electric field and magnetic field components:

$$H_{2\phi} = Ae^{-u_2 z}H_1^{(2)}(-j\gamma\rho), \quad (1)$$

$$E_{2\rho} = A\left(\frac{u_2}{j\omega\varepsilon_o}\right)e^{-u_2 z}H_1^{(2)}(-j\gamma\rho), \quad (2)$$

and $$E_{2z} = A\left(\frac{-\gamma}{\omega\varepsilon_o}\right)e^{-u_2 z}H_0^{(2)}(-j\gamma\rho). \quad (3)$$

In Region 1, where the $e^{j\omega t}$ field variation is assumed and where $\rho \neq 0$ and $z \leq 0$, Zenneck's closed-form exact solution of Maxwell's equations satisfying the boundary conditions along the interface is expressed by the following electric field and magnetic field components:

$$H_{1\phi} = Ae^{-u_1 z}H_1^{(2)}(-j\gamma\rho), \quad (4)$$

$$E_{1\rho} = A\left(\frac{-u_1}{\sigma_1 + j\omega\varepsilon_1}\right)e^{-u_1 z}H_1^{(2)}(-j\gamma\rho), \quad (5)$$

and $$E_{1z} = A\left(\frac{-j\gamma}{\sigma_1 + j\omega\varepsilon_1}\right)e^{-u_1 z}H_0^{(2)}(-j\gamma\rho). \quad (6)$$

In these expressions, z is the vertical coordinate normal to the surface of Region 1 and $\rho$ is the radial coordinate, $H_n^{(2)}(-j\gamma\rho)$ is a complex argument Hankel function of the second kind and order n, $u_1$ is the propagation constant in the positive vertical (z) direction in Region 1, $u_2$ is the propagation constant in the vertical (z) direction in Region 2, $\sigma_1$ is the conductivity of Region 1, $\omega$ is equal to $2\pi f$, where f is a frequency of excitation, $\varepsilon_o$ is the permittivity of free space, $\varepsilon_1$ is the permittivity of Region 1, A is a source constant imposed by the source, and $\gamma$ is a surface wave radial propagation constant.

The propagation constants in the $\pm z$ directions are determined by separating the wave equation above and below the interface between Regions 1 and 2, and imposing the boundary conditions. This exercise gives, in Region 2, $$u_2 = \frac{-jk_o}{\sqrt{1 + (\varepsilon_r - jx)}} \quad (7)$$

and gives, in Region 1, $$u_1 = -u_2(\varepsilon_r - jx). \quad (8)$$

The radial propagation constant $\gamma$ is given by $$\gamma = j\sqrt{k_o^2 + u_2^2} = j\frac{k_o n}{\sqrt{1+n^2}}, \quad (9)$$

which is a complex expression where n is the complex index of refraction given by $$n = \sqrt{\varepsilon_r - jx}. \quad (10)$$

In all of the above Equations, $$x = \frac{\sigma_1}{\omega\varepsilon_o}, \quad (11)$$

and $$k_o = \omega\sqrt{\mu_o\varepsilon_o} = \frac{\lambda_o}{2\pi}, \quad (12)$$

where $\varepsilon_r$ comprises the relative permittivity of Region 1, $\sigma_1$ is the conductivity of Region 1, $\varepsilon_o$ is the permittivity of free space, and $\mu_o$ comprises the permeability of free space. Thus, the generated surface wave propagates parallel to the interface and exponentially decays vertical to it. This is known as evanescence.

Thus, Equations (1)-(3) can be considered to be a cylindrically-symmetric, radially-propagating waveguide mode. See Barlow, H. M., and Brown, J., *Radio Surface Waves*, Oxford University Press, 1962, pp. 10-12, 29-33. The present disclosure details structures that excite this "open boundary" waveguide mode. Specifically, according to various embodiments, a guided surface waveguide probe is provided with a charge terminal of appropriate size that is fed with voltage and/or current and is positioned relative to the boundary interface between Region 2 and Region 1. This may be better understood with reference to FIG. 3, which shows an example of a guided surface waveguide probe 200a that includes a charge terminal $T_1$ elevated above a lossy conducting medium 203 (e.g., the Earth) along a vertical axis z that is normal to a plane presented by the lossy conducting medium 203. The lossy conducting medium 203 makes up Region 1, and a second medium 206 makes up Region 2 and shares a boundary interface with the lossy conducting medium 203.

According to one embodiment, the lossy conducting medium 203 can comprise a terrestrial medium such as the planet Earth. To this end, such a terrestrial medium comprises all structures or formations included thereon whether natural or man-made. For example, such a terrestrial medium can comprise natural elements such as rock, soil, sand, fresh water, sea water, trees, vegetation, and all other natural elements that make up our planet. In addition, such a terrestrial medium can comprise man-made elements such as concrete, asphalt, building materials, and other man-made materials. In other embodiments, the lossy conducting medium 203 can comprise some medium other than the Earth, whether naturally occurring or man-made. In other embodiments, the lossy conducting medium 203 can comprise other media such as man-made surfaces and structures such as automobiles, aircraft, man-made materials (such as plywood, plastic sheeting, or other materials) or other media.

In the case where the lossy conducting medium 203 comprises a terrestrial medium or Earth, the second medium 206 can comprise the atmosphere above the ground. As such, the atmosphere can be termed an "atmospheric medium" that comprises air and other elements that make up the atmosphere of the Earth. In addition, it is possible that the second medium 206 can comprise other media relative to the lossy conducting medium 203.

The guided surface waveguide probe 200a includes a feed network 209 that couples an excitation source 212 to the charge terminal $T_1$ via, e.g., a vertical feed line conductor. According to various embodiments, a charge $Q_1$ is imposed on the charge terminal $T_1$ to synthesize an electric field based upon the voltage applied to terminal $T_1$ at any given instant. Depending on the angle of incidence ($\theta_i$) of the electric field (E), it is possible to substantially mode-match the electric field to a guided surface waveguide mode on the surface of the lossy conducting medium 203 comprising Region 1.

By considering the Zenneck closed-form solutions of Equations (1)-(6), the Leontovich impedance boundary condition between Region 1 and Region 2 can be stated as $$\hat{z} \times \vec{H}_2(\rho,\varphi,0) = \vec{J}_S, \tag{13}$$

where $\hat{z}$ is a unit normal in the positive vertical (+z) direction and $\vec{H}_2$ is the magnetic field strength in Region 2 expressed by Equation (1) above. Equation (13) implies that the electric and magnetic fields specified in Equations (1)-(3) may result in a radial surface current density along the boundary interface, where the radial surface current density can be specified by $$J_\rho(\rho') = -A H_1^{(2)}(-j\gamma\rho') \tag{14}$$

where A is a constant. Further, it should be noted that close-in to the guided surface waveguide probe 200 (for $\rho \ll \lambda$), Equation (14) above has the behavior $$J_{close}(\rho') = \frac{-A(j2)}{\pi(-j\gamma\rho')} = -H_\phi = -\frac{I_o}{2\pi\rho'}. \tag{15}$$

Figure 3:
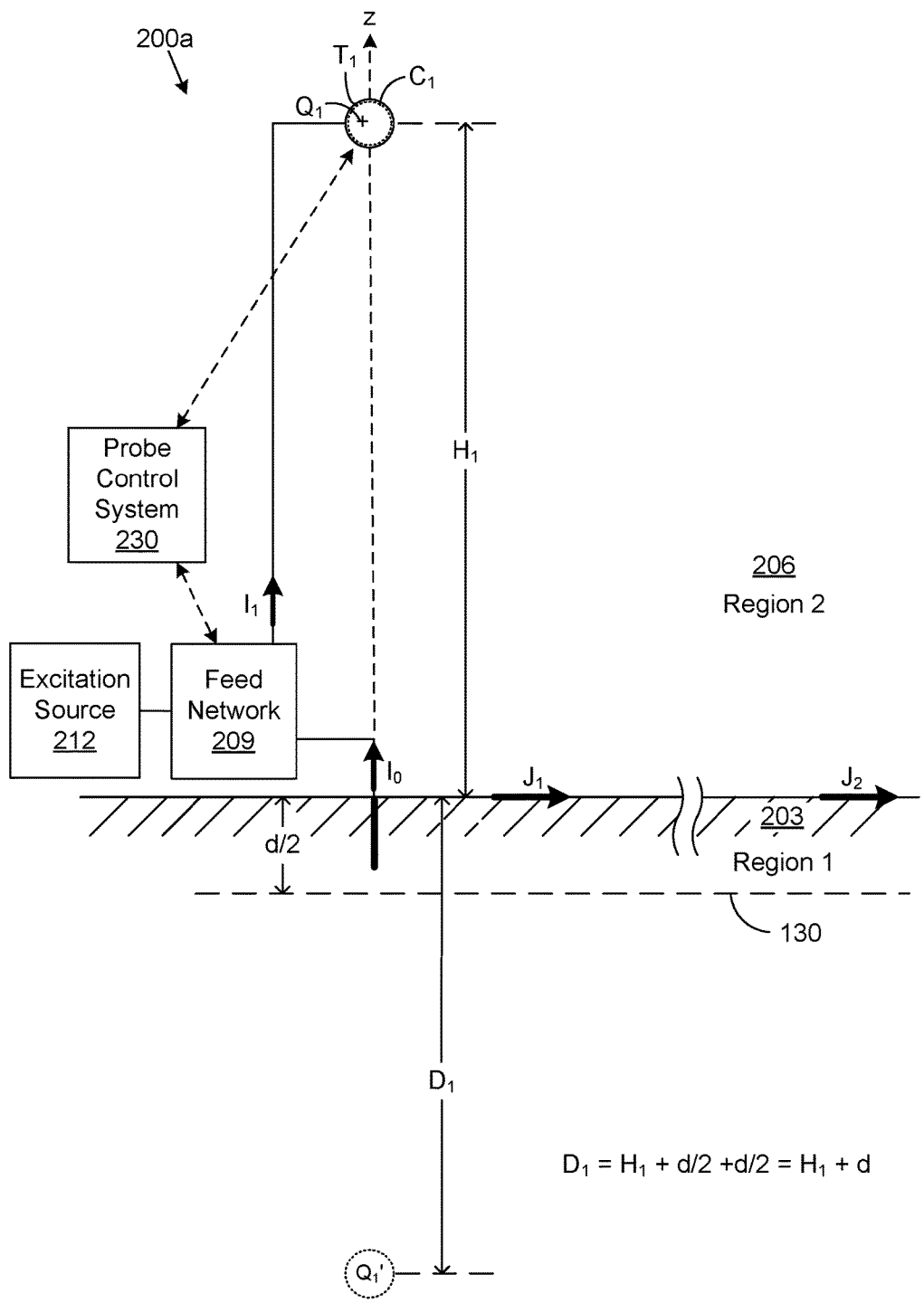
FIG. 3 is a drawing that illustrates a guided surface waveguide probe disposed with respect to a propagation interface of FIG. 2 according to various embodiments of the present disclosure.

The negative sign means that when source current ($I_o$) flows vertically upward as illustrated in FIG. 3, the "close-in" ground current flows radially inward. By field matching on $H_\phi$ "close-in," it can be determined that $$A = -\frac{I_o \gamma}{4} = -\frac{\omega q_1 \gamma}{4} \tag{16}$$

where $q_1 = C_1 V_1$, in Equations (1)-(6) and (14). Therefore, the radial surface current density of Equation (14) can be restated as $$J_\rho(\rho') = \frac{I_o \gamma}{4} H_1^{(2)}(-j\gamma\rho'). \tag{17}$$

The fields expressed by Equations (1)-(6) and (17) have the nature of a transmission line mode bound to a lossy interface, not radiation fields that are associated with ground-wave propagation. See Barlow, H. M. and Brown, J., *Radio Surface Waves*, Oxford University Press, 1962, pp. 1-5.

At this point, a review of the nature of the Hankel functions used in Equations (1)-(6) and (17) is provided for these solutions of the wave equation. One might observe that the Hankel functions of the first and second kind and order n are defined as complex combinations of the standard Bessel functions of the first and second kinds $$H_n^{(1)}(x) = J_n(x) + jN_n(x), \text{ and} \tag{18}$$

$$H_n^{(2)}(x) = J_n(x) - jN_n(x), \tag{19}$$

These functions represent cylindrical waves propagating radially inward ($H_n^{(1)}$) and outward ($H_n^{(2)}$), respectively. The definition is analogous to the relationship $e^{\pm jx} = \cos x \pm j \sin x$. See, for example, Harrington, R. F., *Time-Harmonic Fields*, McGraw-Hill, 1961, pp. 460-463.

That $H_n^{(2)}(k_\rho \rho)$ is an outgoing wave can be recognized from its large argument asymptotic behavior that is obtained directly from the series definitions of $J_n(x)$ and $N_n(x)$. Far-out from the guided surface waveguide probe:

$$H_n^{(2)}(x) \xrightarrow[x \to \infty]{} \sqrt{\frac{2j}{\pi x}} j^n e^{-jx} = \sqrt{\frac{2}{\pi x}} j^n e^{-j\left(x - \frac{\pi}{4}\right)}, \tag{20a}$$

which, when multiplied by $e^{j\omega t}$, is an outward propagating cylindrical wave of the form $e^{j(\omega t - k\rho)}$ with a $1/\sqrt{\rho}$ spatial variation. The first order (n=1) solution can be determined from Equation (20a) to be $$H_1^{(2)}(x) \xrightarrow[x \to \infty]{} j\sqrt{\frac{2j}{\pi x}} e^{-jx} = \sqrt{\frac{2}{\pi x}} e^{-j\left(x - \frac{\pi}{2} - \frac{\pi}{4}\right)}. \tag{20b}$$

Close-in to the guided surface waveguide probe (for $\rho \ll \lambda$), the Hankel function of first order and the second kind behaves as $$H_1^{(2)}(x) \xrightarrow[x \to 0]{} \frac{2j}{\pi x}. \tag{21}$$

Note that these asymptotic expressions are complex quantities. When x is a real quantity, Equations (20b) and (21) differ in phase by $\sqrt{j}$, which corresponds to an extra phase advance or "phase boost" of 45° or, equivalently, $\lambda/8$. The close-in and far-out asymptotes of the first order Hankel function of the second kind have a Hankel "crossover" or transition point where they are of equal magnitude at a distance of $\rho = R_x$.

Thus, beyond the Hankel crossover point the "far out" representation predominates over the "close-in" representation of the Hankel function. The distance to the Hankel crossover point (or Hankel crossover distance) can be found by equating Equations (20b) and (21) for $-j\gamma\rho$, and solving for $R_x$. With $x = \sigma/\omega\varepsilon_o$, it can be seen that the far-out and close-in Hankel function asymptotes are frequency dependent, with the Hankel crossover point moving out as the frequency is lowered. It should also be noted that the Hankel function asymptotes may also vary as the conductivity ($\sigma$) of the lossy conducting medium changes. For example, the conductivity of the soil can vary with changes in weather conditions.

Figure 4:
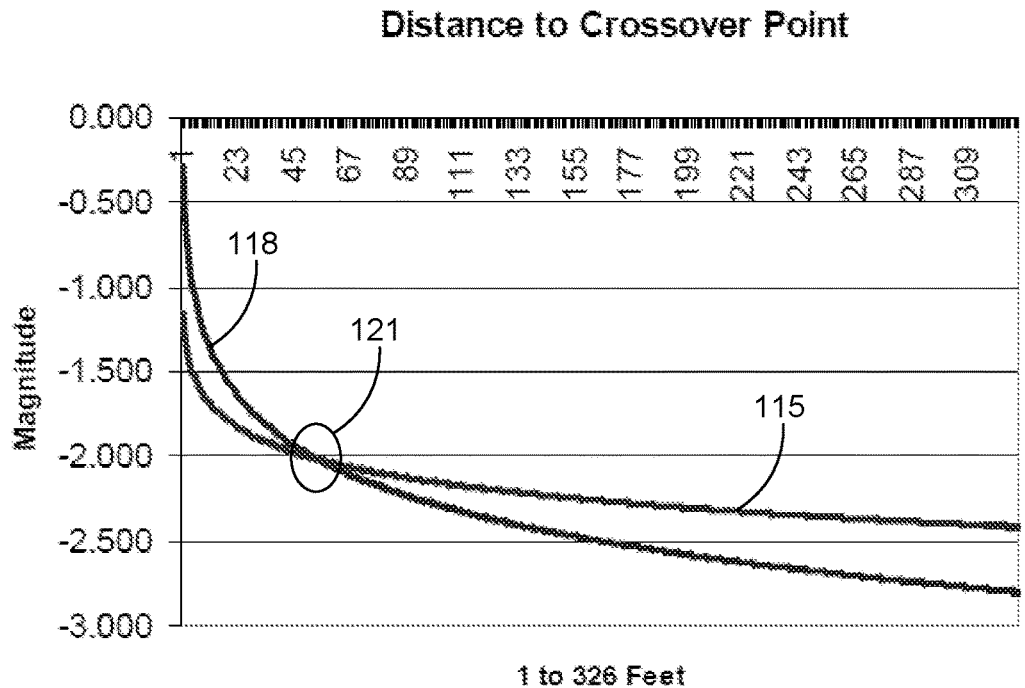
FIG. 4 is a plot of an example of the magnitudes of close-in and far-out asymptotes of first order Hankel functions according to various embodiments of the present disclosure.

Referring to FIG. 4, shown is an example of a plot of the magnitudes of the first order Hankel functions of Equations (20b) and (21) for a Region 1 conductivity of $\sigma = 0.010$ mhos/m and relative permittivity $\varepsilon_r = 15$, at an operating frequency of 1850 kHz. Curve 115 is the magnitude of the far-out asymptote of Equation (20b) and curve 118 is the magnitude of the close-in asymptote of Equation (21), with the Hankel crossover point 121 occurring at a distance of $R_x = 54$ feet. While the magnitudes are equal, a phase offset exists between the two asymptotes at the Hankel crossover point 121. It can also be seen that the Hankel crossover distance is much less than a wavelength of the operation frequency.

Considering the electric field components given by Equations (2) and (3) of the Zenneck closed-form solution in Region 2, it can be seen that the ratio of $E_z$ and $E_\rho$ asymptotically passes to $$\frac{E_z}{E_\rho} = \left(\frac{-j\gamma}{u_2}\right) \frac{H_0^{(2)}(-j\gamma\rho)}{H_1^{(2)}(-j\gamma\rho)} \xrightarrow[\rho\to\infty]{} \sqrt{\varepsilon_r - j\frac{\sigma}{\omega\varepsilon_o}} = n = \tan\theta_i, \quad (22)$$

where n is the complex index of refraction of Equation (10) and $\theta_i$ is the angle of incidence of the electric field. In addition, the vertical component of the mode-matched electric field of Equation (3) asymptotically passes to $$E_{2z} \xrightarrow[\rho\to\infty]{} \left(\frac{q_{free}}{\varepsilon_o}\right)\sqrt{\frac{\gamma^3}{8\pi}} e^{-u_2 z} \frac{e^{-j(\gamma\rho-\pi/4)}}{\sqrt{\rho}}, \quad (23)$$

which is linearly proportional to free charge on the isolated component of the elevated charge terminal's capacitance at the terminal voltage, $q_{free}=C_{free}\times V_T$.

For example, the height $H_1$ of the elevated charge terminal $T_1$ in FIG. 3 affects the amount of free charge on the charge terminal $T_1$. When the charge terminal $T_1$ is near the ground plane of Region 1, most of the charge $Q_1$ on the terminal is "bound." As the charge terminal $T_1$ is elevated, the bound charge is lessened until the charge terminal $T_1$ reaches a height at which substantially all of the isolated charge is free.

The advantage of an increased capacitive elevation for the charge terminal $T_1$ is that the charge on the elevated charge terminal $T_1$ is further removed from the ground plane, resulting in an increased amount of free charge $q_{free}$ to couple energy into the guided surface waveguide mode. As the charge terminal $T_1$ is moved away from the ground plane, the charge distribution becomes more uniformly distributed about the surface of the terminal. The amount of free charge is related to the self-capacitance of the charge terminal $T_1$.

For example, the capacitance of a spherical terminal can be expressed as a function of physical height above the ground plane. The capacitance of a sphere at a physical height of h above a perfect ground is given by $$C_{elevated\ sphere} = 4\pi\varepsilon_o a(1+M+M^2+M^3+2M^4+3M^5+\ldots), \quad (24)$$

where the diameter of the sphere is 2a, and where M=a/2h with h being the height of the spherical terminal. As can be seen, an increase in the terminal height h reduces the capacitance C of the charge terminal. It can be shown that for elevations of the charge terminal $T_1$ that are at a height of about four times the diameter (4D=8a) or greater, the charge distribution is approximately uniform about the spherical terminal, which can improve the coupling into the guided surface waveguide mode.

In the case of a sufficiently isolated terminal, the self-capacitance of a conductive sphere can be approximated by $C=4\pi\varepsilon_o a$, where a is the radius of the sphere in meters, and the self-capacitance of a disk can be approximated by $C=8\varepsilon_o a$, where a is the radius of the disk in meters. The charge terminal $T_1$ can include any shape such as a sphere, a disk, a cylinder, a cone, a torus, a hood, one or more rings, or any other randomized shape or combination of shapes. An equivalent spherical diameter can be determined and used for positioning of the charge terminal $T_1$.

This may be further understood with reference to the example of FIG. 3, where the charge terminal $T_1$ is elevated at a physical height of $h_p=H_1$ above the lossy conducting medium 203. To reduce the effects of the "bound" charge, the charge terminal $T_1$ can be positioned at a physical height that is at least four times the spherical diameter (or equivalent spherical diameter) of the charge terminal $T_1$ to reduce the bounded charge effects.

Figure 5A:
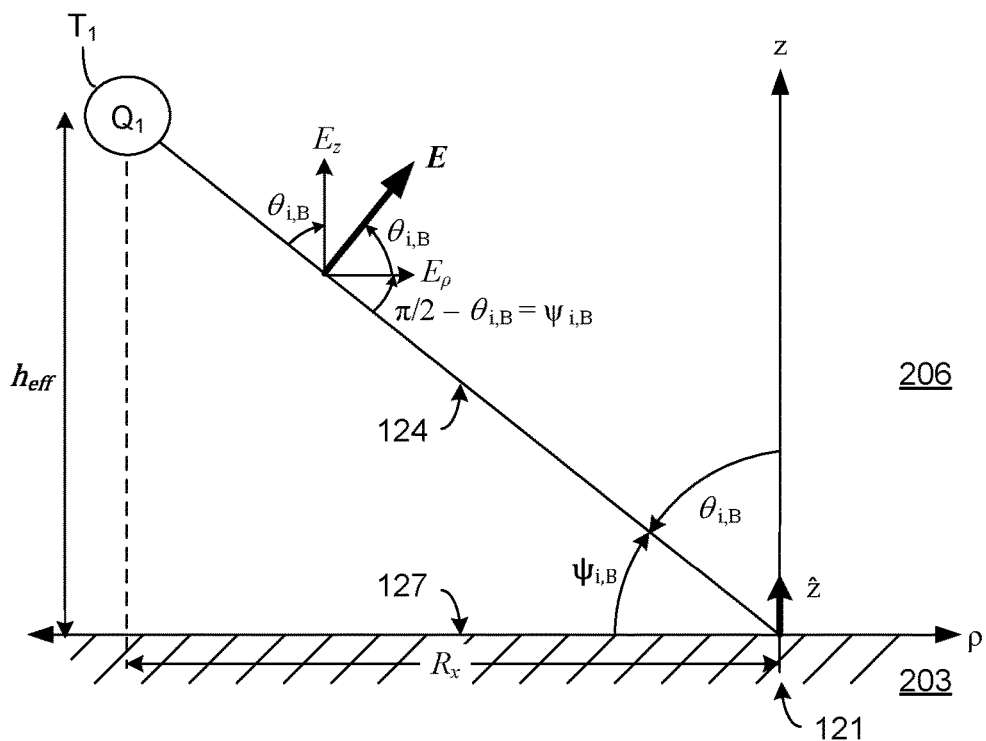
FIGS. 5A and 5B are drawings that illustrate a complex angle of incidence of an electric field synthesized by a guided surface waveguide probe according to various embodiments of the present disclosure.

Referring next to FIG. 5A, shown is a ray optics interpretation of the electric field produced by the elevated charge $Q_1$ on charge terminal $T_1$ of FIG. 3. As in optics, minimizing the reflection of the incident electric field can improve and/or maximize the energy coupled into the guided surface waveguide mode of the lossy conducting medium 203. For an electric field ($E_\parallel$) that is polarized parallel to the plane of incidence (not the boundary interface), the amount of reflection of the incident electric field may be determined using the Fresnel reflection coefficient, which can be expressed as $$\Gamma_\parallel(\theta_i) = \frac{E_{\parallel,R}}{E_{\parallel,i}} = \frac{\sqrt{(\varepsilon_r - jx) - \sin^2\theta_i} - (\varepsilon_r - jx)\cos\theta_i}{\sqrt{(\varepsilon_r - jx) - \sin^2\theta_i} + (\varepsilon_r - jx)\cos\theta_i}, \quad (25)$$

where $\theta_i$ is the conventional angle of incidence measured with respect to the surface normal.

In the example of FIG. 5A, the ray optic interpretation shows the incident field polarized parallel to the plane of incidence having an angle of incidence of $\theta_i$, which is measured with respect to the surface normal ($\hat{z}$). There will be no reflection of the incident electric field when $\Gamma_\parallel(\theta_i)=0$ and thus the incident electric field will be completely coupled into a guided surface waveguide mode along the surface of the lossy conducting medium 203. It can be seen that the numerator of Equation (25) goes to zero when the angle of incidence is $$\theta_i = \arctan(\sqrt{\varepsilon_r - jx}) = \theta_{i,B}, \quad (26)$$

where $x=\sigma/\omega\varepsilon_o$. This complex angle of incidence ($\theta_{i,B}$) is referred to as the Brewster angle. Referring back to Equation (22), it can be seen that the same complex Brewster angle ($\theta_{i,B}$) relationship is present in both Equations (22) and (26).

As illustrated in FIG. 5A, the electric field vector E can be depicted as an incoming non-uniform plane wave, polarized parallel to the plane of incidence. The electric field vector E can be created from independent horizontal and vertical components as $$\vec{E}(\theta i) = E_\rho \hat{\rho} + E_z \hat{z}. \quad (27)$$

Geometrically, the illustration in FIG. 5A suggests that the electric field vector E can be given by $$E_\rho(\rho, z) = E(\rho, z)\cos\theta_i, \text{ and} \quad (28a)$$

$$E_z(\rho, z) = E(\rho, z)\cos\left(\frac{\pi}{2} - \theta_i\right) = E(\rho, z)\sin\theta_i, \quad (28b)$$

which means that the field ratio is $$\frac{E_\rho}{E_z} = \frac{1}{\tan\theta_i} = \tan\psi_i. \quad (29)$$

Figure 5B:
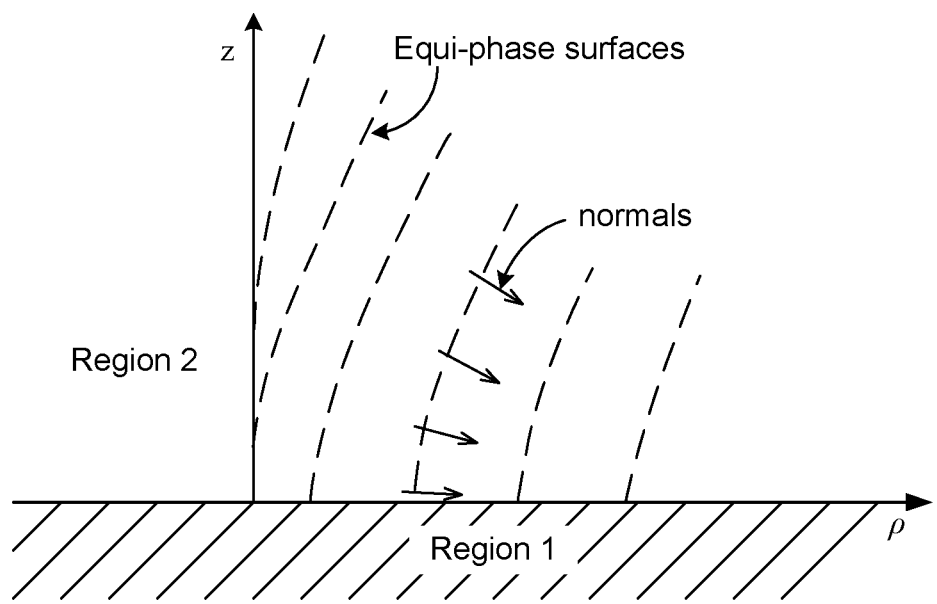

A generalized parameter W, called "wave tilt," is noted herein as the ratio of the horizontal electric field component to the vertical electric field component given by $$W = \frac{E_\rho}{E_z} = |W|e^{j\Psi}, \text{ or} \tag{30a}$$

$$\frac{1}{W} = \frac{E_z}{E_\rho} = \tan\theta_i = \frac{1}{|W|}e^{-j\Psi}, \tag{30b}$$

which is complex and has both magnitude and phase. For an electromagnetic wave in Region 2, the wave tilt angle (Ψ) is equal to the angle between the normal of the wave-front at the boundary interface with Region 1 and the tangent to the boundary interface. This may be easier to see in FIG. 5B, which illustrates equi-phase surfaces of an electromagnetic wave and their normals for a radial cylindrical guided surface wave. At the boundary interface (z=0) with a perfect conductor, the wave-front normal is parallel to the tangent of the boundary interface, resulting in W=0. However, in the case of a lossy dielectric, a wave tilt W exists because the wave-front normal is not parallel with the tangent of the boundary interface at z=0.

Applying Equation (30b) to a guided surface wave gives $$\tan\theta_{i,B} = \frac{E_z}{E_\rho} = \frac{u_2}{\gamma} = \sqrt{\varepsilon_r - jx} = n = \frac{1}{W} = \frac{1}{|W|}e^{-j\Psi}. \tag{31}$$

With the angle of incidence equal to the complex Brewster angle ($\theta_{i,B}$), the Fresnel reflection coefficient of Equation (25) vanishes, as shown by $$\Gamma_\parallel(\theta_{i,B}) = \left.\frac{\sqrt{(\varepsilon_r - jx) - \sin^2\theta_i} - (\varepsilon_r - jx)\cos\theta_i}{\sqrt{(\varepsilon_r - jx) - \sin^2\theta_i} + (\varepsilon_r - jx)\cos\theta_i}\right|_{\theta_i=\theta_{i,B}} = 0. \tag{32}$$

By adjusting the complex field ratio of Equation (22), an incident field can be synthesized to be incident at a complex angle at which the reflection is reduced or eliminated. Establishing this ratio as $n=\sqrt{\varepsilon_r-jx}$ results in the synthesized electric field being incident at the complex Brewster angle, making the reflections vanish.

The concept of an electrical effective height can provide further insight into synthesizing an electric field with a complex angle of incidence with a guided surface waveguide probe 200. The electrical effective height ($h_{eff}$) has been defined as $$h_{eff} = \frac{1}{I_0}\int_0^{h_p} I(z)\,dz \tag{33}$$

for a monopole with a physical height (or length) of $h_p$. Since the expression depends upon the magnitude and phase of the source distribution along the structure, the effective height (or length) is complex in general. The integration of the distributed current I(z) of the structure is performed over the physical height of the structure ($h_p$), and normalized to the ground current ($I_0$) flowing upward through the base (or input) of the structure. The distributed current along the structure can be expressed by $$I(z)=I_C\cos(\beta_0 z), \tag{34}$$

where $\beta_0$ is the propagation factor for current propagating on the structure. In the example of FIG. 3, $I_C$ is the current that is distributed along the vertical structure of the guided surface waveguide probe 200a.

For example, consider a feed network 209 that includes a low loss coil (e.g., a helical coil) at the bottom of the structure and a vertical feed line conductor connected between the coil and the charge terminal $T_1$. The phase delay due to the coil (or helical delay line) is $\theta_c=\beta_p l_C$, with a physical length of $l_C$ and a propagation factor of $$\beta_p = \frac{2\pi}{\lambda_p} = \frac{2\pi}{V_f\lambda_0}, \tag{35}$$

where $V_f$ is the velocity factor on the structure, $\lambda_0$ is the wavelength at the supplied frequency, and $\lambda_p$ is the propagation wavelength resulting from the velocity factor $V_f$. The phase delay is measured relative to the ground (stake) current $I_0$.

In addition, the spatial phase delay along the length $l_w$ of the vertical feed line conductor can be given by $\theta_y=\beta_w l_w$ where $\beta_w$ is the propagation phase constant for the vertical feed line conductor. In some implementations, the spatial phase delay may be approximated by $\theta_y=\beta_w h_p$, since the difference between the physical height $h_p$ of the guided surface waveguide probe 200a and the vertical feed line conductor length $l_w$ is much less than a wavelength at the supplied frequency ($\lambda_0$). As a result, the total phase delay through the coil and vertical feed line conductor is $\Phi=\theta_c+\theta_y$, and the current fed to the top of the coil from the bottom of the physical structure is $$I_C(\theta_c+\theta_y)=I_0 e^{j\Phi}, \tag{36}$$

with the total phase delay $\Phi$ measured relative to the ground (stake) current $I_0$. Consequently, the electrical effective height of a guided surface waveguide probe 200 can be approximated by $$h_{eff} = \frac{1}{I_0}\int_0^{h_p} I_0 e^{j\Phi}\cos(\beta_0 z)dz \cong h_p e^{j\Phi}, \tag{37}$$

for the case where the physical height $h_p\ll\lambda_0$. The complex effective height of a monopole, $h_{eff}=h_p$ at an angle (or phase shift) of $\Phi$, may be adjusted to cause the source fields to match a guided surface waveguide mode and cause a guided surface wave to be launched on the lossy conducting medium 203.

In the example of FIG. 5A, ray optics are used to illustrate the complex angle trigonometry of the incident electric field (E) having a complex Brewster angle of incidence ($\theta_{i,B}$) at the Hankel crossover distance ($R_x$) 121. Recall from Equation (26) that, for a lossy conducting medium, the Brewster angle is complex and specified by $$\tan\theta_{i,B} = \sqrt{\varepsilon_r - j\frac{\sigma}{\omega\varepsilon_0}} = n. \tag{38}$$

Electrically, the geometric parameters are related by the electrical effective height ($h_{eff}$) of the charge terminal $T_1$ by $$R_x\tan\psi_{i,B}=R_x\times W=h_{eff}=h_p e^{j\Phi}, \tag{39}$$

where $\psi_{i,B}=(\pi/2)-\theta_{i,B}$ is the Brewster angle measured from the surface of the lossy conducting medium. To couple into the guided surface waveguide mode, the wave tilt of the electric field at the Hankel crossover distance can be expressed as the ratio of the electrical effective height and the Hankel crossover distance $$\frac{h_{eff}}{R_x} = \tan\psi_{i,B} = W_{Rx}. \tag{40}$$

Since both the physical height ($h_p$) and the Hankel crossover distance ($R_x$) are real quantities, the angle ($\Psi$) of the desired guided surface wave tilt at the Hankel crossover distance ($R_x$) is equal to the phase ($\Phi$) of the complex effective height ($h_{eff}$). This implies that by varying the phase at the supply point of the coil, and thus the phase shift in Equation (37), the phase, $\Phi$, of the complex effective height can be manipulated to match the angle of the wave tilt, $\Psi$, of the guided surface waveguide mode at the Hankel crossover point 121: $\Phi=\Psi$.

In FIG. 5A, a right triangle is depicted having an adjacent side of length $R_x$ along the lossy conducting medium surface and a complex Brewster angle $\psi_{i,B}$ measured between a ray 124 extending between the Hankel crossover point 121 at $R_x$ and the center of the charge terminal $T_1$, and the lossy conducting medium surface 127 between the Hankel crossover point 121 and the charge terminal $T_1$. With the charge terminal $T_1$ positioned at physical height $h_p$ and excited with a charge having the appropriate phase delay $\Phi$, the resulting electric field is incident with the lossy conducting medium boundary interface at the Hankel crossover distance $R_x$, and at the Brewster angle. Under these conditions, the guided surface waveguide mode can be excited without reflection or substantially negligible reflection.

Figure 6:
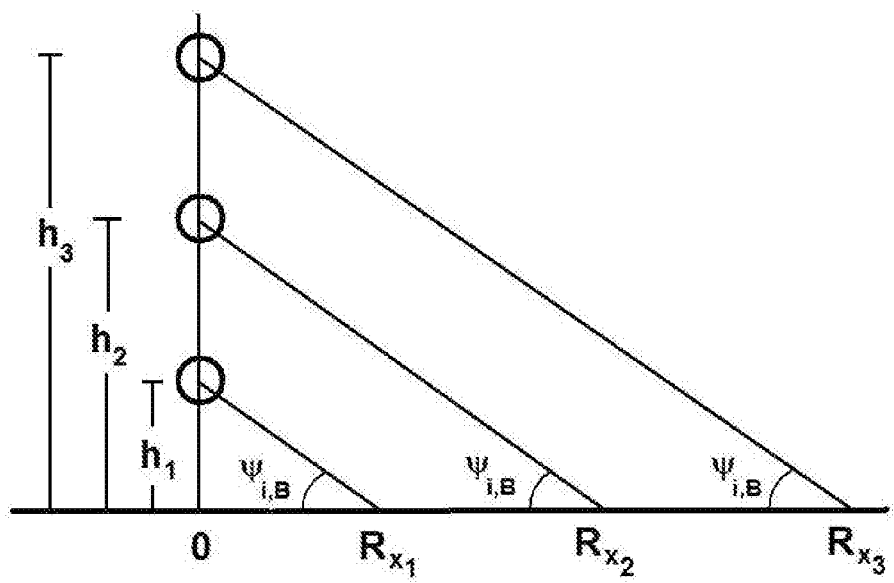
FIG. 6 is a graphical representation illustrating the effect of elevation of a charge terminal on the location where the electric field of FIG. 5A intersects with the lossy conducting medium at a Brewster angle according to various embodiments of the present disclosure.

If the physical height of the charge terminal $T_1$ is decreased without changing the phase shift $\Phi$ of the effective height ($h_{eff}$), the resulting electric field intersects the lossy conducting medium 203 at the Brewster angle at a reduced distance from the guided surface waveguide probe 200. FIG. 6 graphically illustrates the effect of decreasing the physical height of the charge terminal $T_1$ on the distance where the electric field is incident at the Brewster angle. As the height is decreased from $h_3$ through $h_2$ to $h_1$, the point where the electric field intersects with the lossy conducting medium (e.g., the Earth) at the Brewster angle moves closer to the charge terminal position. However, as Equation (39) indicates, the height $H_1$ (FIG. 3) of the charge terminal $T_1$ should be at or higher than the physical height ($h_p$) in order to excite the far-out component of the Hankel function. With the charge terminal $T_1$ positioned at or above the effective height ($h_{eff}$), the lossy conducting medium 203 can be illuminated at the Brewster angle of incidence ($\psi_{i,B}=(\pi/2)-\theta_{i,B}$) at or beyond the Hankel crossover distance ($R_x$) 121 as illustrated in FIG. 5A. To reduce or minimize the bound charge on the charge terminal $T_1$, the height should be at least four times the spherical diameter (or equivalent spherical diameter) of the charge terminal $T_1$ as mentioned above.

A guided surface waveguide probe 200 can be configured to establish an electric field having a wave tilt that corresponds to a wave illuminating the surface of the lossy conducting medium 203 at a complex Brewster angle, thereby exciting radial surface currents by substantially mode-matching to a guided surface wave mode at (or beyond) the Hankel crossover point 121 at $R_x$.

Figure 7:
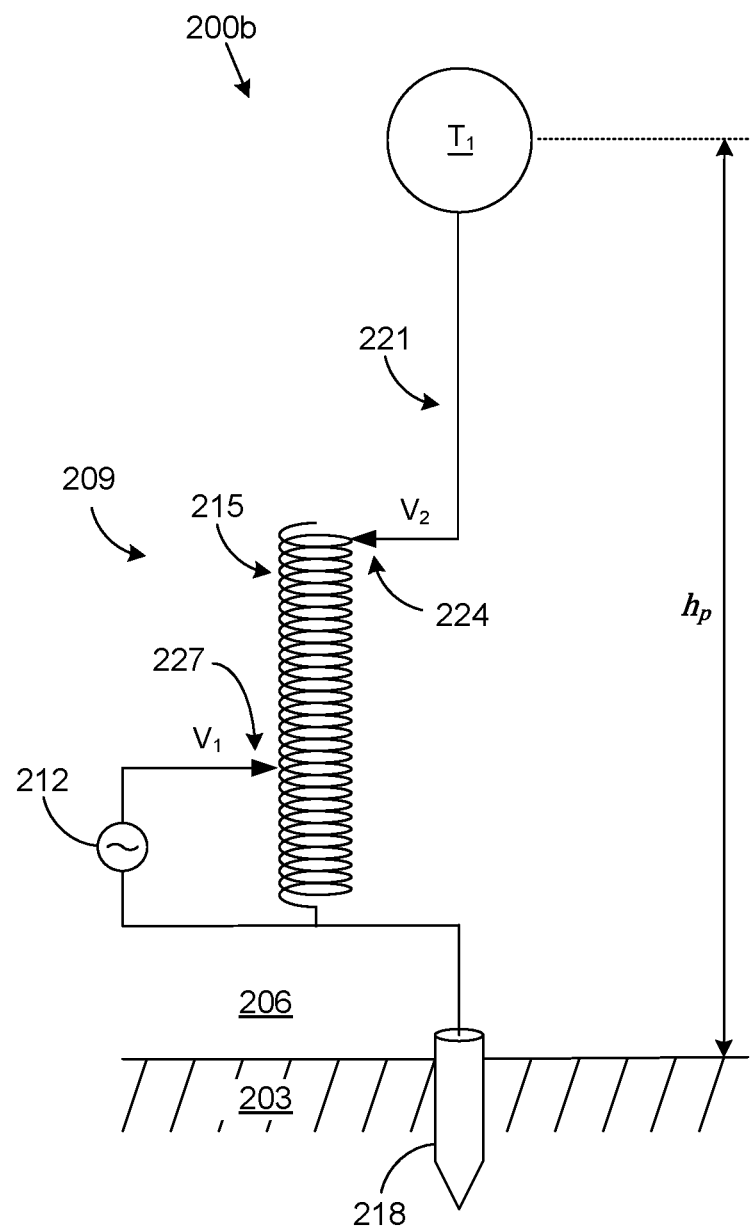
FIG. 7 is a graphical representation of an example of a guided surface waveguide probe according to various embodiments of the present disclosure.

Referring to FIG. 7, shown is a graphical representation of an example of a guided surface waveguide probe 200b that includes a charge terminal $T_1$. An AC source 212 acts as the excitation source for the charge terminal $T_1$, which is coupled to the guided surface waveguide probe 200b through a feed network 209 (FIG. 3) comprising a coil 215 such as, e.g., a helical coil. In other implementations, the AC source 212 can be inductively coupled to the coil 215 through a primary coil. In some embodiments, an impedance matching network may be included to improve and/or maximize coupling of the AC source 212 to the coil 215.

As shown in FIG. 7, the guided surface waveguide probe 200b can include the upper charge terminal $T_1$ (e.g., a sphere at height $h_p$) that is positioned along a vertical axis z that is substantially normal to the plane presented by the lossy conducting medium 203. A second medium 206 is located above the lossy conducting medium 203. The charge terminal $T_1$ has a self-capacitance $C_T$. During operation, charge $Q_1$ is imposed on the terminal $T_1$ depending on the voltage applied to the terminal $T_1$ at any given instant.

In the example of FIG. 7, the coil 215 is coupled to a ground stake 218 at a first end and to the charge terminal $T_1$ via a vertical feed line conductor 221. In some implementations, the coil connection to the charge terminal $T_1$ can be adjusted using a tap 224 of the coil 215 as shown in FIG. 7. The coil 215 can be energized at an operating frequency by the AC source 212 through a tap 227 at a lower portion of the coil 215. In other implementations, the AC source 212 can be inductively coupled to the coil 215 through a primary coil.

The construction and adjustment of the guided surface waveguide probe 200 is based upon various operating conditions, such as the transmission frequency, conditions of the lossy conducting medium (e.g., soil conductivity $\sigma$ and relative permittivity $\varepsilon_r$), and size of the charge terminal $T_1$. The index of refraction can be calculated from Equations (10) and (11) as $$n=\sqrt{\varepsilon_r - jx}, \tag{41}$$

where $x=\sigma/\omega\varepsilon_o$ with $\omega=2\pi f$. The conductivity $\sigma$ and relative permittivity $\varepsilon_r$ can be determined through test measurements of the lossy conducting medium 203. The complex Brewster angle ($\theta_{i,B}$) measured from the surface normal can also be determined from Equation (26) as $$\theta_{i,B}=\arctan(\sqrt{\varepsilon_r - jx}), \tag{42}$$

or measured from the surface as shown in FIG. 5A as $$\psi_{i,B} = \frac{\pi}{2} - \theta_{i,B}. \tag{43}$$

The wave tilt at the Hankel crossover distance ($W_{Rx}$) can also be found using Equation (40).

The Hankel crossover distance can also be found by equating the magnitudes of Equations (20b) and (21) for $-j\gamma\rho$, and solving for $R_x$ as illustrated by FIG. 4. The electrical effective height can then be determined from Equation (39) using the Hankel crossover distance and the complex Brewster angle as $$R_{eff}=h_p e^{j\Phi}=R_x \tan \psi_{i,B}. \tag{44}$$

As can be seen from Equation (44), the complex effective height ($h_{eff}$) includes a magnitude that is associated with the physical height ($h_p$) of the charge terminal $T_1$ and a phase delay ($\Phi$) that is to be associated with the angle ($\Psi$) of the wave tilt at the Hankel crossover distance ($R_x$). With these variables and the selected charge terminal $T_1$ configuration, it is possible to determine the configuration of a guided surface waveguide probe 200.

With the charge terminal $T_1$ positioned at or above the physical height ($h_p$), the feed network 209 (FIG. 3) and/or the vertical feed line connecting the feed network to the charge terminal $T_1$ can be adjusted to match the phase ($\Phi$) of the charge $Q_1$ on the charge terminal $T_1$ to the angle ($\Psi$) of the wave tilt (W). The size of the charge terminal $T_1$ can be chosen to provide a sufficiently large surface for the charge $Q_1$ imposed on the terminals. In general, it is desirable to make the charge terminal $T_1$ as large as practical. The size of the charge terminal $T_1$ should be large enough to avoid ionization of the surrounding air, which can result in electrical discharge or sparking around the charge terminal.

The phase delay $\theta_c$ of a helically-wound coil can be determined from Maxwell's equations as has been discussed by Corum, K. L. and J. F. Corum, "RF Coils, Helical Resonators and Voltage Magnification by Coherent Spatial Modes," *Microwave Review*, Vol. 7, No. 2, September 2001, pp. 36-45, which is incorporated herein by reference in its entirety. For a helical coil with H/D>1, the ratio of the velocity of propagation ($\upsilon$) of a wave along the coil's longitudinal axis to the speed of light (c), or the "velocity factor," is given by $$V_f = \frac{\upsilon}{c} = \frac{1}{\sqrt{1 + 20\left(\frac{D}{s}\right)^{2.5}\left(\frac{D}{\lambda_o}\right)^{0.5}}}, \qquad (45)$$

where H is the axial length of the solenoidal helix, D is the coil diameter, N is the number of turns of the coil, s=H/N is the turn-to-turn spacing (or helix pitch) of the coil, and $\lambda_o$ is the free-space wavelength. Based upon this relationship, the electrical length, or phase delay, of the helical coil is given by $$\theta_c = \beta_p H = \frac{2\pi}{\lambda_p} H = \frac{2\pi}{V_f \lambda_0} H. \qquad (46)$$

The principle is the same if the helix is wound spirally or is short and fat, but $V_f$ and $\theta_c$ are easier to obtain by experimental measurement. The expression for the characteristic (wave) impedance of a helical transmission line has also been derived as $$Z_c = \frac{60}{V_f}\left[\ln\left(\frac{V_f \lambda_0}{D}\right) - 1.027\right]. \qquad (47)$$

The spatial phase delay $\theta_y$ of the structure can be determined using the traveling wave phase delay of the vertical feed line conductor 221 (FIG. 7). The capacitance of a cylindrical vertical conductor above a prefect ground plane can be expressed as $$C_A = \frac{2\pi\varepsilon_o h_w}{\ln\left(\frac{h}{a}\right) - 1} \text{Farads}, \qquad (48)$$

where $h_w$ is the vertical length (or height) of the conductor and a is the radius (in mks units). As with the helical coil, the traveling wave phase delay of the vertical feed line conductor can be given by $$\theta_y = \beta_w h_w = \frac{2\pi}{\lambda_w} h_w = \frac{2\pi}{V_w \lambda_0} h_w, \qquad (49)$$

where $\beta_w$ is the propagation phase constant for the vertical feed line conductor, $h_w$ is the vertical length (or height) of the vertical feed line conductor, $V_w$ is the velocity factor on the wire, $\lambda_0$ is the wavelength at the supplied frequency, and $\lambda_w$ is the propagation wavelength resulting from the velocity factor $V_w$. For a uniform cylindrical conductor, the velocity factor is a constant with $V_w \approx 0.94$, or in a range from about 0.93 to about 0.98. If the mast is considered to be a uniform transmission line, its average characteristic impedance can be approximated by $$Z_w = \frac{60}{V_w}\left[\ln\left(\frac{h_w}{a}\right) - 1\right], \qquad (50)$$

where $V_w \approx 0.94$ for a uniform cylindrical conductor and a is the radius of the conductor. An alternative expression that has been employed in amateur radio literature for the characteristic impedance of a single-wire feed line can be given by $$Z_w = 138 \log\left(\frac{1.123 V_w \lambda_0}{2\pi a}\right). \qquad (51)$$

Equation (51) implies that $Z_w$ for a single-wire feeder varies with frequency. The phase delay can be determined based upon the capacitance and characteristic impedance.

With a charge terminal $T_1$ positioned over the lossy conducting medium 203 as shown in FIG. 3, the feed network 209 can be adjusted to excite the charge terminal $T_1$ with the phase shift ($\Phi$) of the complex effective height ($h_{eff}$) equal to the angle ($\Psi$) of the wave tilt at the Hankel crossover distance, or $\Phi=\Psi$. When this condition is met, the electric field produced by the charge oscillating $Q_1$ on the charge terminal $T_1$ is coupled into a guided surface waveguide mode traveling along the surface of a lossy conducting medium 203. For example, if the Brewster angle ($\theta_{i,B}$), the phase delay ($\theta_y$) associated with the vertical feed line conductor 221 (FIG. 7), and the configuration of the coil 215 (FIG. 7) are known, then the position of the tap 224 (FIG. 7) can be determined and adjusted to impose an oscillating charge $Q_1$ on the charge terminal $T_1$ with phase $\Phi=\Psi$. The position of the tap 224 may be adjusted to maximize coupling the traveling surface waves into the guided surface waveguide mode. Excess coil length beyond the position of the tap 224 can be removed to reduce the capacitive effects. The vertical wire height and/or the geometrical parameters of the helical coil may also be varied.

The coupling to the guided surface waveguide mode on the surface of the lossy conducting medium 203 can be improved and/or optimized by tuning the guided surface waveguide probe 200 for standing wave resonance with respect to a complex image plane associated with the charge $Q_1$ on the charge terminal $T_1$. By doing this, the performance of the guided surface waveguide probe 200 can be adjusted for increased and/or maximum voltage (and thus charge $Q_1$) on the charge terminal $T_1$. Referring back to FIG. 3, the effect of the lossy conducting medium 203 in Region 1 can be examined using image theory analysis.

Physically, an elevated charge $Q_1$ placed over a perfectly conducting plane attracts the free charge on the perfectly conducting plane, which then "piles up" in the region under the elevated charge $Q_1$. The resulting distribution of "bound" electricity on the perfectly conducting plane is similar to a bell-shaped curve. The superposition of the potential of the elevated charge $Q_1$, plus the potential of the induced "piled up" charge beneath it, forces a zero equipotential surface for the perfectly conducting plane. The boundary value problem solution that describes the fields in the region above the perfectly conducting plane may be obtained using the classical notion of image charges, where the field from the elevated charge is superimposed with the field from a corresponding "image" charge below the perfectly conducting plane.

This analysis may also be used with respect to a lossy conducting medium 203 by assuming the presence of an effective image charge $Q_1'$ beneath the guided surface waveguide probe 200. The effective image charge $Q_1'$ coincides with the charge $Q_1$ on the charge terminal $T_1$ about a conducting image ground plane 130, as illustrated in FIG. 3. However, the image charge $Q_1'$ is not merely located at some real depth and 180° out of phase with the primary source charge $Q_1$ on the charge terminal $T_1$, as they would be in the case of a perfect conductor. Rather, the lossy conducting medium 203 (e.g., a terrestrial medium) presents a phase shifted image. That is to say, the image charge $Q_1'$ is at a complex depth below the surface (or physical boundary) of the lossy conducting medium 203. For a discussion of complex image depth, reference is made to Wait, J. R., "Complex Image Theory—Revisited," *IEEE Antennas and Propagation Magazine*, Vol. 33, No. 4, August 1991, pp. 27-29, which is incorporated herein by reference in its entirety.

Instead of the image charge $Q_1'$ being at a depth that is equal to the physical height ($H_1$) of the charge $Q_1$, the conducting image ground plane 130 (representing a perfect conductor) is located at a complex depth of $z=-d/2$ and the image charge $Q_1'$ appears at a complex depth (i.e., the "depth" has both magnitude and phase), given by $-D_1=-(d/2+d/2+H_1)\neq H_1$. For vertically polarized sources over the Earth, $$d = \frac{2\sqrt{\gamma_e^2 + k_0^2}}{\gamma_e^2} \approx \frac{2}{\gamma_e} = d_r + jd_i = |d|\angle\zeta, \quad (52)$$

where $$\gamma_e^2 = j\omega\mu_1\sigma_1 - \omega^2\mu_1\varepsilon_1, \text{ and} \quad (53)$$

$$k_o = \omega\sqrt{\mu_o\varepsilon_o}, \quad (54)$$

as indicated in Equation (12). The complex spacing of the image charge, in turn, implies that the external field will experience extra phase shifts not encountered when the interface is either a dielectric or a perfect conductor. In the lossy conducting medium, the wave front normal is parallel to the tangent of the conducting image ground plane 130 at $z=-d/2$, and not at the boundary interface between Regions 1 and 2.

Consider the case illustrated in FIG. 8A where the lossy conducting medium 203 is a finitely conducting Earth 133 with a physical boundary 136. The finitely conducting Earth 133 may be replaced by a perfectly conducting image ground plane 139 as shown in FIG. 8B, which is located at a complex depth $z_1$ below the physical boundary 136. This equivalent representation exhibits the same impedance when looking down into the interface at the physical boundary 136. The equivalent representation of FIG. 8B can be modeled as an equivalent transmission line, as shown in FIG. 8C. The cross-section of the equivalent structure is represented as a (z-directed) end-loaded transmission line, with the impedance of the perfectly conducting image plane being a short circuit ($z_s=0$). The depth $z_1$ can be determined by equating the TEM wave impedance looking down at the Earth to an image ground plane impedance $z_{in}$ seen looking into the transmission line of FIG. 8C.

In the case of FIG. 8A, the propagation constant and wave intrinsic impedance in the upper region (air) 142 are $$\gamma_o = j\omega\sqrt{\mu_o\varepsilon_o} = 0 + j\beta_o, \text{ and} \quad (55)$$

$$z_o = \frac{j\omega\mu_o}{\gamma_o} = \sqrt{\frac{\mu_o}{\varepsilon_o}}. \quad (56)$$

In the lossy Earth 133, the propagation constant and wave intrinsic impedance are $$\gamma_e = \sqrt{j\omega\mu_1(\sigma_1 + j\omega\varepsilon_1)}, \text{ and} \quad (57)$$

$$Z_e = \frac{j\omega\mu_1}{\gamma_e}. \quad (58)$$

For normal incidence, the equivalent representation of FIG. 8B is equivalent to a TEM transmission line whose characteristic impedance is that of air ($z_o$), with propagation constant of $\gamma_o$, and whose length is $z_1$. As such, the image ground plane impedance $Z_{in}$ seen at the interface for the shorted transmission line of FIG. 8C is given by $$Z_{in} = Z_o \tan h(\gamma_o z_1). \quad (59)$$

Equating the image ground plane impedance $Z_{in}$ associated with the equivalent model of FIG. 8C to the normal incidence wave impedance of FIG. 8A and solving for $z_1$ gives the distance to a short circuit (the perfectly conducting image ground plane 139) as $$z_1 = \frac{1}{\gamma_o}\tanh^{-1}\left(\frac{Z_e}{Z_o}\right) = \frac{1}{\gamma_o}\tanh^{-1}\left(\frac{\gamma_o}{\gamma_e}\right) \approx \frac{1}{\gamma_e}, \quad (60)$$

where only the first term of the series expansion for the inverse hyperbolic tangent is considered for this approximation. Note that in the air region 142, the propagation constant is $\gamma_o=j\beta_o$, so $Z_{in}=jZ_o \tan \beta_o z_1$ (which is a purely imaginary quantity for a real $z_1$), but $z_e$ is a complex value if $\sigma\neq 0$. Therefore, $Z_{in}=Z_e$ only when $z_1$ is a complex distance.

Since the equivalent representation of FIG. 8B includes a perfectly conducting image ground plane 139, the image depth for a charge or current lying at the surface of the Earth (physical boundary 136) is equal to distance $z_1$ on the other side of the image ground plane 139, or $d=2\times z_1$ beneath the Earth's surface (which is located at z=0). Thus, the distance to the perfectly conducting image ground plane 139 can be approximated by $$d = 2z_1 \approx \frac{2}{\gamma_e}. \tag{61}$$

Additionally, the "image charge" will be "equal and opposite" to the real charge, so the potential of the perfectly conducting image ground plane 139 at depth $z_1=-d/2$ will be zero.

Figure 9A:
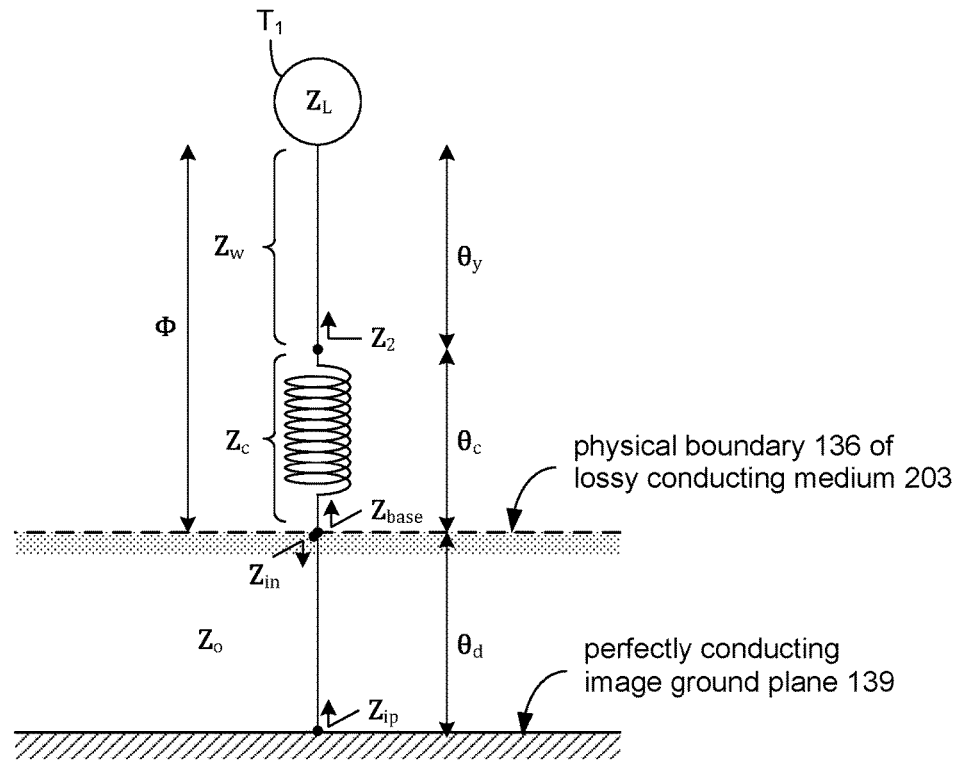
FIGS. 9A and 9B are graphical representations illustrating examples of single-wire transmission line and classic transmission line models of the equivalent image plane models of FIGS. 8B and 8C according to various embodiments of the present disclosure.

If a charge $Q_1$ is elevated a distance $H_1$ above the surface of the Earth as illustrated in FIG. 3, then the image charge $Q_1'$ resides at a complex distance of $D_1=d+H_1$ below the surface, or a complex distance of $d/2+H_1$ below the image ground plane 130. The guided surface waveguide probe 200b of FIG. 7 can be modeled as an equivalent single-wire transmission line image plane model that can be based upon the perfectly conducting image ground plane 139 of FIG. 8B. FIG. 9A shows an example of the equivalent single-wire transmission line image plane model, and FIG. 9B illustrates an example of the equivalent classic transmission line model, including the shorted transmission line of FIG. 8C.

Figure 9B:
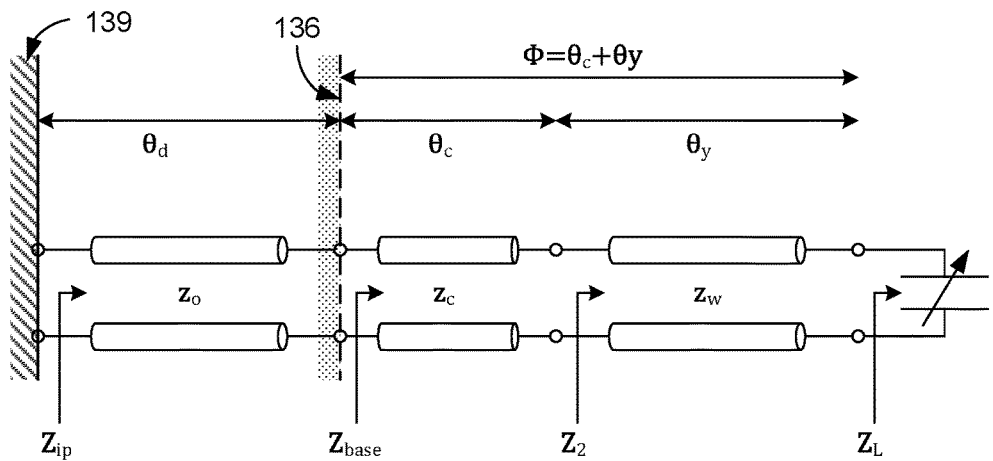

In the equivalent image plane models of FIGS. 9A and 9B, $\Phi=\theta_y+\theta_c$ is the traveling wave phase delay of the guided surface waveguide probe 200 referenced to Earth 133 (or the lossy conducting medium 203), $\theta_c=\beta_p H$ is the electrical length of the coil 215 (FIG. 7), of physical length H, expressed in degrees, $\theta_y=\beta_w h_w$ is the electrical length of the vertical feed line conductor 221 (FIG. 7), of physical length $h_w$, expressed in degrees, and $\theta_d=\beta_o d/2$ is the phase shift between the image ground plane 139 and the physical boundary 136 of the Earth 133 (or lossy conducting medium 203). In the example of FIGS. 9A and 9B, $Z_w$ is the characteristic impedance of the elevated vertical feed line conductor 221 in ohms, $Z_c$ is the characteristic impedance of the coil 215 in ohms, and $Z_o$ is the characteristic impedance of free space.

At the base of the guided surface waveguide probe 200, the impedance seen "looking up" into the structure is $Z_\uparrow=Z_{base}$. With a load impedance of:

$$Z_L = \frac{1}{j\omega C_T}, \tag{62}$$

where $C_T$ is the self-capacitance of the charge terminal $T_1$, the impedance seen "looking up" into the vertical feed line conductor 221 (FIG. 7) is given by:

$$Z_2 = Z_W \frac{Z_L + Z_w \tanh(j\beta_w h_w)}{Z_w + Z_L \tanh(j\beta_w h_w)} = Z_W \frac{Z_L + Z_w \tanh(j\theta_y)}{Z_w + Z_L \tanh(j\theta_y)}, \tag{63}$$

and the impedance seen "looking up" into the coil 215 (FIG. 7) is given by:

$$Z_{base} = Z_c \frac{Z_2 + Z_c \tanh(j\beta_p H)}{Z_c + Z_2 \tanh(j\beta_p H)} = Z_c \frac{Z_2 + Z_c \tanh(j\theta_c)}{Z_c + Z_2 \tanh(j\theta_c)}. \tag{64}$$

At the base of the guided surface waveguide probe 200, the impedance seen "looking down" into the lossy conducting medium 203 is $Z_\downarrow=Z_{in}$, which is given by:

$$Z_{in} = Z_o \frac{Z_s + Z_o \tanh[j\beta_o(d/2)]}{Z_o + Z_s \tanh[j\beta_o(d/2)]} = Z_o \tanh(j\theta_d), \tag{65}$$

where $Z_s \neq 0$.

Neglecting losses, the equivalent image plane model can be tuned to resonance when $Z_\downarrow+Z_\uparrow=0$ at the physical boundary 136. Or, in the low loss case, $X_\downarrow+X_\uparrow=0$ at the physical boundary 136, where X is the corresponding reactive component. Thus, the impedance at the physical boundary 136 "looking up" into the guided surface waveguide probe 200 is the conjugate of the impedance at the physical boundary 136 "looking down" into the lossy conducting medium 203. By adjusting the load impedance $Z_L$ of the charge terminal $T_1$ while maintaining the traveling wave phase delay $\Phi$ equal to the angle of the media's wave tilt $\Psi$, so that $\Phi=\Psi$, which improves and/or maximizes coupling of the probe's electric field to a guided surface waveguide mode along the surface of the lossy conducting medium 203 (e.g., Earth), the equivalent image plane models of FIGS. 9A and 9B can be tuned to resonance with respect to the image ground plane 139. In this way, the impedance of the equivalent complex image plane model is purely resistive, which maintains a superposed standing wave on the probe structure that maximizes the voltage and elevated charge on terminal $T_1$, and by equations (1)-(3) and (16) maximizes the propagating surface wave.

It follows from the Hankel solutions, that the guided surface wave excited by the guided surface waveguide probe 200 is an outward propagating traveling wave. The source distribution along the feed network 209 between the charge terminal $T_1$ and the ground stake 218 of the guided surface waveguide probe 200 (FIGS. 3 and 7) is actually composed of a superposition of a traveling wave plus a standing wave on the structure. With the charge terminal $T_1$ positioned at or above the physical height $h_p$, the phase delay of the traveling wave moving through the feed network 209 is matched to the angle of the wave tilt associated with the lossy conducting medium 203. This mode-matching allows the traveling wave to be launched along the lossy conducting medium 203. Once the phase delay has been established for the traveling wave, the load impedance $Z_L$ of the charge terminal $T_1$ is adjusted to bring the probe structure into standing wave resonance with respect to the image ground plane (130 of FIG. 3 or 139 of FIG. 8), which is at a complex depth of $-d/2$. In that case, the impedance seen from the image ground plane has zero reactance and the charge on the charge terminal $T_1$ is maximized.

The distinction between the traveling wave phenomenon and standing wave phenomena is that (1) the phase delay of traveling waves ($\theta=\beta d$) on a section of transmission line of length d (sometimes called a "delay line") is due to propagation time delays; whereas (2) the position-dependent phase of standing waves (which are composed of forward and backward propagating waves) depends on both the line length propagation time delay and impedance transitions at interfaces between line sections of different characteristic impedances. In addition to the phase delay that arises due to the physical length of a section of transmission line operating in sinusoidal steady-state, there is an extra reflection coefficient phase at impedance discontinuities that is due to the ratio of $Z_{oa}/Z_{ob}$, where $Z_{oa}$ and $Z_{ob}$ are the characteristic impedances of two sections of a transmission line such as, e.g., a helical coil section of characteristic impedance $Z_{oa}=Z_c$ (FIG. 9B) and a straight section of vertical feed line conductor of characteristic impedance $Z_{ob}=Z_w$ (FIG. 9B).

As a result of this phenomenon, two relatively short transmission line sections of widely differing characteristic impedance may be used to provide a very large phase shift. For example, a probe structure composed of two sections of transmission line, one of low impedance and one of high impedance, together totaling a physical length of, say, 0.05λ, may be fabricated to provide a phase shift of 90° which is equivalent to a 0.25λ resonance. This is due to the large jump in characteristic impedances. In this way, a physically short probe structure can be electrically longer than the two physical lengths combined. This is illustrated in FIGS. 9A and 9B, where the discontinuities in the impedance ratios provide large jumps in phase. The impedance discontinuity provides a substantial phase shift where the sections are joined together.

Figure 10:
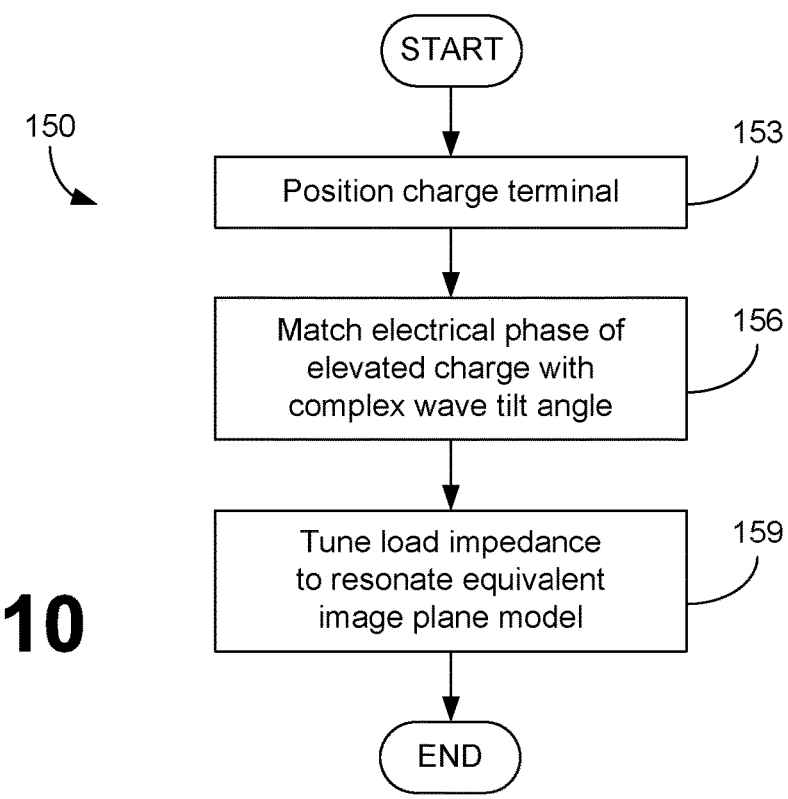
FIG. 10 is a flow chart illustrating an example of adjusting a guided surface waveguide probe of FIGS. 3 and 7 to launch a guided surface wave along the surface of a lossy conducting medium according to various embodiments of the present disclosure.

Referring to FIG. 10, shown is a flow chart 150 illustrating an example of adjusting a guided surface waveguide probe 200 (FIGS. 3 and 7) to substantially mode-match to a guided surface waveguide mode on the surface of the lossy conducting medium, which launches a guided surface traveling wave along the surface of a lossy conducting medium 203 (FIG. 3). Beginning with 153, the charge terminal $T_1$ of the guided surface waveguide probe 200 is positioned at a defined height above a lossy conducting medium 203. Utilizing the characteristics of the lossy conducting medium 203 and the operating frequency of the guided surface waveguide probe 200, the Hankel crossover distance can also be found by equating the magnitudes of Equations (20b) and (21) for −jγρ, and solving for $R_x$ as illustrated by FIG. 4. The complex index of refraction (n) can be determined using Equation (41), and the complex Brewster angle ($\theta_{i,B}$) can then be determined from Equation (42). The physical height ($h_p$) of the charge terminal $T_1$ can then be determined from Equation (44). The charge terminal $T_1$ should be at or higher than the physical height ($h_p$) in order to excite the far-out component of the Hankel function. This height relationship is initially considered when launching surface waves. To reduce or minimize the bound charge on the charge terminal $T_1$, the height should be at least four times the spherical diameter (or equivalent spherical diameter) of the charge terminal $T_1$.

At 156, the electrical phase delay Φ of the elevated charge $Q_1$ on the charge terminal $T_1$ is matched to the complex wave tilt angle Ψ. The phase delay ($\theta_c$) of the helical coil and/or the phase delay ($\theta_y$) of the vertical feed line conductor can be adjusted to make Φ equal to the angle (Ψ) of the wave tilt (W). Based on Equation (31), the angle (Ψ) of the wave tilt can be determined from:

$$W = \frac{E_\rho}{E_z} = \frac{1}{\tan\theta_{i,B}} = \frac{1}{n} = |W|e^{j\Psi}. \tag{66}$$

The electrical phase Φ can then be matched to the angle of the wave tilt. This angular (or phase) relationship is next considered when launching surface waves. For example, the electrical phase delay $\Phi=\theta_c+\theta_y$ can be adjusted by varying the geometrical parameters of the coil 215 (FIG. 7) and/or the length (or height) of the vertical feed line conductor 221 (FIG. 7). By matching Φ=W, an electric field can be established at or beyond the Hankel crossover distance ($R_x$) with a complex Brewster angle at the boundary interface to excite the surface waveguide mode and launch a traveling wave along the lossy conducting medium 203.

Next at 159, the load impedance of the charge terminal $T_1$ is tuned to resonate the equivalent image plane model of the guided surface waveguide probe 200. The depth (d/2) of the conducting image ground plane 139 of FIGS. 9A and 9B (or 130 of FIG. 3) can be determined using Equations (52), (53) and (54) and the values of the lossy conducting medium 203 (e.g., the Earth), which can be measured. Using that depth, the phase shift ($\theta_d$) between the image ground plane 139 and the physical boundary 136 of the lossy conducting medium 203 can be determined using $\theta_d=\beta_o$ d/2. The impedance ($Z_{in}$) as seen "looking down" into the lossy conducting medium 203 can then be determined using Equation (65). This resonance relationship can be considered to maximize the launched surface waves.

Based upon the adjusted parameters of the coil 215 and the length of the vertical feed line conductor 221, the velocity factor, phase delay, and impedance of the coil 215 and vertical feed line conductor 221 can be determined using Equations (45) through (51). In addition, the self-capacitance ($C_T$) of the charge terminal $T_1$ can be determined using, e.g., Equation (24). The propagation factor ($\beta_p$) of the coil 215 can be determined using Equation (35) and the propagation phase constant ($\beta_w$) for the vertical feed line conductor 221 can be determined using Equation (49). Using the self-capacitance and the determined values of the coil 215 and vertical feed line conductor 221, the impedance ($Z_{base}$) of the guided surface waveguide probe 200 as seen "looking up" into the coil 215 can be determined using Equations (62), (63) and (64).

The equivalent image plane model of the guided surface waveguide probe 200 can be tuned to resonance by adjusting the load impedance $Z_L$ such that the reactance component $X_{base}$ of $Z_{base}$ cancels out the reactance component $X_{in}$ of $Z_{in}$, or $X_{base}+X_{in}=0$. Thus, the impedance at the physical boundary 136 "looking up" into the guided surface waveguide probe 200 is the conjugate of the impedance at the physical boundary 136 "looking down" into the lossy conducting medium 203. The load impedance $Z_L$ can be adjusted by varying the capacitance ($C_T$) of the charge terminal $T_1$ without changing the electrical phase delay $\Phi=\theta_c+\theta_y$ of the charge terminal $T_1$. An iterative approach may be taken to tune the load impedance $Z_L$ for resonance of the equivalent image plane model with respect to the conducting image ground plane 139 (or 130). In this way, the coupling of the electric field to a guided surface waveguide mode along the surface of the lossy conducting medium 203 (e.g., Earth) can be improved and/or maximized.

This may be better understood by illustrating the situation with a numerical example. Consider a guided surface waveguide probe 200 comprising a top-loaded vertical stub of physical height $h_p$ with a charge terminal $T_1$ at the top, where the charge terminal $T_1$ is excited through a helical coil and vertical feed line conductor at an operational frequency ($f_o$) of 1.85 MHz. With a height ($H_1$) of 16 feet and the lossy conducting medium 203 (e.g., Earth) having a relative permittivity of $\varepsilon_r=15$ and a conductivity of $\sigma_1=0.010$ mhos/m, several surface wave propagation parameters can be calculated for $f_o=1.850$ MHz. Under these conditions, the Hankel crossover distance can be found to be $R_x=54.5$ feet with a physical height of $h_p=5.5$ feet, which is well below the actual height of the charge terminal $T_1$. While a charge terminal height of $H_1=5.5$ feet could have been used, the taller probe structure reduced the bound capacitance, permitting a greater percentage of free charge on the charge terminal $T_1$ providing greater field strength and excitation of the traveling wave.

The wave length can be determined as:

$$\lambda_o = \frac{c}{f_o} = 162.162 \text{ meters,} \tag{67}$$

where c is the speed of light. The complex index of refraction is:

$$n = \sqrt{\varepsilon_r - jx} = 7.529 - j6.546, \tag{68}$$

from Equation (41), where $x = \sigma_1/\omega\varepsilon_o$ with $\omega = 2\pi f_o$, and the complex Brewster angle is:

$$\theta_{i,B} = \arctan(\sqrt{\varepsilon_r - jx}) = 85.6 - j3.744°. \tag{69}$$

from Equation (42). Using Equation (66), the wave tilt values can be determined to be:

$$W = \frac{1}{\tan\theta_{i,B}} = \frac{1}{n} = |W|e^{j\Psi} = 0.101 e^{j40.614°}. \tag{70}$$

Thus, the helical coil can be adjusted to match $\Phi = \Psi = 40.614°$

The velocity factor of the vertical feed line conductor (approximated as a uniform cylindrical conductor with a diameter of 0.27 inches) can be given as $V_w \approx 0.93$. Since $h_p \ll \lambda_o$, the propagation phase constant for the vertical feed line conductor can be approximated as:

$$\beta_w = \frac{2\pi}{\lambda_w} = \frac{2\pi}{V_w \lambda_0} = 0.042 \text{ m}^{-1}. \tag{71}$$

From Equation (49) the phase delay of the vertical feed line conductor is:

$$\theta_y = \beta_w h_w \approx \beta_w h_p = 11.640°. \tag{72}$$

Figure 11:
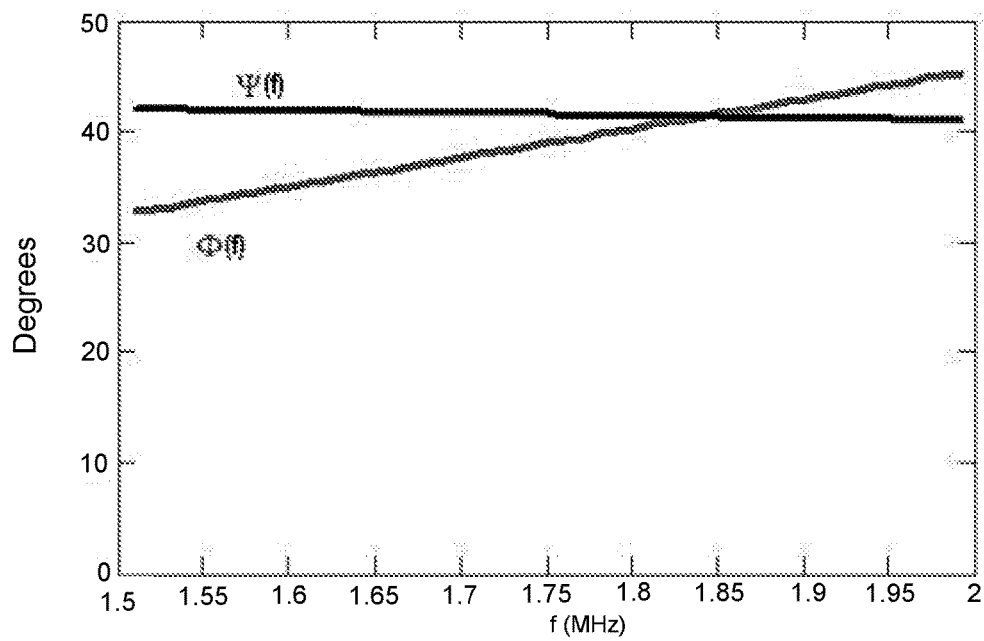
FIG. 11 is a plot illustrating an example of the relationship between a wave tilt angle and the phase delay of a guided surface waveguide probe of FIGS. 3 and 7 according to various embodiments of the present disclosure.

By adjusting the phase delay of the helical coil so that $\theta_c = 28.974° = 40.614° - 11.640°$, $\Phi$ will equal $\Psi$ to match the guided surface waveguide mode. To illustrate the relationship between $\Phi$ and $\Psi$, FIG. 11 shows a plot of both over a range of frequencies. As both $\Phi$ and $\Psi$ are frequency dependent, it can be seen that their respective curves cross over each other at approximately 1.85 MHz.

For a helical coil having a conductor diameter of 0.0881 inches, a coil diameter (D) of 30 inches and a turn-to-turn spacing (s) of 4 inches, the velocity factor for the coil can be determined using Equation (45) as:

$$V_f = \frac{1}{\sqrt{1 + 20\left(\frac{D}{s}\right)^{2.5}\left(\frac{D}{\lambda_o}\right)^{0.5}}} = 0.069, \tag{73}$$

and the propagation factor from Equation (35) is:

$$\beta_p = \frac{2\pi}{V_f \lambda_0} = 0.564 \text{ m}^{-1}. \tag{74}$$

With $\theta_c = 28.974°$, the axial length of the solenoidal helix (H) can be determined using Equation (46) such that:

$$H = \frac{\theta_c}{\beta_p} = 35.2732 \text{ inches.} \tag{75}$$

This height determines the location on the helical coil where the vertical feed line conductor is connected, resulting in a coil with 8.818 turns (N=H/s).

With the traveling wave phase delay of the coil and vertical feed line conductor adjusted to match the wave tilt angle ($\Phi = \theta_c + \theta_y = \Psi$), the load impedance ($Z_L$) of the charge terminal $T_1$ can be adjusted for standing wave resonance of the equivalent image plane model of the guided surface wave probe 200. From the measured permittivity, conductivity and permeability of the Earth, the radial propagation constant can be determined using Equation (57)

$$\gamma_e = \sqrt{j\omega\mu_1(\sigma_1 + j\omega\varepsilon_1)} = 0.25 + j0.292 \text{ m}^{-1}, \tag{76}$$

And the complex depth of the conducting image ground plane can be approximated from Equation (52) as:

$$d \approx \frac{2}{\gamma_e} = 3.364 + j\, 3.963 \text{ meters,} \tag{77}$$

with a corresponding phase shift between the conducting image ground plane and the physical boundary of the Earth given by:

$$\theta_d = \beta_o(d/2) = 4.015 - j4.73°. \tag{78}$$

Using Equation (65), the impedance seen "looking down" into the lossy conducting medium 203 (i.e., Earth) can be determined as:

$$Z_{in} = Z_o \tan h(j\theta_d) = R_{in} + jX_{in} = 31.191 + j26.27 \text{ ohms.} \tag{79}$$

By matching the reactive component ($X_{in}$) seen "looking down" into the lossy conducting medium 203 with the reactive component ($X_{base}$) seen "looking up" into the guided surface wave probe 200, the coupling into the guided surface waveguide mode may be maximized. This can be accomplished by adjusting the capacitance of the charge terminal $T_1$ without changing the traveling wave phase delays of the coil and vertical feed line conductor. For example, by adjusting the charge terminal capacitance ($C_T$) to 61.8126 pF, the load impedance from Equation (62) is:

$$Z_L = \frac{1}{j\omega C_T} = -j\, 1392 \text{ ohms,} \tag{80}$$

and the reactive components at the boundary are matched.

Using Equation (51), the impedance of the vertical feed line conductor (having a diameter (2a) of 0.27 inches) is given as $$Z_w = 138\log\left(\frac{1.123 V_w \lambda_0}{2\pi a}\right) = 537.534 \text{ ohms,} \tag{81}$$

and the impedance seen "looking up" into the vertical feed line conductor is given by Equation (63) as:

$$Z_2 = Z_W \frac{Z_L + Z_w \tanh(j\theta_y)}{Z_w + Z_L \tanh(j\theta_y)} = -j835.438 \text{ ohms.} \quad (82)$$

Using Equation (47), the characteristic impedance of the helical coil is given as $$Z_c = \frac{60}{V_f} \left[ \ell n \left( \frac{V_f \lambda_0}{D} \right) - 1.027 \right] = 1446 \text{ ohms,} \quad (83)$$

and the impedance seen "looking up" into the coil at the base is given by Equation (64) as:

$$Z_{base} = Z_c \frac{Z_2 + Z_c \tanh(j\theta_c)}{Z_c + Z_2 \tanh(j\theta_c)} = -j26.271 \text{ ohms.} \quad (84)$$

When compared to the solution of Equation (79), it can be seen that the reactive components are opposite and approximately equal, and thus are conjugates of each other. Thus, the impedance ($Z_{ip}$) seen "looking up" into the equivalent image plane model of FIGS. 9A and 9B from the perfectly conducting image ground plane is only resistive or $Z_{ip}$=R+j0.

When the electric fields produced by a guided surface waveguide probe 200 (FIG. 3) are established by matching the traveling wave phase delay of the feed network to the wave tilt angle and the probe structure is resonated with respect to the perfectly conducting image ground plane at complex depth z=−d/2, the fields are substantially mode-matched to a guided surface waveguide mode on the surface of the lossy conducting medium, a guided surface traveling wave is launched along the surface of the lossy conducting medium. As illustrated in FIG. 1, the guided field strength curve 103 of the guided electromagnetic field has a characteristic exponential decay of $e^{-\alpha d}/\sqrt{d}$ and exhibits a distinctive knee 109 on the log-log scale.

In summary, both analytically and experimentally, the traveling wave component on the structure of the guided surface waveguide probe 200 has a phase delay (Φ) at its upper terminal that matches the angle (Ψ) of the wave tilt of the surface traveling wave (Φ=Ψ). Under this condition, the surface waveguide may be considered to be "mode-matched". Furthermore, the resonant standing wave component on the structure of the guided surface waveguide probe 200 has a $V_{MAX}$ at the charge terminal $T_1$ and a $V_{MIN}$ down at the image plane 139 (FIG. 8B) where $Z_{ip}$=$R_{ip}$+j 0 at a complex depth of z=−d/2, not at the connection at the physical boundary 136 of the lossy conducting medium 203 (FIG. 8B). Lastly, the charge terminal $T_1$ is of sufficient height $H_1$ of FIG. 3 (h≥$R_x$ tan $\psi_{i,B}$) so that electromagnetic waves incident onto the lossy conducting medium 203 at the complex Brewster angle do so out at a distance (≥$R_x$) where the 1/√r term is predominant. Receive circuits can be utilized with one or more guided surface waveguide probes to facilitate wireless transmission and/or power delivery systems.

Referring back to FIG. 3, operation of a guided surface waveguide probe 200 may be controlled to adjust for variations in operational conditions associated with the guided surface waveguide probe 200. For example, an adaptive probe control system 230 can be used to control the feed network 209 and/or the charge terminal $T_1$ to control the operation of the guided surface waveguide probe 200. Operational conditions can include, but are not limited to, variations in the characteristics of the lossy conducting medium 203 (e.g., conductivity σ and relative permittivity $\varepsilon_r$), variations in field strength and/or variations in loading of the guided surface waveguide probe 200. As can be seen from Equations (31), (41) and (42), the index of refraction (n), the complex Brewster angle ($\theta_{i,B}$), and the wave tilt (|W|$e^{j\Psi}$) can be affected by changes in soil conductivity and permittivity resulting from, e.g., weather conditions.

Equipment such as, e.g., conductivity measurement probes, permittivity sensors, ground parameter meters, field meters, current monitors and/or load receivers can be used to monitor for changes in the operational conditions and provide information about current operational conditions to the adaptive probe control system 230. The probe control system 230 can then make one or more adjustments to the guided surface waveguide probe 200 to maintain specified operational conditions for the guided surface waveguide probe 200. For instance, as the moisture and temperature vary, the conductivity of the soil will also vary. Conductivity measurement probes and/or permittivity sensors may be located at multiple locations around the guided surface waveguide probe 200. Generally, it would be desirable to monitor the conductivity and/or permittivity at or about the Hankel crossover distance R, for the operational frequency. Conductivity measurement probes and/or permittivity sensors may be located at multiple locations (e.g., in each quadrant) around the guided surface waveguide probe 200.

The conductivity measurement probes and/or permittivity sensors can be configured to evaluate the conductivity and/or permittivity on a periodic basis and communicate the information to the probe control system 230. The information may be communicated to the probe control system 230 through a network such as, but not limited to, a LAN, WLAN, cellular network, or other appropriate wired or wireless communication network. Based upon the monitored conductivity and/or permittivity, the probe control system 230 may evaluate the variation in the index of refraction (n), the complex Brewster angle ($\theta_{i,B}$), and/or the wave tilt (|W|$e^{j\Psi}$) and adjust the guided surface waveguide probe 200 to maintain the phase delay (Φ) of the feed network 209 equal to the wave tilt angle (Ψ) and/or maintain resonance of the equivalent image plane model of the guided surface waveguide probe 200. This can be accomplished by adjusting, e.g., $\theta_y$, $\theta_c$ and/or $C_T$. For instance, the probe control system 230 can adjust the self-capacitance of the charge terminal $T_1$ and/or the phase delay ($\theta_y$, $\theta_c$) applied to the charge terminal $T_1$ to maintain the electrical launching efficiency of the guided surface wave at or near its maximum. For example, the self-capacitance of the charge terminal $T_1$ can be varied by changing the size of the terminal. The charge distribution can also be improved by increasing the size of the charge terminal $T_1$, which can reduce the chance of an electrical discharge from the charge terminal $T_1$. In other embodiments, the charge terminal $T_1$ can include a variable inductance that can be adjusted to change the load impedance $Z_L$. The phase applied to the charge terminal $T_1$ can be adjusted by varying the tap position on the coil 215 (FIG. 7), and/or by including a plurality of predefined taps along the coil 215 and switching between the different predefined tap locations to maximize the launching efficiency.

Field or field strength (FS) meters may also be distributed about the guided surface waveguide probe 200 to measure field strength of fields associated with the guided surface wave. The field or FS meters can be configured to detect the field strength and/or changes in the field strength (e.g., electric field strength) and communicate that information to the probe control system 230. The information may be communicated to the probe control system 230 through a network such as, but not limited to, a LAN, WLAN, cellular network, or other appropriate communication network. As the load and/or environmental conditions change or vary during operation, the guided surface waveguide probe 200 may be adjusted to maintain specified field strength(s) at the FS meter locations to ensure appropriate power transmission to the receivers and the loads they supply.

For example, the phase delay ($\Phi=\theta_y+\theta_c$) applied to the charge terminal $T_1$ can be adjusted to match the wave tilt angle ($\Psi$). By adjusting one or both phase delays, the guided surface waveguide probe 200 can be adjusted to ensure the wave tilt corresponds to the complex Brewster angle. This can be accomplished by adjusting a tap position on the coil 215 (FIG. 7) to change the phase delay supplied to the charge terminal $T_1$. The voltage level supplied to the charge terminal $T_1$ can also be increased or decreased to adjust the electric field strength. This may be accomplished by adjusting the output voltage of the excitation source 212 or by adjusting or reconfiguring the feed network 209. For instance, the position of the tap 227 (FIG. 7) for the AC source 212 can be adjusted to increase the voltage seen by the charge terminal $T_1$. Maintaining field strength levels within predefined ranges can improve coupling by the receivers, reduce ground current losses, and avoid interference with transmissions from other guided surface waveguide probes 200.

The probe control system 230 can be implemented with hardware, firmware, software executed by hardware, or a combination thereof. For example, the probe control system 230 can include processing circuitry including a processor and a memory, both of which can be coupled to a local interface such as, for example, a data bus with an accompanying control/address bus as can be appreciated by those with ordinary skill in the art. A probe control application may be executed by the processor to adjust the operation of the guided surface waveguide probe 200 based upon monitored conditions. The probe control system 230 can also include one or more network interfaces for communicating with the various monitoring devices. Communications can be through a network such as, but not limited to, a LAN, WLAN, cellular network, or other appropriate communication network. The probe control system 230 may comprise, for example, a computer system such as a server, desktop computer, laptop, or other system with like capability.

Referring back to the example of FIG. 5A, the complex angle trigonometry is shown for the ray optic interpretation of the incident electric field (E) of the charge terminal $T_1$ with a complex Brewster angle ($\theta_{i,B}$) at the Hankel crossover distance ($R_x$). Recall that, for a lossy conducting medium, the Brewster angle is complex and specified by equation (38). Electrically, the geometric parameters are related by the electrical effective height ($h_{eff}$) of the charge terminal $T_1$ by equation (39). Since both the physical height ($h_p$) and the Hankel crossover distance ($R_x$) are real quantities, the angle of the desired guided surface wave tilt at the Hankel crossover distance ($W_{Rx}$) is equal to the phase ($\Phi$) of the complex effective height ($h_{eff}$). With the charge terminal $T_1$ positioned at the physical height $h_p$ and excited with a charge having the appropriate phase $\Phi$, the resulting electric field is incident with the lossy conducting medium boundary interface at the Hankel crossover distance $R_x$, and at the Brewster angle. Under these conditions, the guided surface waveguide mode can be excited without reflection or substantially negligible reflection.

However, Equation (39) means that the physical height of the guided surface waveguide probe 200 can be relatively small. While this will excite the guided surface waveguide mode, this can result in an unduly large bound charge with little free charge. To compensate, the charge terminal $T_1$ can be raised to an appropriate elevation to increase the amount of free charge. As one example rule of thumb, the charge terminal $T_1$ can be positioned at an elevation of about 4-5 times (or more) the effective diameter of the charge terminal $T_1$. FIG. 6 illustrates the effect of raising the charge terminal $T_1$ above the physical height ($h_p$) shown in FIG. 5A. The increased elevation causes the distance at which the wave tilt is incident with the lossy conductive medium to move beyond the Hankel crossover point 121 (FIG. 5A). To improve coupling in the guided surface waveguide mode, and thus provide for a greater launching efficiency of the guided surface wave, a lower compensation terminal $T_2$ can be used to adjust the total effective height ($h_{TE}$) of the charge terminal $T_1$ such that the wave tilt at the Hankel crossover distance is at the Brewster angle.

Figure 12:
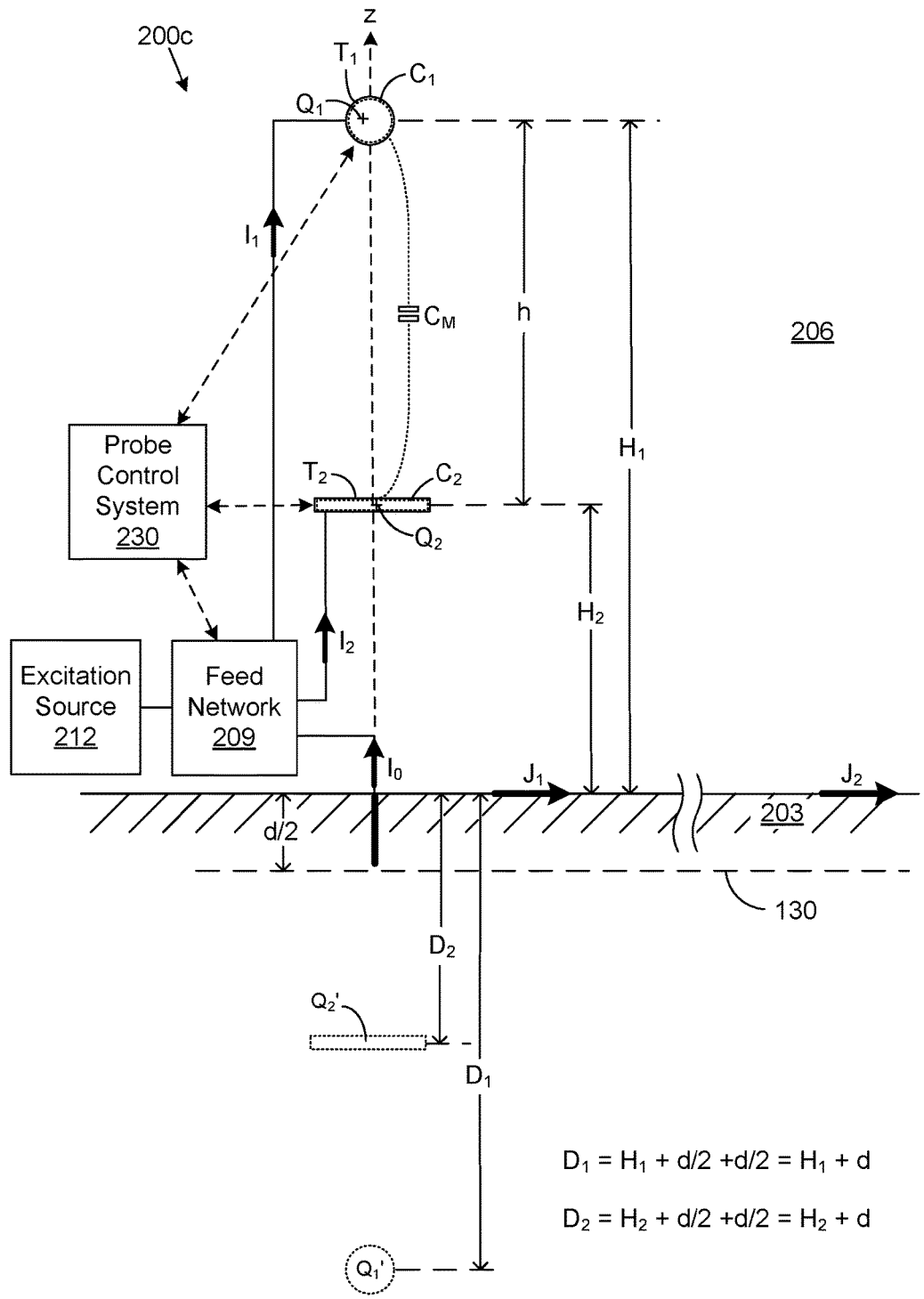
FIG. 12 is a drawing that illustrates an example of a guided surface waveguide probe according to various embodiments of the present disclosure.

Referring to FIG. 12, shown is an example of a guided surface waveguide probe 200c that includes an elevated charge terminal $T_1$ and a lower compensation terminal $T_2$ that are arranged along a vertical axis z that is normal to a plane presented by the lossy conducting medium 203. In this respect, the charge terminal $T_1$ is placed directly above the compensation terminal $T_2$ although it is possible that some other arrangement of two or more charge and/or compensation terminals $T_N$ can be used. The guided surface waveguide probe 200c is disposed above a lossy conducting medium 203 according to an embodiment of the present disclosure. The lossy conducting medium 203 makes up Region 1 with a second medium 206 that makes up Region 2 sharing a boundary interface with the lossy conducting medium 203.

The guided surface waveguide probe 200c includes a feed network 209 that couples an excitation source 212 to the charge terminal $T_1$ and the compensation terminal $T_2$. According to various embodiments, charges $Q_1$ and $Q_2$ can be imposed on the respective charge and compensation terminals $T_1$ and $T_2$, depending on the voltages applied to terminals $T_1$ and $T_2$ at any given instant. $I_1$ is the conduction current feeding the charge $Q_1$ on the charge terminal $T_1$ via the terminal lead, and $I_2$ is the conduction current feeding the charge $Q_2$ on the compensation terminal $T_2$ via the terminal lead.

According to the embodiment of FIG. 12, the charge terminal $T_1$ is positioned over the lossy conducting medium 203 at a physical height $H_1$, and the compensation terminal $T_2$ is positioned directly below $T_1$ along the vertical axis z at a physical height $H_2$, where $H_2$ is less than $H_1$. The height h of the transmission structure may be calculated as $h=H_1-H_2$. The charge terminal $T_1$ has an isolated (or self) capacitance $C_1$, and the compensation terminal $T_2$ has an isolated (or self) capacitance $C_2$. A mutual capacitance $C_M$ can also exist between the terminals $T_1$ and $T_2$ depending on the distance therebetween. During operation, charges $Q_1$ and $Q_2$ are imposed on the charge terminal $T_1$ and the compensation terminal $T_2$, respectively, depending on the voltages applied to the charge terminal $T_1$ and the compensation terminal $T_2$ at any given instant.

Figure 13:
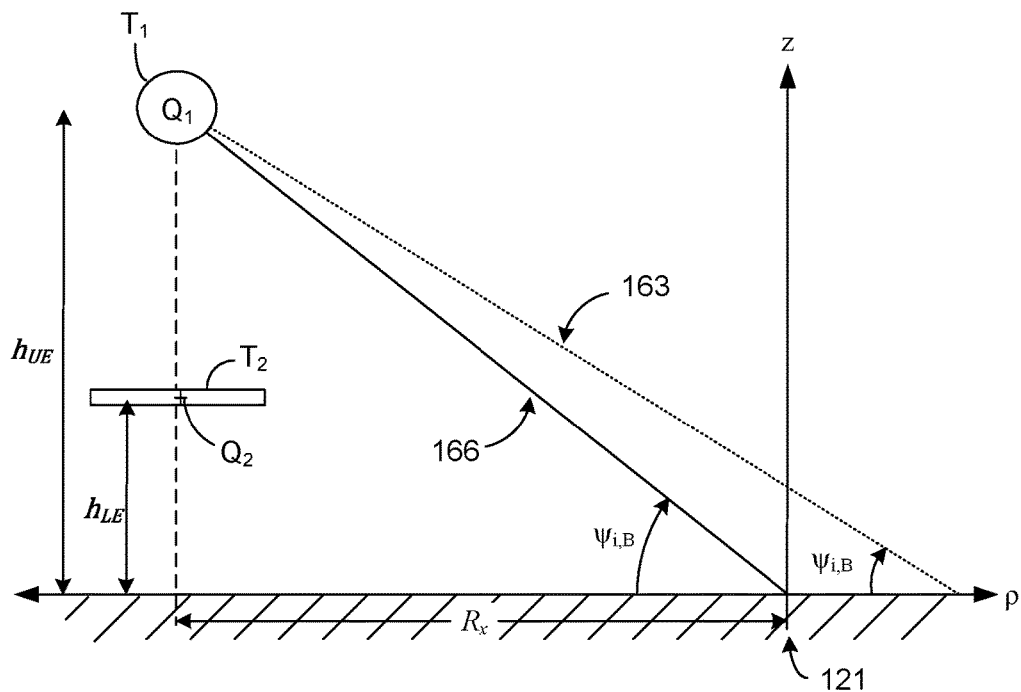
FIG. 13 is a graphical representation illustrating the incidence of a synthesized electric field at a complex Brewster angle to match the guided surface waveguide mode at the Hankel crossover distance according to various embodiments of the present disclosure.

Referring next to FIG. 13, shown is a ray optics interpretation of the effects produced by the elevated charge $Q_1$ on charge terminal $T_1$ and compensation terminal $T_2$ of FIG. 12. With the charge terminal $T_1$ elevated to a height where the ray intersects with the lossy conductive medium at the Brewster angle at a distance greater than the Hankel crossover point 121 as illustrated by line 163, the compensation terminal $T_2$ can be used to adjust $h_{TE}$ by compensating for the increased height. The effect of the compensation terminal $T_2$ is to reduce the electrical effective height of the guided surface waveguide probe (or effectively raise the lossy medium interface) such that the wave tilt at the Hankel crossover distance is at the Brewster angle as illustrated by line 166.

The total effective height can be written as the superposition of an upper effective height ($h_{UE}$) associated with the charge terminal $T_1$ and a lower effective height ($h_{LE}$) associated with the compensation terminal $T_2$ such that $$h_{TE}(h_{UE}+h_{LE}=h_p e^{j(\beta h_p+\Phi_U)}+h_d e^{j(\beta h_d+\Phi_L)}=R_x \times W, \quad (85)$$

where $\Phi_U$ is the phase delay applied to the upper charge terminal $T_1$, $\Phi_L$ is the phase delay applied to the lower compensation terminal $T_2$, $\beta=2\pi/\lambda_p$ is the propagation factor from Equation (35), $h_p$ is the physical height of the charge terminal $T_1$ and $h_d$ is the physical height of the compensation terminal $T_2$. If extra lead lengths are taken into consideration, they can be accounted for by adding the charge terminal lead length z to the physical height $h_p$ of the charge terminal $T_1$ and the compensation terminal lead length γ to the physical height $h_d$ of the compensation terminal $T_2$ as shown in $$h_{TE}=(h_p+z)e^{j(\beta(h_p+z)+\Phi_U)}+(h_d+y)e^{j(\beta(h_d+y)+\Phi_L)}=R_x \times W. \quad (86)$$

The lower effective height can be used to adjust the total effective height ($h_{TE}$) to equal the complex effective height ($h_{eff}$) of FIG. 5A.

Equations (85) or (86) can be used to determine the physical height of the lower disk of the compensation terminal $T_2$ and the phase angles to feed the terminals in order to obtain the desired wave tilt at the Hankel crossover distance. For example, Equation (86) can be rewritten as the phase shift applied to the charge terminal $T_1$ as a function of the compensation terminal height ($h_d$) to give $$\Phi_U(h_d) = -\beta(h_p+z) - j\ln\left(\frac{R_x \times W - (h_d+y)e^{j(\beta h_d+\beta y+\Phi_L)}}{(h_p+z)}\right). \quad (87)$$

To determine the positioning of the compensation terminal $T_2$, the relationships discussed above can be utilized. First, the total effective height ($h_{TE}$) is the superposition of the complex effective height ($h_{UE}$) of the upper charge terminal $T_1$ and the complex effective height ($h_{LE}$) of the lower compensation terminal $T_2$ as expressed in Equation (86). Next, the tangent of the angle of incidence can be expressed geometrically as $$\tan\psi_E = \frac{h_{TE}}{R_x}, \quad (88)$$

which is equal to the definition of the wave tilt, W. Finally, given the desired Hankel crossover distance $R_x$, the $h_{TE}$ can be adjusted to make the wave tilt of the incident ray match the complex Brewster angle at the Hankel crossover point 121. This can be accomplished by adjusting $h_p$, $\Phi_U$, and/or $h_d$.

Figure 14:
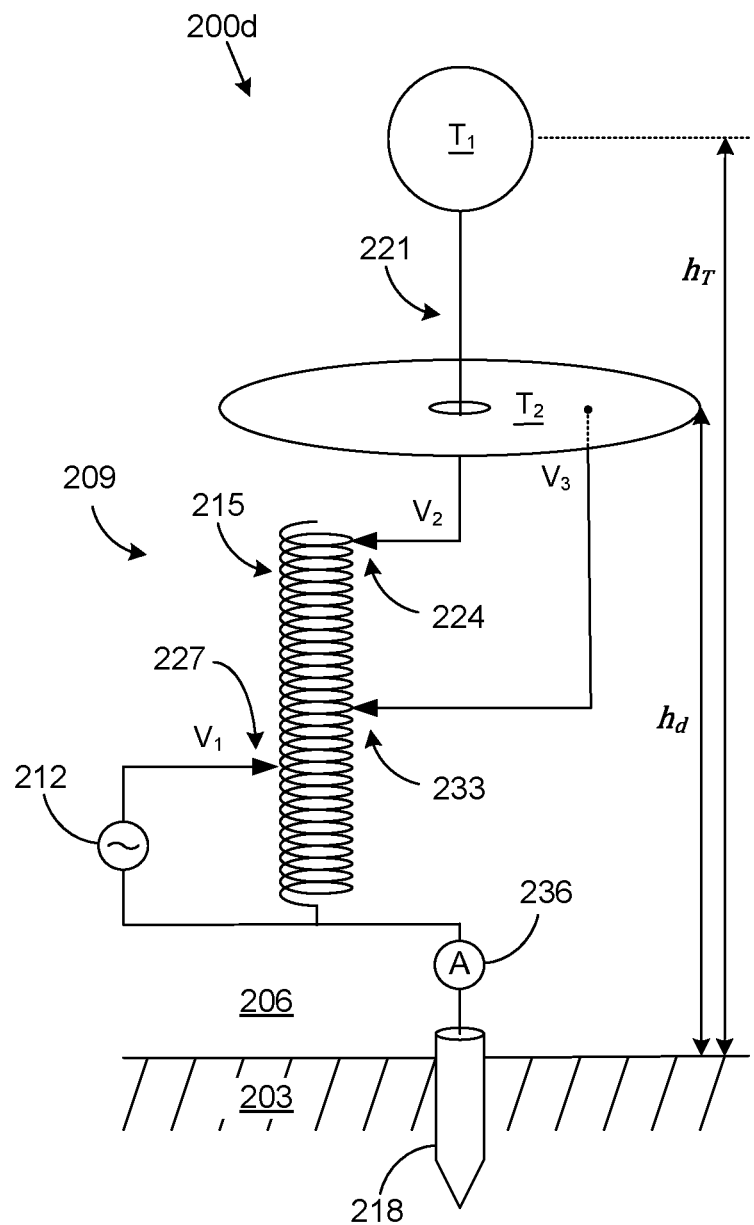
FIG. 14 is a graphical representation of an example of a guided surface waveguide probe of FIG. 12 according to various embodiments of the present disclosure.

These concepts may be better understood when discussed in the context of an example of a guided surface waveguide probe. Referring to FIG. 14, shown is a graphical representation of an example of a guided surface waveguide probe 200d including an upper charge terminal $T_1$ (e.g., a sphere at height $h_T$) and a lower compensation terminal $T_2$ (e.g., a disk at height $h_d$) that are positioned along a vertical axis z that is substantially normal to the plane presented by the lossy conducting medium 203. During operation, charges $Q_1$ and $Q_2$ are imposed on the charge and compensation terminals $T_1$ and $T_2$, respectively, depending on the voltages applied to the terminals $T_1$ and $T_2$ at any given instant.

An AC source 212 acts as the excitation source for the charge terminal $T_1$, which is coupled to the guided surface waveguide probe 200d through a feed network 209 comprising a coil 215 such as, e.g., a helical coil. The AC source 212 can be connected across a lower portion of the coil 215 through a tap 227, as shown in FIG. 14, or can be inductively coupled to the coil 215 by way of a primary coil. The coil 215 can be coupled to a ground stake 218 at a first end and the charge terminal $T_1$ at a second end. In some implementations, the connection to the charge terminal $T_1$ can be adjusted using a tap 224 at the second end of the coil 215. The compensation terminal $T_2$ is positioned above and substantially parallel with the lossy conducting medium 203 (e.g., the ground or Earth), and energized through a tap 233 coupled to the coil 215. An ammeter 236 located between the coil 215 and ground stake 218 can be used to provide an indication of the magnitude of the current flow ($I_0$) at the base of the guided surface waveguide probe. Alternatively, a current clamp may be used around the conductor coupled to the ground stake 218 to obtain an indication of the magnitude of the current flow ($I_0$).

In the example of FIG. 14, the coil 215 is coupled to a ground stake 218 at a first end and the charge terminal $T_1$ at a second end via a vertical feed line conductor 221. In some implementations, the connection to the charge terminal $T_1$ can be adjusted using a tap 224 at the second end of the coil 215 as shown in FIG. 14. The coil 215 can be energized at an operating frequency by the AC source 212 through a tap 227 at a lower portion of the coil 215. In other implementations, the AC source 212 can be inductively coupled to the coil 215 through a primary coil. The compensation terminal $T_2$ is energized through a tap 233 coupled to the coil 215. An ammeter 236 located between the coil 215 and ground stake 218 can be used to provide an indication of the magnitude of the current flow at the base of the guided surface waveguide probe 200d. Alternatively, a current clamp may be used around the conductor coupled to the ground stake 218 to obtain an indication of the magnitude of the current flow. The compensation terminal $T_2$ is positioned above and substantially parallel with the lossy conducting medium 203 (e.g., the ground).

In the example of FIG. 14, the connection to the charge terminal $T_1$ located on the coil 215 above the connection point of tap 233 for the compensation terminal $T_2$. Such an adjustment allows an increased voltage (and thus a higher charge $Q_1$) to be applied to the upper charge terminal $T_1$. In other embodiments, the connection points for the charge terminal $T_1$ and the compensation terminal $T_2$ can be reversed. It is possible to adjust the total effective height ($h_{TE}$) of the guided surface waveguide probe 200d to excite an electric field having a guided surface wave tilt at the Hankel crossover distance $R_x$. The Hankel crossover distance can also be found by equating the magnitudes of equations (20b) and (21) for $-j\gamma\rho$, and solving for $R_x$ as illustrated by FIG. 4. The index of refraction (n), the complex Brewster angle ($\theta_{i,B}$ and $\psi_{i,B}$), the wave tilt ($|W|e^{j\Psi}$) and the complex effective height ($h_{eff}=h_p e^{j\Phi}$) can be determined as described with respect to Equations (41)-(44) above.

With the selected charge terminal $T_1$ configuration, a spherical diameter (or the effective spherical diameter) can be determined. For example, if the charge terminal $T_1$ is not configured as a sphere, then the terminal configuration may be modeled as a spherical capacitance having an effective spherical diameter. The size of the charge terminal $T_1$ can be chosen to provide a sufficiently large surface for the charge $Q_1$ imposed on the terminals. In general, it is desirable to make the charge terminal $T_1$ as large as practical. The size of the charge terminal $T_1$ should be large enough to avoid ionization of the surrounding air, which can result in electrical discharge or sparking around the charge terminal. To reduce the amount of bound charge on the charge terminal $T_1$, the desired elevation to provide free charge on the charge terminal $T_1$ for launching a guided surface wave should be at least 4-5 times the effective spherical diameter above the lossy conductive medium (e.g., the Earth). The compensation terminal $T_2$ can be used to adjust the total effective height ($h_{TE}$) of the guided surface waveguide probe 200d to excite an electric field having a guided surface wave tilt at $R_x$. The compensation terminal $T_2$ can be positioned below the charge terminal $T_1$ at $h_d = h_T - h_p$, where $h_T$ is the total physical height of the charge terminal $T_1$. With the position of the compensation terminal $T_2$ fixed and the phase delay $\Phi_U$ applied to the upper charge terminal $T_1$, the phase delay $\Phi_L$ applied to the lower compensation terminal $T_2$ can be determined using the relationships of Equation (86), such that:

$$\Phi_U(h_d) = -\beta(h_d + y) - j\ln\left(\frac{R_x \times W - (h_p + z)e^{j(\beta h_p + \beta z + \Phi_L)}}{(h_d + y)}\right). \quad (89)$$

Figure 15A:
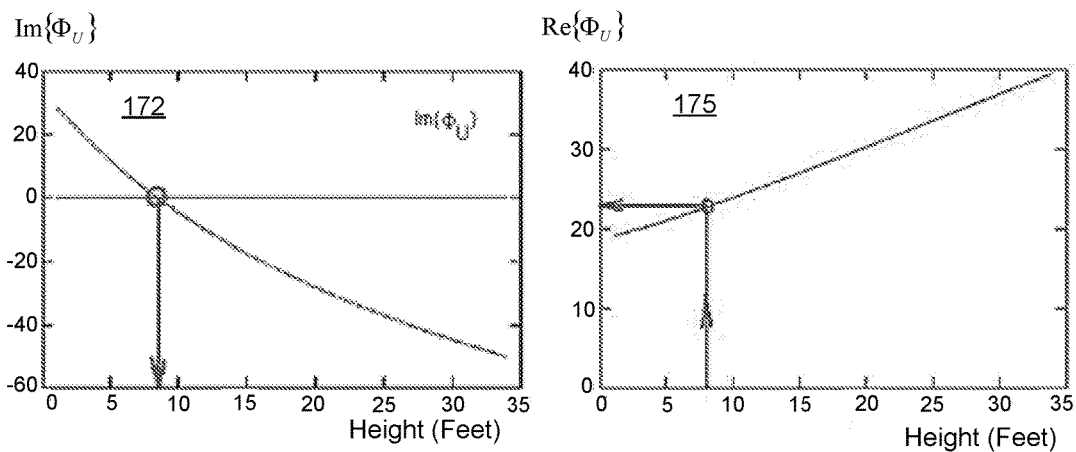
FIG. 15A includes plots of an example of the imaginary and real parts of a phase delay ($\Phi_U$) of a charge terminal $T_1$ of a guided surface waveguide probe according to various embodiments of the present disclosure.

In alternative embodiments, the compensation terminal $T_2$ can be positioned at a height $h_d$ where $\text{Im}\{\Phi_L\}=0$. This is graphically illustrated in FIG. 15A, which shows plots 172 and 175 of the imaginary and real parts of $\Phi_U$, respectively. The compensation terminal $T_2$ is positioned at a height $h_d$ where $\text{Im}\{\Phi_U\}=0$, as graphically illustrated in plot 172. At this fixed height, the coil phase $\Phi_U$ can be determined from $\text{Re}\{\Phi_U\}$, as graphically illustrated in plot 175.

Figure 15B:
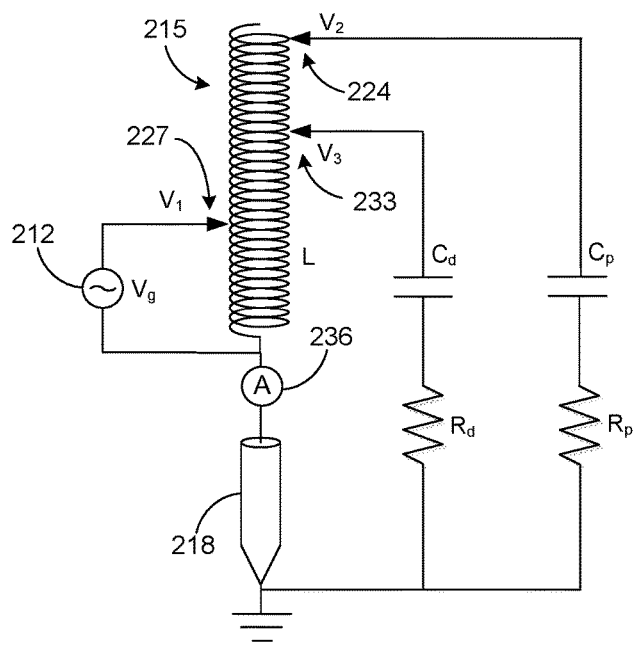
FIG. 15B is a schematic diagram of the guided surface waveguide probe of FIG. 14 according to various embodiments of the present disclosure.

With the AC source 212 coupled to the coil 215 (e.g., at the 50Ω point to maximize coupling), the position of tap 233 may be adjusted for parallel resonance of the compensation terminal $T_2$ with at least a portion of the coil at the frequency of operation. FIG. 15B shows a schematic diagram of the general electrical hookup of FIG. 14 in which $V_1$ is the voltage applied to the lower portion of the coil 215 from the AC source 212 through tap 227, $V_2$ is the voltage at tap 224 that is supplied to the upper charge terminal $T_1$, and $V_3$ is the voltage applied to the lower compensation terminal $T_2$ through tap 233. The resistances $R_p$ and $R_d$ represent the ground return resistances of the charge terminal $T_1$ and compensation terminal $T_2$, respectively. The charge and compensation terminals $T_1$ and $T_2$ may be configured as spheres, cylinders, toroids, rings, hoods, or any other combination of capacitive structures. The size of the charge and compensation terminals $T_1$ and $T_2$ can be chosen to provide a sufficiently large surface for the charges $Q_1$ and $Q_2$ imposed on the terminals. In general, it is desirable to make the charge terminal $T_1$ as large as practical. The size of the charge terminal $T_1$ should be large enough to avoid ionization of the surrounding air, which can result in electrical discharge or sparking around the charge terminal. The self-capacitance $C_p$ and $C_d$ of the charge and compensation terminals $T_1$ and $T_2$ respectively, can be determined using, for example, equation (24).

As can be seen in FIG. 15B, a resonant circuit is formed by at least a portion of the inductance of the coil 215, the self-capacitance $C_d$ of the compensation terminal $T_2$, and the ground return resistance $R_d$ associated with the compensation terminal $T_2$. The parallel resonance can be established by adjusting the voltage $V_3$ applied to the compensation terminal $T_2$ (e.g., by adjusting a tap 233 position on the coil 215) or by adjusting the height and/or size of the compensation terminal $T_2$ to adjust $C_d$. The position of the coil tap 233 can be adjusted for parallel resonance, which will result in the ground current through the ground stake 218 and through the ammeter 236 reaching a maximum point. After parallel resonance of the compensation terminal $T_2$ has been established, the position of the tap 227 for the AC source 212 can be adjusted to the 50Ω point on the coil 215.

Voltage $V_2$ from the coil 215 can be applied to the charge terminal $T_1$, and the position of tap 224 can be adjusted such that the phase ($\Phi$) of the total effective height ($h_{TE}$) approximately equals the angle of the guided surface wave tilt ($W_{Rx}$) at the Hankel crossover distance ($R_x$). The position of the coil tap 224 can be adjusted until this operating point is reached, which results in the ground current through the ammeter 236 increasing to a maximum. At this point, the resultant fields excited by the guided surface waveguide probe 200d are substantially mode-matched to a guided surface waveguide mode on the surface of the lossy conducting medium 203, resulting in the launching of a guided surface wave along the surface of the lossy conducting medium 203. This can be verified by measuring field strength along a radial extending from the guided surface waveguide probe 200.

Resonance of the circuit including the compensation terminal $T_2$ may change with the attachment of the charge terminal $T_1$ and/or with adjustment of the voltage applied to the charge terminal $T_1$ through tap 224. While adjusting the compensation terminal circuit for resonance aids the subsequent adjustment of the charge terminal connection, it is not necessary to establish the guided surface wave tilt ($W_{Rx}$) at the Hankel crossover distance ($R_x$). The system may be further adjusted to improve coupling by iteratively adjusting the position of the tap 227 for the AC source 212 to be at the 50Ω point on the coil 215 and adjusting the position of tap 233 to maximize the ground current through the ammeter 236. Resonance of the circuit including the compensation terminal $T_2$ may drift as the positions of taps 227 and 233 are adjusted, or when other components are attached to the coil 215.

In other implementations, the voltage $V_2$ from the coil 215 can be applied to the charge terminal $T_1$, and the position of tap 233 can be adjusted such that the phase ($\Phi$) of the total effective height ($h_{TE}$) approximately equals the angle ($\Psi$) of the guided surface wave tilt at $R_x$. The position of the coil tap 224 can be adjusted until the operating point is reached, resulting in the ground current through the ammeter 236 substantially reaching a maximum. The resultant fields are substantially mode-matched to a guided surface waveguide mode on the surface of the lossy conducting medium 203, and a guided surface wave is launched along the surface of the lossy conducting medium 203. This can be verified by measuring field strength along a radial extending from the guided surface waveguide probe 200. The system may be further adjusted to improve coupling by iteratively adjusting the position of the tap 227 for the AC source 212 to be at the 50Ω point on the coil 215 and adjusting the position of tap 224 and/or 233 to maximize the ground current through the ammeter 236.

Referring back to FIG. 12, operation of a guided surface waveguide probe 200 may be controlled to adjust for variations in operational conditions associated with the guided surface waveguide probe 200. For example, a probe control system 230 can be used to control the feed network 209 and/or positioning of the charge terminal $T_1$ and/or compensation terminal $T_2$ to control the operation of the guided surface waveguide probe 200. Operational conditions can include, but are not limited to, variations in the characteristics of the lossy conducting medium 203 (e.g., conductivity σ and relative permittivity $\varepsilon_r$), variations in field strength and/or variations in loading of the guided surface waveguide probe 200. As can be seen from Equations (41)-(44), the index of refraction (n), the complex Brewster angle ($\theta_{i,B}$ and $\psi_{i,B}$), the wave tilt ($|W|e^{j\Psi}$) and the complex effective height ($h_{eff}=h_p e^{j\Phi}$) can be affected by changes in soil conductivity and permittivity resulting from, e.g., weather conditions.

Equipment such as, e.g., conductivity measurement probes, permittivity sensors, ground parameter meters, field meters, current monitors and/or load receivers can be used to monitor for changes in the operational conditions and provide information about current operational conditions to the probe control system 230. The probe control system 230 can then make one or more adjustments to the guided surface waveguide probe 200 to maintain specified operational conditions for the guided surface waveguide probe 200. For instance, as the moisture and temperature vary, the conductivity of the soil will also vary. Conductivity measurement probes and/or permittivity sensors may be located at multiple locations around the guided surface waveguide probe 200. Generally, it would be desirable to monitor the conductivity and/or permittivity at or about the Hankel crossover distance R, for the operational frequency. Conductivity measurement probes and/or permittivity sensors may be located at multiple locations (e.g., in each quadrant) around the guided surface waveguide probe 200.

Figure 16:
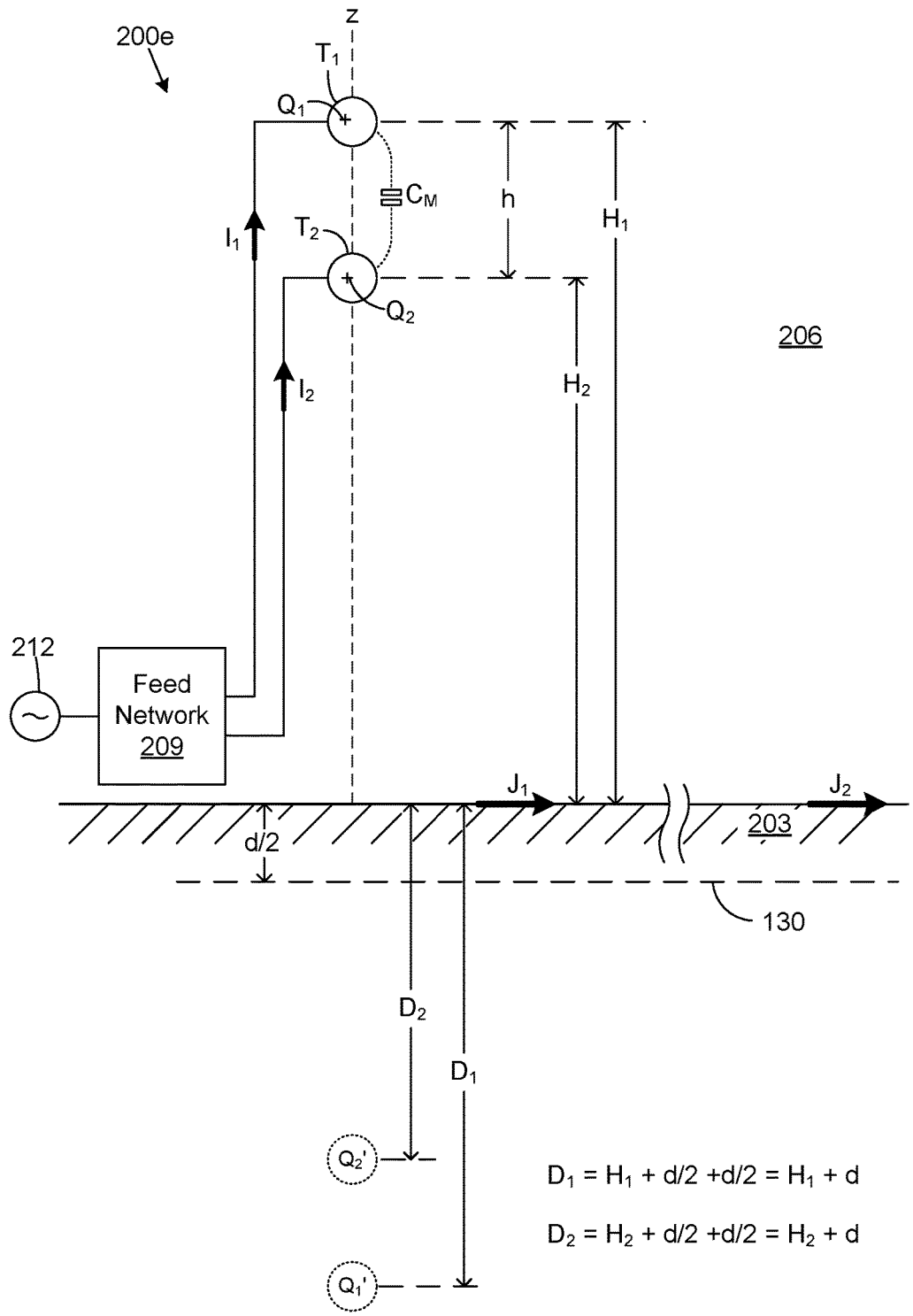
FIG. 16 is a drawing that illustrates an example of a guided surface waveguide probe according to various embodiments of the present disclosure.

With reference then to FIG. 16, shown is an example of a guided surface waveguide probe 200e that includes a charge terminal $T_1$ and a charge terminal $T_2$ that are arranged along a vertical axis z. The guided surface waveguide probe 200e is disposed above a lossy conducting medium 203, which makes up Region 1. In addition, a second medium 206 shares a boundary interface with the lossy conducting medium 203 and makes up Region 2. The charge terminals $T_1$ and $T_2$ are positioned over the lossy conducting medium 203. The charge terminal $T_1$ is positioned at height $H_1$, and the charge terminal $T_2$ is positioned directly below $T_1$ along the vertical axis z at height $H_2$, where $H_2$ is less than $H_1$. The height h of the transmission structure presented by the guided surface waveguide probe 200e is $h=H_1-H_2$. The guided surface waveguide probe 200e includes a feed network 209 that couples an excitation source 212 to the charge terminals $T_1$ and $T_2$.

The charge terminals $T_1$ and/or $T_2$ include a conductive mass that can hold an electrical charge, which may be sized to hold as much charge as practically possible. The charge terminal $T_1$ has a self-capacitance $C_1$, and the charge terminal $T_2$ has a self-capacitance $C_2$, which can be determined using, for example, equation (24). By virtue of the placement of the charge terminal $T_1$ directly above the charge terminal $T_2$, a mutual capacitance $C_M$ is created between the charge terminals $T_1$ and $T_2$. Note that the charge terminals $T_1$ and $T_2$ need not be identical, but each can have a separate size and shape, and can include different conducting materials. Ultimately, the field strength of a guided surface wave launched by a guided surface waveguide probe 200e is directly proportional to the quantity of charge on the terminal $T_1$. The charge $Q_1$ is, in turn, proportional to the self-capacitance $C_1$ associated with the charge terminal $T_1$ since $Q_1=C_1V$, where V is the voltage imposed on the charge terminal $T_1$.

When properly adjusted to operate at a predefined operating frequency, the guided surface waveguide probe 200e generates a guided surface wave along the surface of the lossy conducting medium 203. The excitation source 212 can generate electrical energy at the predefined frequency that is applied to the guided surface waveguide probe 200e to excite the structure. When the electromagnetic fields generated by the guided surface waveguide probe 200e are substantially mode-matched with the lossy conducting medium 203, the electromagnetic fields substantially synthesize a wave front incident at a complex Brewster angle that results in little or no reflection. Thus, the surface waveguide probe 200e does not produce a radiated wave, but launches a guided surface traveling wave along the surface of a lossy conducting medium 203. The energy from the excitation source 212 can be transmitted as Zenneck surface currents to one or more receivers that are located within an effective transmission range of the guided surface waveguide probe 200e.

One can determine asymptotes of the radial Zenneck surface current $J_\rho(\rho)$ on the surface of the lossy conducting medium 203 to be $J_1(\rho)$ close-in and $J_2(\rho)$ far-out, where $$\text{Close-in } (\rho < \lambda/8): J_\rho(\rho) \sim J_1 = \frac{I_1 + I_2}{2\pi\rho} + \frac{E_\rho^{QS}(Q_1) + E_\rho^{QS}(Q_2)}{Z_\rho}, \text{ and} \quad (90)$$

$$\text{Far-out } (\rho \gg \lambda/8): J_\rho(\rho) \sim J_2 = \frac{j\gamma\omega Q_1}{4} \times \sqrt{\frac{2\gamma}{\pi}} \times \frac{e^{-(\alpha+j\beta)\rho}}{\sqrt{\rho}}. \quad (91)$$

where $I_1$ is the conduction current feeding the charge $Q_1$ on the first charge terminal $T_1$, and $I_2$ is the conduction current feeding the charge $Q_2$ on the second charge terminal $T_2$. The charge $Q_1$ on the upper charge terminal $T_1$ is determined by $Q_1=C_1V_1$, where $C_1$ is the isolated capacitance of the charge terminal $T_1$. Note that there is a third component to $J_1$ set forth above given by $(E_\rho^{Q_1})/Z_\rho$, which follows from the Leontovich boundary condition and is the radial current contribution in the lossy conducting medium 203 pumped by the quasi-static field of the elevated oscillating charge on the first charge terminal $Q_1$. The quantity $Z_\rho=j\omega\mu_o/\gamma_e$ is the radial impedance of the lossy conducting medium, where $\gamma_e=(j\omega\mu_1\sigma_1-\omega^2\mu_1\varepsilon_1)^{1/2}$.

The asymptotes representing the radial current close-in and far-out as set forth by equations (90) and (91) are complex quantities. According to various embodiments, a physical surface current $J(\rho)$, is synthesized to match as close as possible the current asymptotes in magnitude and phase. That is to say close-in, $|J(\rho)|$ is to be tangent to $|J_1|$, and far-out $|J(\rho)|$ is to be tangent to $|J_2|$. Also, according to the various embodiments, the phase of $J(\rho)$ should transition from the phase of $J_1$ close-in to the phase of $J_2$ far-out.

In order to match the guided surface wave mode at the site of transmission to launch a guided surface wave, the phase of the surface current $|J_2|$ far-out should differ from the phase of the surface current $|J_1|$ close-in by the propagation phase corresponding to $e^{-j\beta(\rho_2-\rho_1)}$ plus a constant of approximately 45 degrees or 225 degrees. This is because there are two roots for $\sqrt{\gamma}$, one near $\pi/4$ and one near $5\pi/4$. The properly adjusted synthetic radial surface current is $$J_\rho(\rho, \phi, 0) = \frac{I_o \gamma}{4} H_1^{(2)}(-j\gamma\rho). \qquad (92)$$

Note that this is consistent with equation (17). By Maxwell's equations, such a $J(\rho)$ surface current automatically creates fields that conform to $$h_\phi = \frac{-\gamma I_o}{4} e^{-u_2 z} H_1^{(2)}(-j\gamma\rho), \qquad (93)$$

$$E_\rho = \frac{-\gamma I_o}{4} \left(\frac{u_2}{j\omega\varepsilon_o}\right) e^{-u_2 z} H_1^{(2)}(-j\gamma\rho), \text{ and} \qquad (94)$$

$$E_z = \frac{-\gamma I_o}{4} \left(\frac{-\gamma}{\omega\varepsilon_o}\right) e^{-u_2 z} H_0^{(2)}(-j\gamma\rho). \qquad (95)$$

Thus, the difference in phase between the surface current $|J_2|$ far-out and the surface current $|J_1|$ close-in for the guided surface wave mode that is to be matched is due to the characteristics of the Hankel functions in equations (93)-(95), which are consistent with equations (1)-(3). It is of significance to recognize that the fields expressed by equations (1)-(6) and (17) and equations (92)-(95) have the nature of a transmission line mode bound to a lossy interface, not radiation fields that are associated with ground-wave propagation.

In order to obtain the appropriate voltage magnitudes and phases for a given design of a guided surface waveguide probe 200e at a given location, an iterative approach may be used. Specifically, analysis may be performed of a given excitation and configuration of a guided surface waveguide probe 200e taking into account the feed currents to the terminals $T_1$ and $T_2$, the charges on the charge terminals $T_1$ and $T_2$, and their images in the lossy conducting medium 203 in order to determine the radial surface current density generated. This process may be performed iteratively until an optimal configuration and excitation for a given guided surface waveguide probe 200e is determined based on desired parameters. To aid in determining whether a given guided surface waveguide probe 200e is operating at an optimal level, a guided field strength curve 103 (FIG. 1) may be generated using equations (1)-(12) based on values for the conductivity of Region 1 ($\sigma_1$) and the permittivity of Region 1 ($\varepsilon_1$) at the location of the guided surface waveguide probe 200e. Such a guided field strength curve 103 can provide a benchmark for operation such that measured field strengths can be compared with the magnitudes indicated by the guided field strength curve 103 to determine if optimal transmission has been achieved.

In order to arrive at an optimized condition, various parameters associated with the guided surface waveguide probe 200e may be adjusted. One parameter that may be varied to adjust the guided surface waveguide probe 200e is the height of one or both of the charge terminals $T_1$ and/or $T_2$ relative to the surface of the lossy conducting medium 203. In addition, the distance or spacing between the charge terminals $T_1$ and $T_2$ may also be adjusted. In doing so, one may minimize or otherwise alter the mutual capacitance $C_M$ or any bound capacitances between the charge terminals $T_1$ and $T_2$ and the lossy conducting medium 203 as can be appreciated. The size of the respective charge terminals $T_1$ and/or $T_2$ can also be adjusted. By changing the size of the charge terminals $T_1$ and/or $T_2$, one will alter the respective self-capacitances $C_1$ and/or $C_2$, and the mutual capacitance $C_M$ as can be appreciated.

Still further, another parameter that can be adjusted is the feed network 209 associated with the guided surface waveguide probe 200e. This may be accomplished by adjusting the size of the inductive and/or capacitive reactances that make up the feed network 209. For example, where such inductive reactances comprise coils, the number of turns on such coils may be adjusted. Ultimately, the adjustments to the feed network 209 can be made to alter the electrical length of the feed network 209, thereby affecting the voltage magnitudes and phases on the charge terminals $T_1$ and $T_2$.

Note that the iterations of transmission performed by making the various adjustments may be implemented by using computer models or by adjusting physical structures as can be appreciated. By making the above adjustments, one can create corresponding "close-in" surface current $J_1$ and "far-out" surface current $J_2$ that approximate the same currents $J(\rho)$ of the guided surface wave mode specified in Equations (90) and (91) set forth above. In doing so, the resulting electromagnetic fields would be substantially or approximately mode-matched to a guided surface wave mode on the surface of the lossy conducting medium 203.

While not shown in the example of FIG. 16, operation of the guided surface waveguide probe 200e may be controlled to adjust for variations in operational conditions associated with the guided surface waveguide probe 200. For example, a probe control system 230 shown in FIG. 12 can be used to control the feed network 209 and/or positioning and/or size of the charge terminals $T_1$ and/or $T_2$ to control the operation of the guided surface waveguide probe 200e. Operational conditions can include, but are not limited to, variations in the characteristics of the lossy conducting medium 203 (e.g., conductivity $\sigma$ and relative permittivity $\varepsilon_r$), variations in field strength and/or variations in loading of the guided surface waveguide probe 200e.

Figure 17:
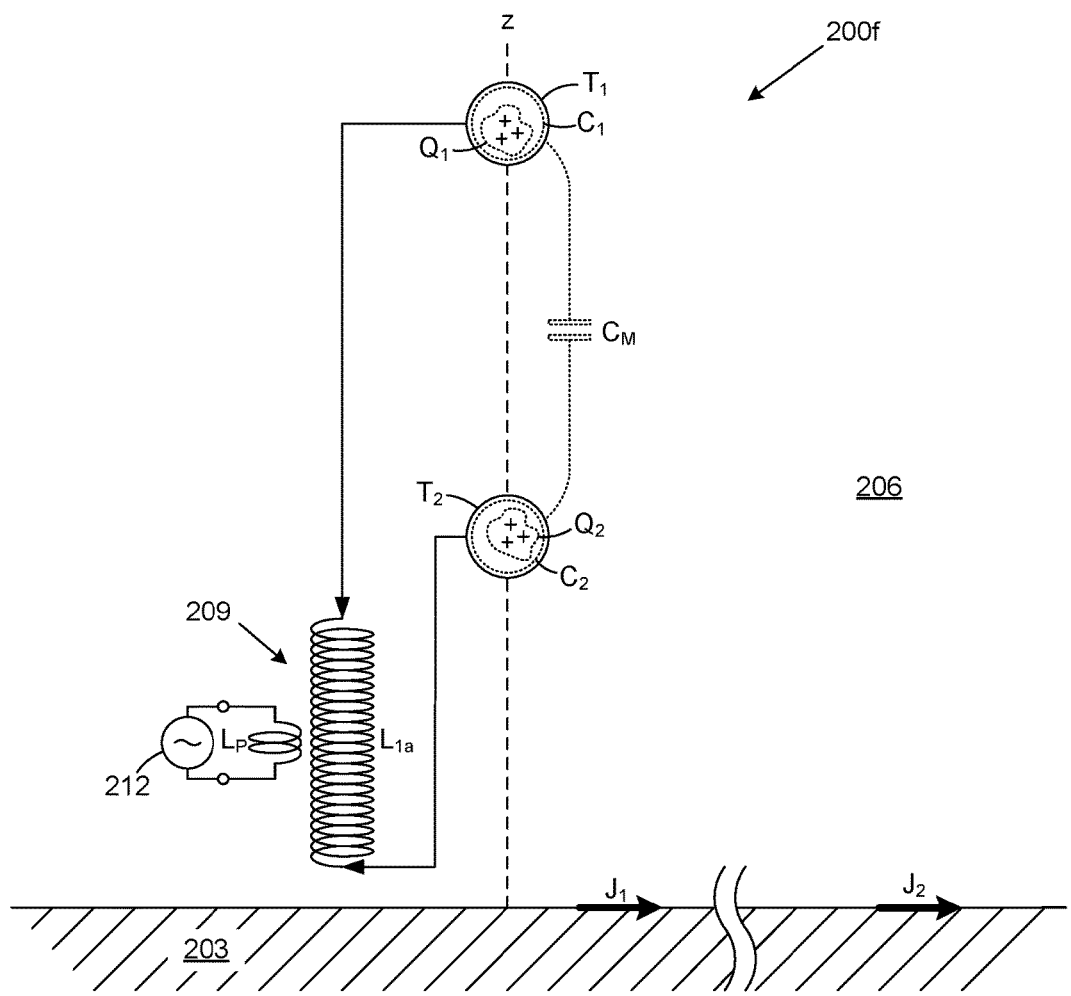
FIG. 17 is a graphical representation of an example of a guided surface waveguide probe of FIG. 16 according to various embodiments of the present disclosure.

Referring now to FIG. 17, shown is an example of the guided surface waveguide probe 200e of FIG. 16, denoted herein as guided surface waveguide probe 200f. The guided surface waveguide probe 200f includes the charge terminals $T_1$ and $T_2$ that are positioned along a vertical axis z that is substantially normal to the plane presented by the lossy conducting medium 203 (e.g., the Earth). The second medium 206 is above the lossy conducting medium 203. The charge terminal $T_1$ has a self-capacitance $C_1$, and the charge terminal $T_2$ has a self-capacitance $C_2$. During operation, charges $Q_1$ and $Q_2$ are imposed on the charge terminals $T_1$ and $T_2$, respectively, depending on the voltages applied to the charge terminals $T_1$ and $T_2$ at any given instant. A mutual capacitance $C_M$ may exist between the charge terminals $T_1$ and $T_2$ depending on the distance there between. In addition, bound capacitances may exist between the respective charge terminals $T_1$ and $T_2$ and the lossy conducting medium 203 depending on the heights of the respective charge terminals $T_1$ and $T_2$ with respect to the lossy conducting medium 203.

The guided surface waveguide probe 200f includes a feed network 209 that comprises an inductive impedance comprising a coil $L_{1a}$ having a pair of leads that are coupled to respective ones of the charge terminals $T_1$ and $T_2$. In one embodiment, the coil $L_{1a}$ is specified to have an electrical length that is one-half (½) of the wavelength at the operating frequency of the guided surface waveguide probe 200f.

While the electrical length of the coil $L_{1a}$ is specified as approximately one-half (½) the wavelength at the operating frequency, it is understood that the coil $L_{1a}$ may be specified with an electrical length at other values. According to one embodiment, the fact that the coil $L_{1a}$ has an electrical length of approximately one-half the wavelength at the operating frequency provides for an advantage in that a maximum voltage differential is created on the charge terminals $T_1$ and $T_2$. Nonetheless, the length or diameter of the coil $L_{1a}$ may be increased or decreased when adjusting the guided surface waveguide probe 200f to obtain optimal excitation of a guided surface wave mode. Adjustment of the coil length may be provided by taps located at one or both ends of the coil. In other embodiments, it may be the case that the inductive impedance is specified to have an electrical length that is significantly less than or greater than ½ the wavelength at the operating frequency of the guided surface waveguide probe 200f.

The excitation source 212 can be coupled to the feed network 209 by way of magnetic coupling. Specifically, the excitation source 212 is coupled to a coil $L_P$ that is inductively coupled to the coil $L_{1a}$. This may be done by link coupling, a tapped coil, a variable reactance, or other coupling approach as can be appreciated. To this end, the coil $L_P$ acts as a primary, and the coil $L_{1a}$ acts as a secondary as can be appreciated.

In order to adjust the guided surface waveguide probe 200f for the transmission of a desired guided surface wave, the heights of the respective charge terminals $T_1$ and $T_2$ may be altered with respect to the lossy conducting medium 203 and with respect to each other. Also, the sizes of the charge terminals $T_1$ and $T_2$ may be altered. In addition, the size of the coil $L_{1a}$ may be altered by adding or eliminating turns or by changing some other dimension of the coil $L_{1a}$. The coil $L_{1a}$ can also include one or more taps for adjusting the electrical length as shown in FIG. 17. The position of a tap connected to either charge terminal $T_1$ or $T_2$ can also be adjusted.

Figure 18A:
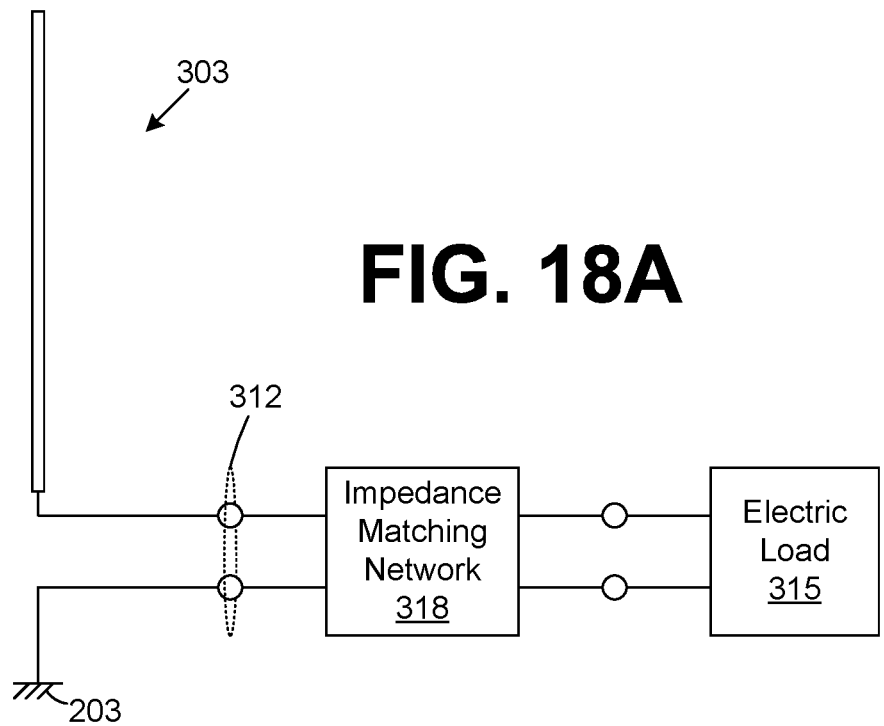
FIGS. 18A through 18C depict examples of receiving structures that can be employed to receive energy transmitted in the form of a guided surface wave launched by a guided surface waveguide probe according to the various embodiments of the present disclosure.
Figure 18B:
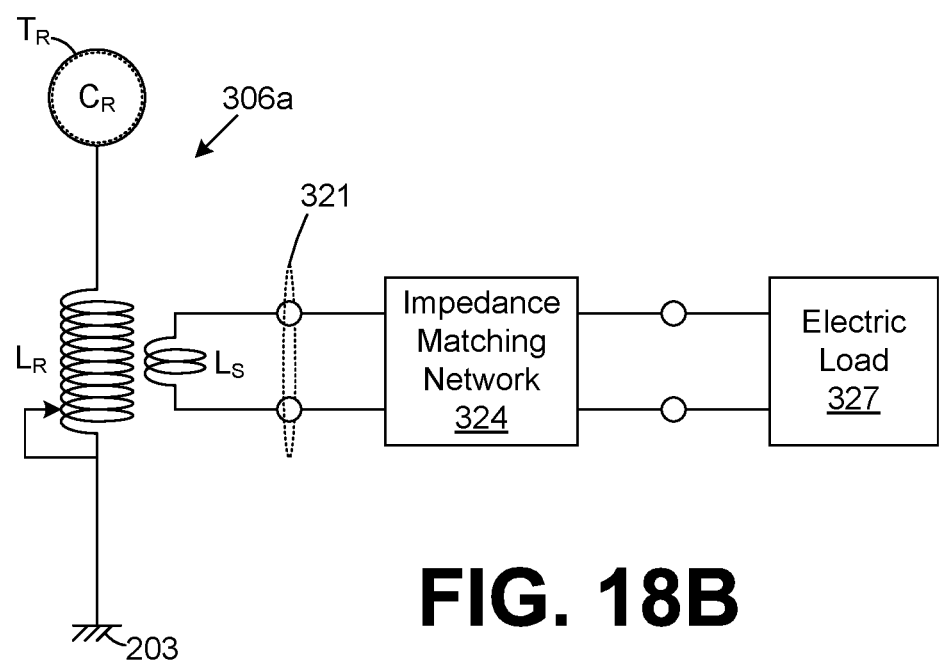
Figure 18C:
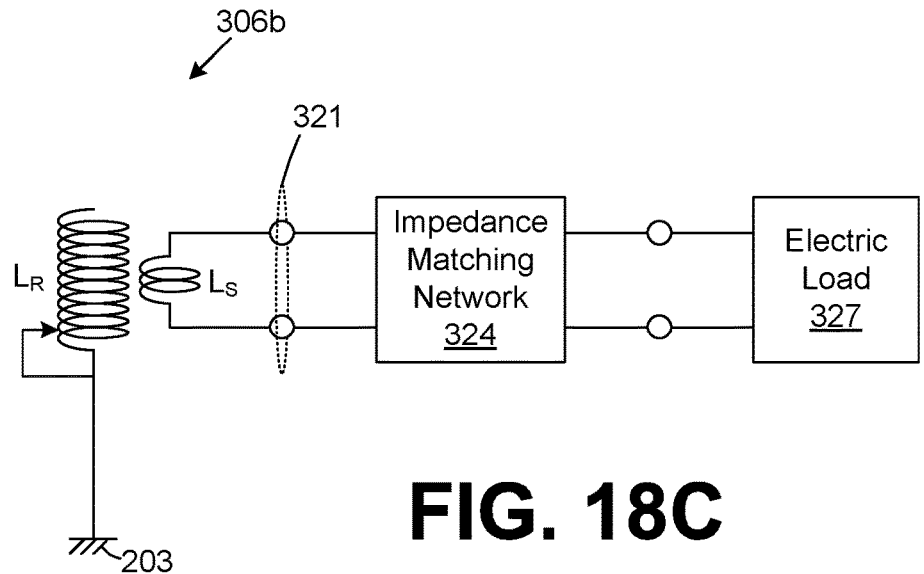
Figure 19:
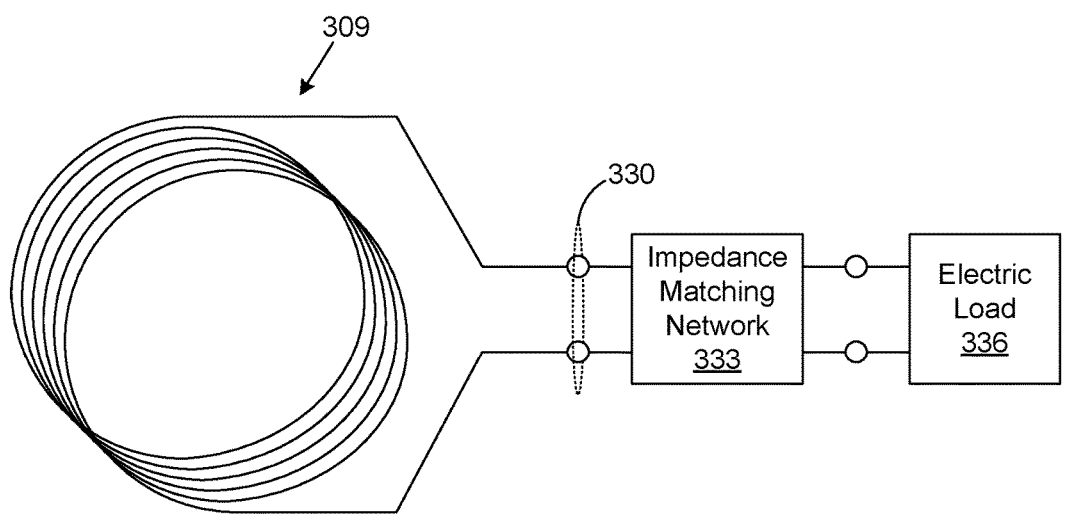
FIG. 19 depicts an example of an additional receiving structure that can be employed to receive energy transmitted in the form of a guided surface wave launched by a guided surface waveguide probe according to the various embodiments of the present disclosure.

Referring next to FIGS. 18A, 18B, 18C and 19, shown are examples of generalized receive circuits for using the surface-guided waves in wireless power delivery systems. FIGS. 18A and 18B-18C include a linear probe 303 and a tuned resonator 306, respectively. FIG. 19 is a magnetic coil 309 according to various embodiments of the present disclosure. According to various embodiments, each one of the linear probe 303, the tuned resonator 306, and the magnetic coil 309 may be employed to receive power transmitted in the form of a guided surface wave on the surface of a lossy conducting medium 203 according to various embodiments. As mentioned above, in one embodiment the lossy conducting medium 203 comprises a terrestrial medium (or Earth).

With specific reference to FIG. 18A, the open-circuit terminal voltage at the output terminals 312 of the linear probe 303 depends upon the effective height of the linear probe 303. To this end, the terminal point voltage may be calculated as $$V_T = \int_0^{h_e} E_{inc} \cdot dl, \quad (96)$$

where $E_{inc}$ is the strength of the incident electric field induced on the linear probe 303 in Volts per meter, dl is an element of integration along the direction of the linear probe 303, and $h_e$ is the effective height of the linear probe 303. An electrical load 315 is coupled to the output terminals 312 through an impedance matching network 318.

When the linear probe 303 is subjected to a guided surface wave as described above, a voltage is developed across the output terminals 312 that may be applied to the electrical load 315 through a conjugate impedance matching network 318 as the case may be. In order to facilitate the flow of power to the electrical load 315, the electrical load 315 should be substantially impedance matched to the linear probe 303 as will be described below.

Referring to FIG. 18B, a ground current excited coil 306a possessing a phase shift equal to the wave tilt of the guided surface wave includes a charge terminal $T_R$ that is elevated (or suspended) above the lossy conducting medium 203. The charge terminal $T_R$ has a self-capacitance $C_R$. In addition, there may also be a bound capacitance (not shown) between the charge terminal $T_R$ and the lossy conducting medium 203 depending on the height of the charge terminal $T_R$ above the lossy conducting medium 203. The bound capacitance should preferably be minimized as much as is practicable, although this may not be entirely necessary in every instance.

The tuned resonator 306a also includes a receiver network comprising a coil $L_R$ having a phase shift Φ. One end of the coil $L_R$ is coupled to the charge terminal $T_R$, and the other end of the coil $L_R$ is coupled to the lossy conducting medium 203. The receiver network can include a vertical supply line conductor that couples the coil $L_R$ to the charge terminal $T_R$. To this end, the coil $L_R$ (which may also be referred to as tuned resonator $L_R$–$C_R$) comprises a series-adjusted resonator as the charge terminal $C_R$ and the coil $L_R$ are situated in series. The phase delay of the coil $L_R$ can be adjusted by changing the size and/or height of the charge terminal $T_R$, and/or adjusting the size of the coil $L_R$ so that the phase Φ of the structure is made substantially equal to the angle of the wave tilt Ψ. The phase delay of the vertical supply line can also be adjusted by, e.g., changing length of the conductor.

For example, the reactance presented by the self-capacitance $C_R$ is calculated as $1/j\omega C_R$. Note that the total capacitance of the structure 306a may also include capacitance between the charge terminal $T_R$ and the lossy conducting medium 203, where the total capacitance of the structure 306a may be calculated from both the self-capacitance $C_R$ and any bound capacitance as can be appreciated. According to one embodiment, the charge terminal $T_R$ may be raised to a height so as to substantially reduce or eliminate any bound capacitance. The existence of a bound capacitance may be determined from capacitance measurements between the charge terminal $T_R$ and the lossy conducting medium 203 as previously discussed.

The inductive reactance presented by a discrete-element coil $L_R$ may be calculated as $j\omega L$, where L is the lumped-element inductance of the coil $L_R$. If the coil $L_R$ is a distributed element, its equivalent terminal-point inductive reactance may be determined by conventional approaches. To tune the structure 306a, one would make adjustments so that the phase delay is equal to the wave tilt for the purpose of mode-matching to the surface waveguide at the frequency of operation. Under this condition, the receiving structure may be considered to be "mode-matched" with the surface waveguide. A transformer link around the structure and/or an impedance matching network 324 may be inserted between the probe and the electrical load 327 in order to couple power to the load. Inserting the impedance matching network 324 between the probe terminals 321 and the electrical load 327 can effect a conjugate-match condition for maximum power transfer to the electrical load 327.

When placed in the presence of surface currents at the operating frequencies power will be delivered from the surface guided wave to the electrical load 327. To this end, an electrical load 327 may be coupled to the structure 306a by way of magnetic coupling, capacitive coupling, or conductive (direct tap) coupling. The elements of the coupling network may be lumped components or distributed elements as can be appreciated.

In the embodiment shown in FIG. 18B, magnetic coupling is employed where a coil $L_S$ is positioned as a secondary relative to the coil $L_R$ that acts as a transformer primary. The coil $L_S$ may be link-coupled to the coil $L_R$ by geometrically winding it around the same core structure and adjusting the coupled magnetic flux as can be appreciated. In addition, while the receiving structure 306a comprises a series-tuned resonator, a parallel-tuned resonator or even a distributed-element resonator of the appropriate phase delay may also be used.

While a receiving structure immersed in an electromagnetic field may couple energy from the field, it can be appreciated that polarization-matched structures work best by maximizing the coupling, and conventional rules for probe-coupling to waveguide modes should be observed. For example, a $TE_{20}$ (transverse electric mode) waveguide probe may be optimal for extracting energy from a conventional waveguide excited in the $TE_{20}$ mode. Similarly, in these cases, a mode-matched and phase-matched receiving structure can be optimized for coupling power from a surface-guided wave. The guided surface wave excited by a guided surface waveguide probe 200 on the surface of the lossy conducting medium 203 can be considered a waveguide mode of an open waveguide. Excluding waveguide losses, the source energy can be completely recovered. Useful receiving structures may be E-field coupled, H-field coupled, or surface-current excited.

The receiving structure can be adjusted to increase or maximize coupling with the guided surface wave based upon the local characteristics of the lossy conducting medium 203 in the vicinity of the receiving structure. To accomplish this, the phase delay ($\Phi$) of the receiving structure can be adjusted to match the angle ($\Psi$) of the wave tilt of the surface traveling wave at the receiving structure. If configured appropriately, the receiving structure may then be tuned for resonance with respect to the perfectly conducting image ground plane at complex depth $z=-d/2$.

For example, consider a receiving structure comprising the tuned resonator 306a of FIG. 18B, including a coil $L_R$ and a vertical supply line connected between the coil $L_R$ and a charge terminal $T_R$. With the charge terminal $T_R$ positioned at a defined height above the lossy conducting medium 203, the total phase shift $\Phi$ of the coil $L_R$ and vertical supply line can be matched with the angle ($\Psi$) of the wave tilt at the location of the tuned resonator 306a. From Equation (22), it can be seen that the wave tilt asymptotically passes to $$W = |W|e^{j\Psi} = \frac{E_\rho}{E_z} \xrightarrow{\rho \to \infty} \frac{1}{\sqrt{\varepsilon_r - j\frac{\sigma_1}{\omega \varepsilon_o}}}, \tag{97}$$

where $\varepsilon_r$ comprises the relative permittivity and $\sigma_1$ is the conductivity of the lossy conducting medium 203 at the location of the receiving structure, $\varepsilon_o$ is the permittivity of free space, and $\omega=2\pi f$, where f is the frequency of excitation. Thus, the wave tilt angle ($\Psi$) can be determined from Equation (97).

The total phase shift ($\Phi=\theta_c+\theta_y$) of the tuned resonator 306a includes both the phase delay ($\theta_c$) through the coil $L_R$ and the phase delay of the vertical supply line ($\theta_y$). The spatial phase delay along the conductor length $l_w$ of the vertical supply line can be given by $\theta_y=\beta_w l_w$, where $\beta_w$ is the propagation phase constant for the vertical supply line conductor. The phase delay due to the coil (or helical delay line) is $\theta_c=\beta_p l_C$, with a physical length of $l_C$ and a propagation factor of $$\beta_p = \frac{2\pi}{\lambda_p} = \frac{2\pi}{V_f \lambda_0}, \tag{98}$$

where $V_f$ is the velocity factor on the structure, $\lambda_0$ is the wavelength at the supplied frequency, and $\lambda_p$ is the propagation wavelength resulting from the velocity factor $V_f$. One or both of the phase delays ($\theta_c+\theta_y$) can be adjusted to match the phase shift $\Phi$ to the angle ($\Psi$) of the wave tilt. For example, a tap position may be adjusted on the coil $L_R$ of FIG. 18B to adjust the coil phase delay ($\theta_c$) to match the total phase shift to the wave tilt angle ($\Phi=\Psi$). For example, a portion of the coil can be bypassed by the tap connection as illustrated in FIG. 18B. The vertical supply line conductor can also be connected to the coil $L_R$ via a tap, whose position on the coil may be adjusted to match the total phase shift to the angle of the wave tilt.

Once the phase delay ($\Phi$) of the tuned resonator 306a has been adjusted, the impedance of the charge terminal $T_R$ can then be adjusted to tune to resonance with respect to the perfectly conducting image ground plane at complex depth $z=-d/2$. This can be accomplished by adjusting the capacitance of the charge terminal $T_1$ without changing the traveling wave phase delays of the coil $L_R$ and vertical supply line. The adjustments are similar to those described with respect to FIGS. 9A and 9B.

The impedance seen "looking down" into the lossy conducting medium 203 to the complex image plane is given by:

$$Z_{in} = R_{in} + jX_{in} = Z_o \tan h(j\beta_o(d/2)), \tag{99}$$

where $\beta_o = \omega\sqrt{\mu_o \varepsilon_o}$. For vertically polarized sources over the Earth, the depth of the complex image plane can be given by:

$$d/2 \approx 1/\sqrt{j\omega\mu_1\sigma_1 - \omega^2\mu_1\varepsilon_1}, \tag{100}$$

where $\mu_1$ is the permeability of the lossy conducting medium 203 and $\varepsilon_1 = \varepsilon_r \varepsilon_o$.

At the base of the tuned resonator 306a, the impedance seen "looking up" into the receiving structure is $Z_\uparrow = Z_{base}$ as illustrated in FIG. 9A. With a terminal impedance of:

$$Z_R = \frac{1}{j\omega C_R}, \tag{101}$$

where $C_R$ is the self-capacitance of the charge terminal $T_R$, the impedance seen "looking up" into the vertical supply line conductor of the tuned resonator 306a is given by:

$$Z_2 = Z_W \frac{Z_R + Z_w \tanh(j\beta_w h_w)}{Z_w + Z_R \tanh(j\beta_w h_w)} = Z_W \frac{Z_R + Z_w \tanh(j\theta_y)}{Z_w + Z_R \tanh(j\theta_y)}, \tag{102}$$

and the impedance seen "looking up" into the coil $L_R$ of the tuned resonator 306a is given by:

$$Z_{base} = \tag{103}$$
$$R_{base} + jX_{base} = Z_R \frac{Z_2 + Z_R \tanh(j\beta_p H)}{Z_R + Z_2 \tanh(j\beta_p H)} = Z_c \frac{Z_2 + Z_R \tanh(j\theta_c)}{Z_R + Z_2 \tanh(j\theta_c)}.$$

By matching the reactive component ($X_{in}$) seen "looking down" into the lossy conducting medium 203 with the reactive component ($X_{base}$) seen "looking up" into the tuned resonator 306a, the coupling into the guided surface waveguide mode may be maximized.

Referring next to FIG. 18C, shown is an example of a tuned resonator 306b that does not include a charge terminal $T_R$ at the top of the receiving structure. In this embodiment, the tuned resonator 306b does not include a vertical supply line coupled between the coil $L_R$ and the charge terminal $T_R$. Thus, the total phase shift ($\Phi$) of the tuned resonator 306b includes only the phase delay ($\theta_c$) through the coil $L_R$. As with the tuned resonator 306a of FIG. 18B, the coil phase delay $\theta_c$ can be adjusted to match the angle ($\Psi$) of the wave tilt determined from Equation (97), which results in $\Phi=\Psi$. While power extraction is possible with the receiving structure coupled into the surface waveguide mode, it is difficult to adjust the receiving structure to maximize coupling with the guided surface wave without the variable reactive load provided by the charge terminal $T_R$.

Figure 18D:
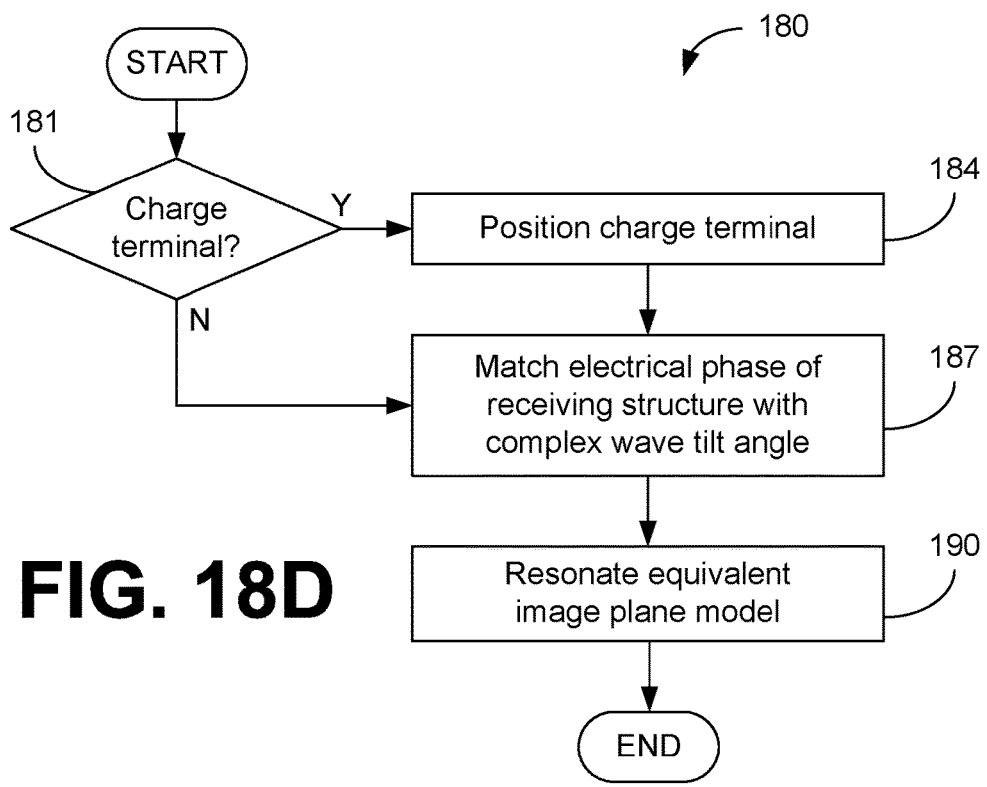
FIG. 18D is a flow chart illustrating an example of adjusting a receiving structure according to various embodiments of the present disclosure.

Referring to FIG. 18D, shown is a flow chart 180 illustrating an example of adjusting a receiving structure to substantially mode-match to a guided surface waveguide mode on the surface of the lossy conducting medium 203. Beginning with 181, if the receiving structure includes a charge terminal $T_R$ (e.g., of the tuned resonator 306a of FIG. 18B), then the charge terminal $T_R$ is positioned at a defined height above a lossy conducting medium 203 at 184. As the surface guided wave has been established by a guided surface waveguide probe 200, the physical height ($h_p$) of the charge terminal $T_R$ may be below that of the effective height. The physical height may be selected to reduce or minimize the bound charge on the charge terminal $T_R$ (e.g., four times the spherical diameter of the charge terminal). If the receiving structure does not include a charge terminal $T_R$ (e.g., of the tuned resonator 306b of FIG. 18C), then the flow proceeds to 187.

At 187, the electrical phase delay $\Phi$ of the receiving structure is matched to the complex wave tilt angle $\Psi$ defined by the local characteristics of the lossy conducting medium 203. The phase delay ($\theta_c$) of the helical coil and/or the phase delay ($\theta_y$) of the vertical supply line can be adjusted to make $\Phi$ equal to the angle ($\Psi$) of the wave tilt (W). The angle ($\Psi$) of the wave tilt can be determined from Equation (86). The electrical phase $\Phi$ can then be matched to the angle of the wave tilt. For example, the electrical phase delay $\Phi=\theta_c+\theta_y$ can be adjusted by varying the geometrical parameters of the coil $L_R$ and/or the length (or height) of the vertical supply line conductor.

Next at 190, the load impedance of the charge terminal $T_R$ can be tuned to resonate the equivalent image plane model of the tuned resonator 306a. The depth (d/2) of the conducting image ground plane 139 (FIG. 9A) below the receiving structure can be determined using Equation (100) and the values of the lossy conducting medium 203 (e.g., the Earth) at the receiving structure, which can be locally measured. Using that complex depth, the phase shift ($\theta_d$) between the image ground plane 139 and the physical boundary 136 (FIG. 9A) of the lossy conducting medium 203 can be determined using $\theta_d=\beta_o\, d/2$. The impedance ($Z_{in}$) as seen "looking down" into the lossy conducting medium 203 can then be determined using Equation (99). This resonance relationship can be considered to maximize coupling with the guided surface waves.

Based upon the adjusted parameters of the coil $L_R$ and the length of the vertical supply line conductor, the velocity factor, phase delay, and impedance of the coil $L_R$ and vertical supply line can be determined. In addition, the self-capacitance ($C_R$) of the charge terminal $T_R$ can be determined using, e.g., Equation (24). The propagation factor ($\beta_p$) of the coil $L_R$ can be determined using Equation (98), and the propagation phase constant ($\beta_w$) for the vertical supply line can be determined using Equation (49). Using the self-capacitance and the determined values of the coil $L_R$ and vertical supply line, the impedance ($Z_{base}$) of the tuned resonator 306a as seen "looking up" into the coil $L_R$ can be determined using Equations (101), (102), and (103).

The equivalent image plane model of FIG. 9A also applies to the tuned resonator 306a of FIG. 18B. The tuned resonator 306a can be tuned to resonance with respect to the complex image plane by adjusting the load impedance $Z_R$ of the charge terminal $T_R$ such that the reactance component $X_{base}$ of $Z_{base}$ cancels out the reactance component of $X_{in}$ of $Z_{in}$, or $X_{base}+X_{in}=0$. Thus, the impedance at the physical boundary 136 (FIG. 9A) "looking up" into the coil of the tuned resonator 306a is the conjugate of the impedance at the physical boundary 136 "looking down" into the lossy conducting medium 203. The load impedance $Z_R$ can be adjusted by varying the capacitance ($C_R$) of the charge terminal $T_R$ without changing the electrical phase delay $\Phi=\theta_c+\theta_y$ seen by the charge terminal $T_R$. An iterative approach may be taken to tune the load impedance $Z_R$ for resonance of the equivalent image plane model with respect to the conducting image ground plane 139. In this way, the coupling of the electric field to a guided surface waveguide mode along the surface of the lossy conducting medium 203 (e.g., Earth) can be improved and/or maximized.

Referring to FIG. 19, the magnetic coil 309 comprises a receive circuit that is coupled through an impedance matching network 333 to an electrical load 336. In order to facilitate reception and/or extraction of electrical power from a guided surface wave, the magnetic coil 309 may be positioned so that the magnetic flux of the guided surface wave, $H_\varphi$, passes through the magnetic coil 309, thereby inducing a current in the magnetic coil 309 and producing a terminal point voltage at its output terminals 330. The magnetic flux of the guided surface wave coupled to a single turn coil is expressed by $$\mathcal{F} = \iint_{A_{CS}} \mu_r \mu_o \vec{H} \cdot \hat{n}\, dA \tag{104}$$

where $\mathcal{F}$ is the coupled magnetic flux, $\mu_r$ is the effective relative permeability of the core of the magnetic coil 309, $\mu_o$ is the permeability of free space, $\vec{H}$ is the incident magnetic field strength vector, $\hat{n}$ is a unit vector normal to the cross-sectional area of the turns, and $A_{CS}$ is the area enclosed by each loop. For an N-turn magnetic coil 309 oriented for maximum coupling to an incident magnetic field that is uniform over the cross-sectional area of the magnetic coil 309, the open-circuit induced voltage appearing at the output terminals 330 of the magnetic coil 309 is $$V = -N\frac{d\mathcal{F}}{dt} \approx -j\omega\mu_r\mu_0 N H A_{CS}, \tag{105}$$

where the variables are defined above. The magnetic coil 309 may be tuned to the guided surface wave frequency either as a distributed resonator or with an external capacitor across its output terminals 330, as the case may be, and then impedance-matched to an external electrical load 336 through a conjugate impedance matching network 333.

Assuming that the resulting circuit presented by the magnetic coil 309 and the electrical load 336 are properly adjusted and conjugate impedance matched, via impedance matching network 333, then the current induced in the magnetic coil 309 may be employed to optimally power the electrical load 336. The receive circuit presented by the magnetic coil 309 provides an advantage in that it does not have to be physically connected to the ground.

With reference to FIGS. 18A, 18B, 18C and 19, the receive circuits presented by the linear probe 303, the mode-matched structure 306, and the magnetic coil 309 each facilitate receiving electrical power transmitted from any one of the embodiments of guided surface waveguide probes 200 described above. To this end, the energy received may be used to supply power to an electrical load 315/327/336 via a conjugate matching network as can be appreciated. This contrasts with the signals that may be received in a receiver that were transmitted in the form of a radiated electromagnetic field. Such signals have very low available power, and receivers of such signals do not load the transmitters.

It is also characteristic of the present guided surface waves generated using the guided surface waveguide probes 200 described above that the receive circuits presented by the linear probe 303, the mode-matched structure 306, and the magnetic coil 309 will load the excitation source 212 (e.g., FIGS. 3, 12 and 16) that is applied to the guided surface waveguide probe 200, thereby generating the guided surface wave to which such receive circuits are subjected. This reflects the fact that the guided surface wave generated by a given guided surface waveguide probe 200 described above comprises a transmission line mode. By way of contrast, a power source that drives a radiating antenna that generates a radiated electromagnetic wave is not loaded by the receivers, regardless of the number of receivers employed.

Thus, together one or more guided surface waveguide probes 200 and one or more receive circuits in the form of the linear probe 303, the tuned mode-matched structure 306, and/or the magnetic coil 309 can make up a wireless distribution system. Given that the distance of transmission of a guided surface wave using a guided surface waveguide probe 200 as set forth above depends upon the frequency, it is possible that wireless power distribution can be achieved across wide areas and even globally.

The conventional wireless-power transmission/distribution systems extensively investigated today include "energy harvesting" from radiation fields and also sensor coupling to inductive or reactive near-fields. In contrast, the present wireless-power system does not waste power in the form of radiation which, if not intercepted, is lost forever. Nor is the presently disclosed wireless-power system limited to extremely short ranges as with conventional mutual-reactance coupled near-field systems. The wireless-power system disclosed herein probe-couples to the novel surface-guided transmission line mode, which is equivalent to delivering power to a load by a waveguide or a load directly wired to the distant power generator. Not counting the power required to maintain transmission field strength plus that dissipated in the surface waveguide, which at extremely low frequencies is insignificant relative to the transmission losses in conventional high-tension power lines at 60 Hz, all of the generator power goes only to the desired electrical load. When the electrical load demand is terminated, the source power generation is relatively idle.

Figure 20A:
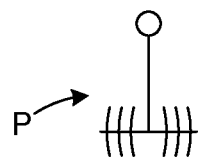
FIGS. 20A through 20E depict examples of various schematic symbols according to various embodiments of the present disclosure.

Referring next to FIGS. 20A-E, shown are examples of various schematic symbols that are used with reference to the discussion that follows. With specific reference to FIG. 20A, shown is a symbol that represents any one of the guided surface waveguide probes 200a, 200b, 200c, 200e, 200d, or 200f; or any variations thereof. In the following drawings and discussion, a depiction of this symbol will be referred to as a guided surface waveguide probe P. For the sake of simplicity in the following discussion, any reference to the guided surface waveguide probe P is a reference to any one of the guided surface waveguide probes 200a, 200b, 200c, 200e, 200d, or 200f; or variations thereof.

Figure 20B:
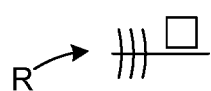

Similarly, with reference to FIG. 20B, shown is a symbol that represents a guided surface wave receive structure that may comprise any one of the linear probe 303 (FIG. 18A), the tuned resonator 306 (FIGS. 18B-18C), or the magnetic coil 309 (FIG. 19). In the following drawings and discussion, a depiction of this symbol will be referred to as a guided surface wave receive structure R. For the sake of simplicity in the following discussion, any reference to the guided surface wave receive structure R is a reference to any one of the linear probe 303, the tuned resonator 306, the magnetic coil 309, or variations thereof.

Figure 20C:
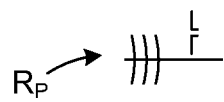

Further, with reference to FIG. 20C, shown is a symbol that specifically represents the linear probe 303 (FIG. 18A). In the following drawings and discussion, a depiction of this symbol will be referred to as a guided surface wave receive structure $R_P$. For the sake of simplicity in the following discussion, any reference to the guided surface wave receive structure $R_P$ is a reference to the linear probe 303 or variations thereof.

Figure 20D:
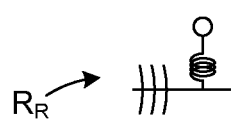

Further, with reference to FIG. 20D, shown is a symbol that specifically represents the tuned resonator 306 (FIGS. 18B-18C). In the following drawings and discussion, a depiction of this symbol will be referred to as a guided surface wave receive structure $R_R$. For the sake of simplicity in the following discussion, any reference to the guided surface wave receive structure $R_R$ is a reference to the tuned resonator 306 or variations thereof.

Figure 20E:
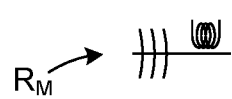

Further, with reference to FIG. 20E, shown is a symbol that specifically represents the magnetic coil 309 (FIG. 19). In the following drawings and discussion, a depiction of this symbol will be referred to as a guided surface wave receive structure $R_M$. For the sake of simplicity in the following discussion, any reference to the guided surface wave receive structure $R_M$ is a reference to the magnetic coil 309 or variations thereof.

Figure 21:
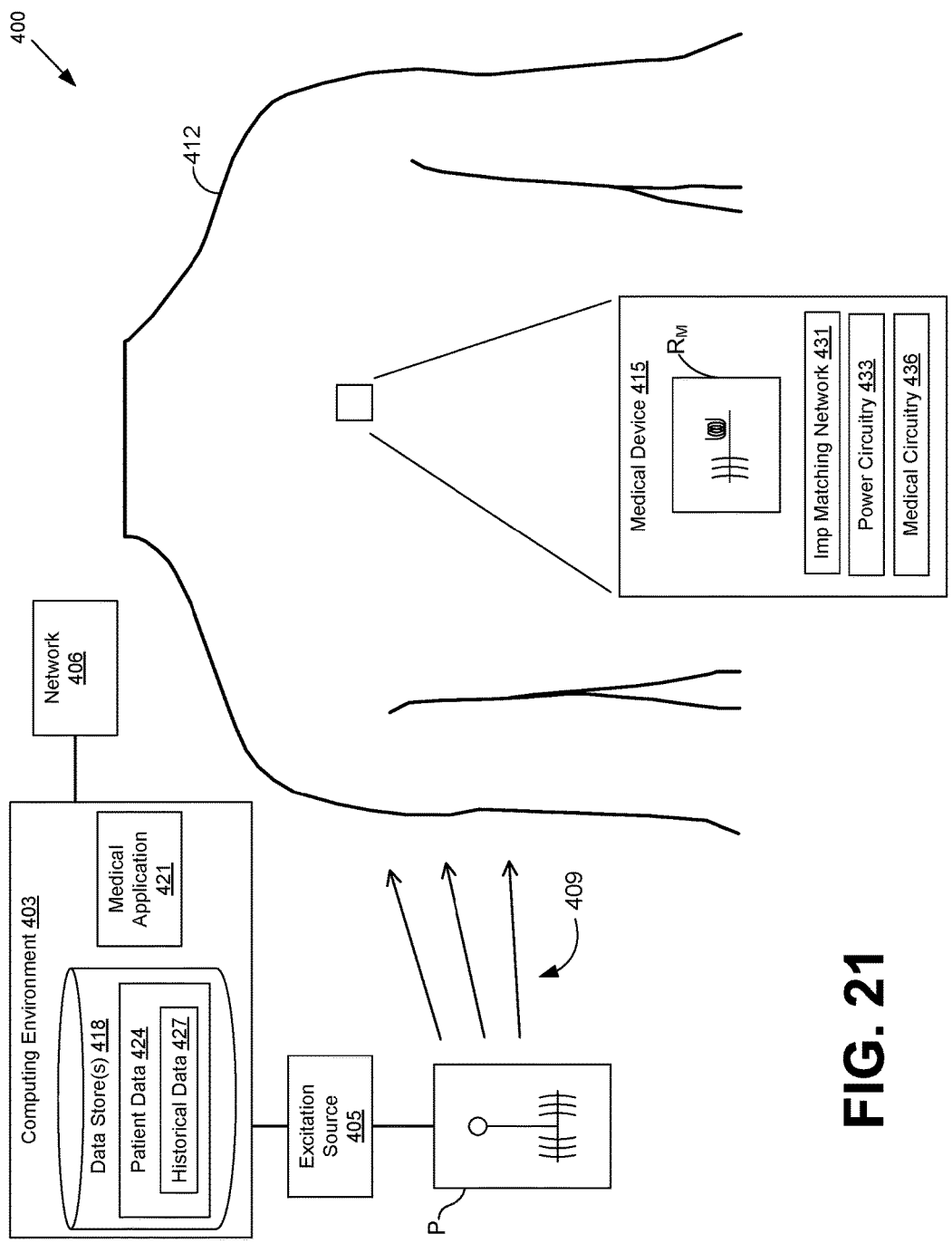
FIG. 21 is an illustration of a medical environment according to various embodiments of the present disclosure.

Turning to FIG. 21, shown is an example of a medical device implanted in a human body according to an embodiment. The medical environment 400 may include a computing environment 403, network 406, guided surface waveguide probe P, one or more guided surface waves 409, a human body 412, and a medical device 415. The computing environment may include a data store 418 and a medical application 421. The data store may include patient data 424 with historical data 427. The patient data 424 may include one or more patient records for one or more patients. The historical data 427 for each patient may include one or more measurements received from a medical device 415. The one or more measurements may be of one or more characteristics of the human body 412 for the patient. The one or more measurements may include repeated measurements of a single characteristic over time and/or repeated measurements of multiple characteristics over time. The computing environment 403 may be connected to network 406. The medical device 415 may communicate via a wireless connection to network 406. The medical application 421 may communicate with one or more medical devices 415 via the network 406.

According to one embodiment, the medical device 415 may include guided surface wave receive structure R, impedance matching network 431, power circuitry 433, and medical circuitry 436. The guided surface wave receive structure R is configured to receive a guided surface wave 409 transmitted by the guided surface waveguide probe P and generates an AC power signal. According to one embodiment, the guided surface wave receive structure R may comprise a guided surface wave receive structure $R_M$ comprising a coil that obtains energy from a magnetic field embodied in a guided surface wave as described above. In such case, the coil may be wrapped around various core materials that have a high mu so that a greater amount of magnetic flux can be channeled through such coils to provide a greater amount of energy at the output of the guided surface wave receive structure $R_M$. Such high mu materials may comprise mu-metals such as nickel-iron soft magnetic alloy having a relative permeability values of 80,000 to 100,000, or other appropriate metals. Alternatively, other guided surface wave receive structures R may be used. For example, it may be possible to use the guided surface wave receive structures $R_P$ and $R_R$ in situations where the medical device 415 resides outside a human body or where electrical leads are exposed outside the human body coupled to a medical device 415 implanted inside the human body.

The power circuitry 433 is coupled to the impedance matching network 431. The power circuitry 433 may include a power storage circuit configured to store the power signal. The power circuitry 433 may include AC-to-DC conversion circuitry such as a rectifier, such as a full wave rectifier and/or a half wave rectifier to convert an analog signal to a digital signal. The power storage circuit may include one or more batteries and/or one or more capacitors. The medical circuitry 436 may be coupled to the power circuitry 433, such as via an electrical connection.

The medical device 415 may be implanted in a human body, such as the human body 412. For example, a surgeon may cut open a patient and implant the medical device 415 within the human body 412 of the patient. The surgeon may connect leads to various parts of the body to monitor and/or stimulate the body, such as connecting one or more thin insulated wires through a vein into the heart to stimulate the heart. The surgeon may connect one or more stimulating elements to one or more parts of the human body 412 of the patient. The stimulating elements may include one or more of a chemical injector, a laser, an electrical wire, and/or an element that releases nanodevices and/or nanoparticles.

The surgeon may connect one or more sensing elements into the body of the patient. For example, the surgeon may implant a pressure sensing device within a vein, artery, or capillary to measure blood pressure and/or a frequency of heart beats. Other sensors may include electrical signal detectors and chemical sensors such as oxygen sensors, carbon dioxide sensors, glucose sensors, motion sensors, geospheres, accelerometers, GPS circuitry, a camera, and/or an x-ray device. The one or more sensors may be configured to detect a leak, such as a leak in a breast implant; detect a level of wear in a component of an artificial body part, such as an artificial hip, knee, or shoulder; detect a flow rate through one or more arteries, veins, and/or capillaries; and/or detect movement of repair or fusion hardware, such as a spine screw, rod, pin, plate, or artificial disc.

Alternatively, the medical device 415 may not be implanted into a human body. Rather, the medical device 415 may be positioned outside the body and may include electrical leads or other connections that enter the body from the medical device 415.

The guided surface waveguide probe P may output a guided surface wave 409 at a predefined field strength. According to one embodiment, the guided surface waveguide probe P is configured to transmit at a frequency low enough to propagate around the world. Alternatively, the guided surface waveguide probe P may transmit a guided surface wave at frequencies that propagate to lesser distances. In the event that a guided surface wave is transmitted globally, the resulting field strength will be lower due to geometric spreading at a relative equator with respect to the transmitting guided surface waveguide probe P, than the field strength at the location of the transmitter and at the antipode relative to the transmitting guided surface waveguide probe P. Also, if a guided surface waveguide probe P transmits to a lesser distance such as, for example, within the continental United States, the signal strength experienced at a distance from the guided surface waveguide probe P may not be as strong as the field near the guided surface waveguide probe P due to geometric spreading.

According to one embodiment, the guided surface waveguide probe P is configured to transmit a minimum power signal output in order to provide enough field strength to operate a medical device 415 at an area with the lowest signal strength, such as when the medical device 415 is located at and/or near the relative equator or on the edge of a transmission area. A measurement of field strength at one or more locations may be monitored by the medical application 421. The medical application 421 may increase and/or decrease the power signal strength output at guided surface waveguide probe P via an excitation source 405. The medical application 421 may increase the power signal strength until a measurement of field strength is received that exceeds or meets a preconfigured threshold, such as meeting a threshold field strength necessary to charge the medical device 415.

The medical application 421 transmits a power signal via excitation source 405. The excitation source 405 generates a voltage that is applied to the guided surface waveguide probe P. The guided surface waveguide probe P launches a guided surface wave 409 in response to the voltage being applied to the guided surface waveguide probe P. The medical device 415 receives energy from the guided surface wave 409 via guided surface wave receive structure $R_M$ and provides an AC power signal to the power circuitry 433 that stores energy in a battery and/or capacitor for use to power the medical circuitry 436. A battery and/or capacitor in power circuitry 433 may be charged by the power circuitry in cycles when a charge gets down below a predefined threshold.

Figure 22:
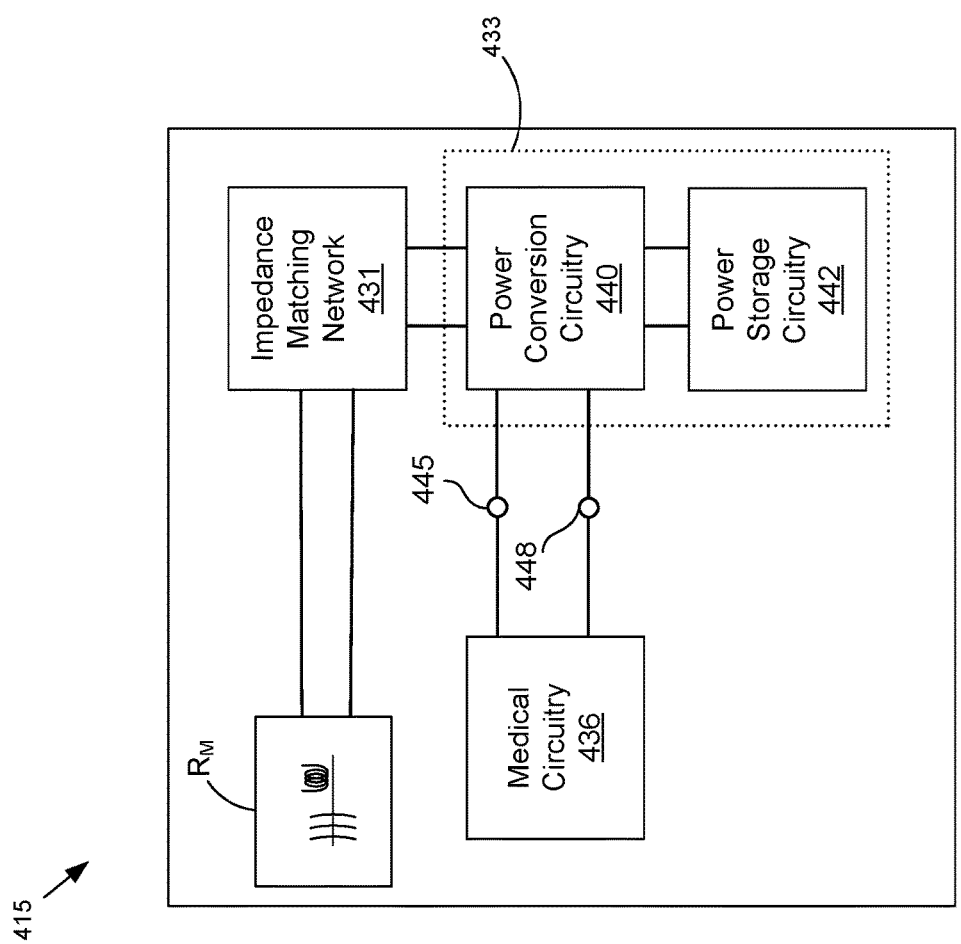
FIG. 22 depicts a medical device according to various embodiments of the present disclosure.

Turning to FIG. 22, shown is an example embodiment of medical device 415 according to various embodiments. The medical device 415 includes the guide surface wave receive structure $R_M$, impedance matching network 431, power circuitry 433, medical circuitry 436, terminals 445 and 448, and potentially other components. The power circuitry includes AC to DC conversion circuitry, power storage circuitry 442, and potentially other components. The guided surface wave receive structure $R_M$ is configured to receive a guided surface wave on a predefined frequency, such as guided surface wave 409 (FIG. 21). Alternatively, the guided surface wave receive structure $R_M$ and the impedance matching network 439 may be configured to receive guided surface waves at multiple different frequencies. To this end, the guided surface wave receive structure $R_M$ and corresponding impedance matching network 439 may represent a plurality of guided surface wave receive structures $R_M$ and corresponding impedance matching networks 439 that operate in parallel to receive power from guided surface waves at multiple different frequencies either one at a time or simultaneously. Alternatively, the physical parameters of the guided surface wave receive structure $R_M$ and/or the impedance matching network 439 may be adjusted from time to time to receive power from guided surface waves at various different frequencies.

The guided surface wave receiver structure $R_M$ is coupled to the power circuitry 433 through the impedance matching network 439. The power storage circuitry 442 includes terminals 445 and 448. The power circuitry generates a potential difference between terminals 445 and 448. For example, the power circuitry 433 receives a resulting output from the impedance matching network 439. According to one embodiment, the power circuitry 433 may convert that output into a DC power signal using power conversion circuitry 440, which may be provided to medical circuitry 436 and/or stored in power storage circuitry 442. In some embodiments, the power circuitry 443 trickle charges the power storage circuitry 442 continuously. In other embodiments, the power storage circuitry 442 is charged when the power level falls below a predefined threshold.

Figure 23:
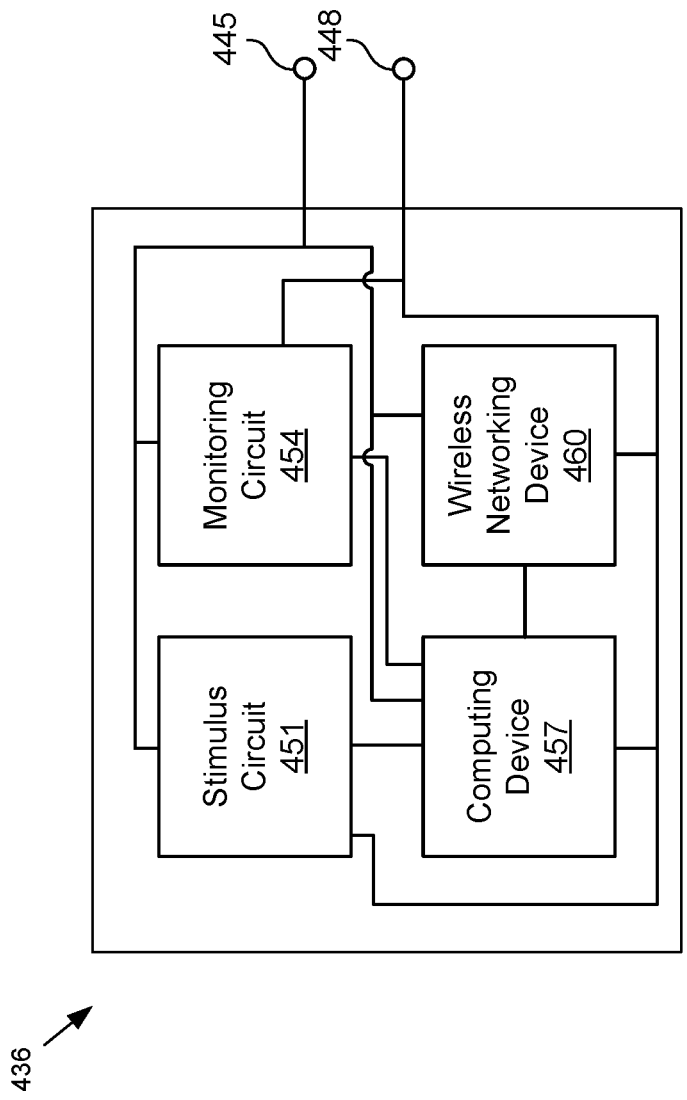
FIG. 23 depicts medical circuitry according to various embodiments of the present disclosure.

With reference to FIG. 23, shown is an example embodiment of medical circuitry 436 according to various embodiments. The medical circuitry 436 may be connected to power circuitry via terminals 445 and 448. Power may be supplied in the form of a DC voltage/current to medical circuitry 436 via the terminals 445 and 448. The medical circuitry 436 may include a stimulus circuit 451, a monitoring circuit 454, a computing device 457, and a wireless networking device 460. The stimulus circuit 451 is configured to provide a stimulus to a human body, such as a stimulus in the form of an electrical pulse, among other stimulus. The monitoring circuit 454 measures one or more characteristics of a human body 412 (FIG. 21). The characteristics may be one or more of a pulse, a blood pressure, a heartbeat frequency, a temperature, a respiration rate, an electric signal, a nerve impulse, a muscle twitch, a resistance value, a protein turnover level, a carbon dioxide level, an oxygen level, or other characteristic. The stimulus circuit 451 may be configured to activate in response to a change in a characteristic of the human body, such as a measurement from the monitoring circuit 454.

The computing device 457 may be coupled to the stimulus circuit 451, the monitoring circuit 454, and the wireless networking device 460. The computing device 457 may execute a medical device application, among other software or firmware applications stored in a memory associated with the computing device 457. The computing device 457 may include hardware configured to perform the operations described herein, such as an FPGA, among other known hardware. The computing device may receive one or more measurements from the monitoring circuit 454. The computing device 457 may be coupled to one or more elements within power circuitry 433 to monitor and/or manage power generation, storage, and output.

The computing device 457 may cause the stimulus circuit 451 to provide the stimulus to the human body 412. The stimulus may include one or more of an electrical stimulus to a peroneal nerve, an electrical stimulus to a heart chamber, an electrical stimulus to the surface of a stomach, an electrical stimulus to an auditory nerve, an auditory stimulus to an auditory nerve, a secretion of insulin, a secretion of one or more other substances, and/or some other stimulus. For example, the monitoring circuit 454 may measure a glucose level in a body and provide the glucose level to computing device 457. The computing device 457 may determine that the glucose level falls outside of a predefined range of acceptable values, and in response to it falling outside of the range, the computing device 457 may signal to stimulus circuit 451 to provide a stimulus to the human body 412. In response to receiving the signal, the stimulus circuit 451 may output a secretion of medicine, such as insulin.

The computing device 457 may process the one or more characteristics of the human body to calculate more complex measurements. For example, the computing device 457 may calculate a bezometabolic rate by first determining that a person is sleeping based on one or more of a heartbeat frequency, a respiration rate, and a blood pressure, and then monitoring oxygen and carbon dioxide levels in the body during a period of sleep. As another example, a $VO_2$ max value may be calculated by the computing device 457 based on first determining that a person is in a state of aerobic activity and then monitoring oxygen and carbon dioxide levels in the body.

Figure 24:
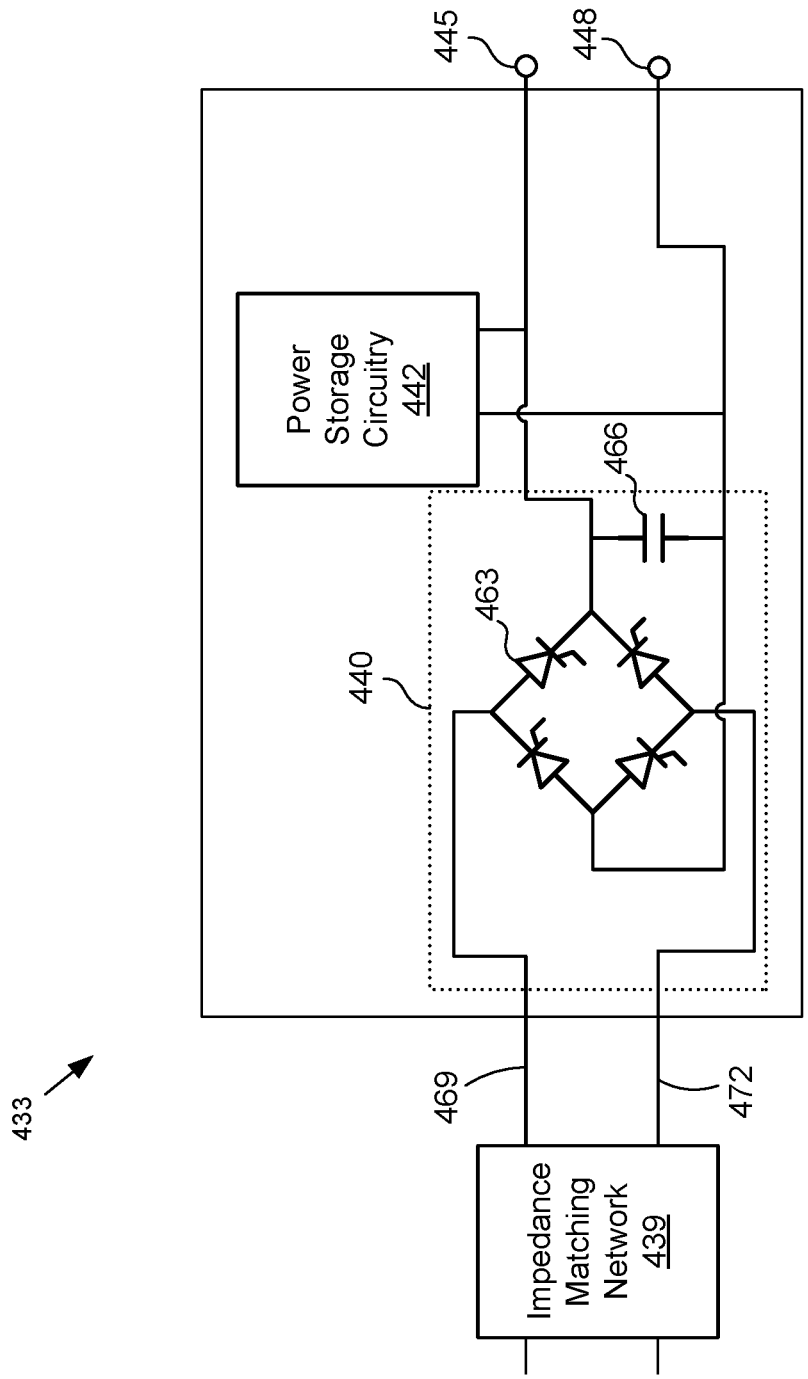
FIG. 24 depicts power circuitry according to various embodiments of the present disclosure.

With reference to FIG. 24, shown is an example embodiment of power circuitry 433 according to various embodiments. The power circuitry 433 includes a power conversion circuit 440 that may comprise, for example, a full wave rectifier 463 and smoothing capacitor 466, a power storage circuit 442, a positive input 469, a negative input 472, a positive output 445, and a negative output 448. The impedance matching network 439 is electrically coupled to the guided surface wave receive structure $R_M$. The impedance matching network 439 is configured reduce a reflection of the power signal and to provide for maximum power transfer at the frequency of operation as can be appreciated. The impedance matching network 439 may be the same as any impedance matching network described above. According to one embodiment, the power circuitry 433 (and medical circuitry 436 coupled thereto) is experienced as a load at an excitation source 405 (FIG. 21).

The power circuitry 433 is configured to convert an AC signal into a DC signal by way of AC-to-DC converter circuitry. For example, the power circuitry 433 receives an AC signal across positive input 469 and negative input 472 from the impedance matching network 439. The full wave rectifier 463 rectifies the AC signal to generate a DC signal. The smoothing capacitor 466 flattens the signal into a steady DC signal. Other rectifying circuits may be used, such as a half wave rectifier, a silicon controlled rectifier (SCR), a selenium and copper oxide rectifier, and/or silicon and germanium diodes, among other rectifiers as may be appreciated. In addition, other components such as a DC choke may be used to further stabilize the DC voltage. The output of the rectifying circuit 463 may be output directly to medical circuitry 436 (FIG. 21) or may be stored in power storage circuit 442. Power storage circuit 442 may output the stored power to the medical circuit 436 as needed.

The monitoring circuitry 454 (FIG. 23) may monitor a power level of power storage circuit 442. The computing device 457 may receive the power level from monitoring circuitry 454 and process the power level of power storage circuit 442. The computing device 457 may identify that a power level fails to meet a critical threshold of battery power in the power storage circuit 442 and generate a warning. The critical threshold may include a series of increasing critical thresholds. For example a series of critical thresholds may exist at one or more of 40% power level, 20% power level, 10% power level, 5% power level, 3% power level, 1% power level, or other power level.

According to one embodiment, the medical device 415 is configured to communicate with a reporting device via a wire lead extending outside the body. In this embodiment, the reporting device generates a warning, such as an audible warning. In yet another embodiment, the medical device 415 is not implanted in the body, but rather attached on the outside, such as an insulin pump.

The warning for each of the levels may increase in urgency as the power storage circuit 442 decreases in power level. The warning may be one or more of an audible noise, a physical pulse, and/or an electronic notification, such as an email or a text message. For example, the computing device 457 may transmit an email notifying that the power storage circuit has a power level below 40%, but may submit an electric pulse into the body to cause a muscle to twitch when the power level falls below 5%. Causing a muscle to twitch may be a startling event for a person, but a risk associated with a power level for medical device 415 falling below a critical threshold may outweigh startling the person.

Figure 27:
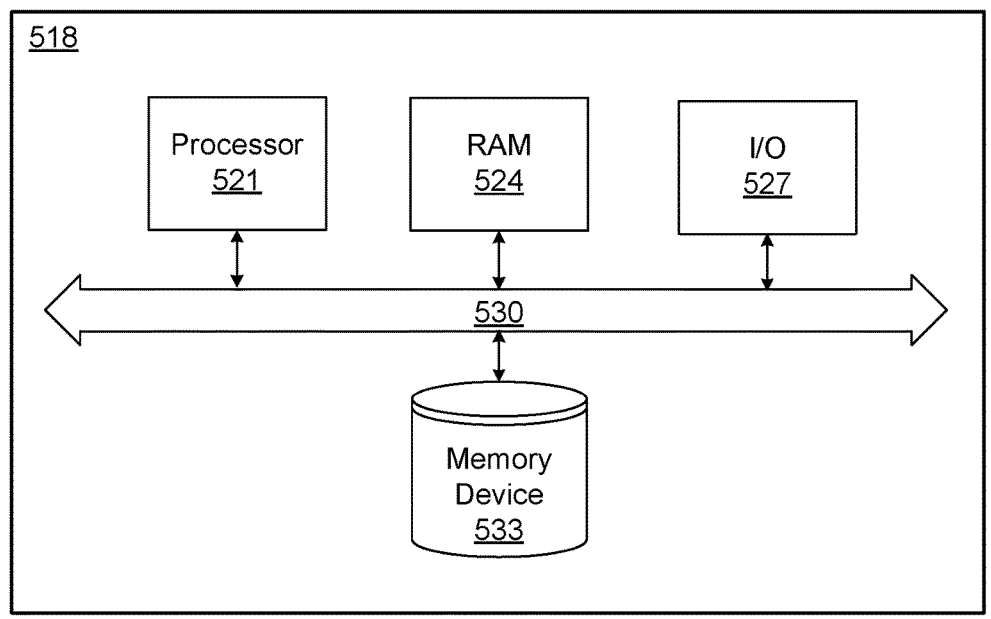
FIG. 27 is a schematic block diagram that provides one example illustration of a computing environment employed in the medical environment of FIG. 21 and the computing device employed in the medical circuitry of FIG. 23 according to various embodiments of the present disclosure.

The computing device 457 may also store the power level associated with a time of measurement in a memory device associated with the computing device 457, such as memory devices 524 and 533 (FIG. 27). The computing device 457 may transmit the power level to a remote server for processing and storage, such as computing environment 403 (FIG. 21). The computing device 457 may store a history of the power levels in the memory device until a syncing event occurs. The computing device 457 may verify the power level history has been transferred to the remote server. The computing device 457 may clear the history from the memory device in response to verifying the power level history was transferred successfully. The computing device 457 and/or remote server may process a history of power levels for a medical device 415 to determine an estimated life for the power storage circuitry 442. The ability for power storage circuitry 442 to store power may deteriorate over time and require the medical device 415 be extracted and the power storage circuitry 442 be replaced. For example, a battery and/or capacitor may deteriorate over time.

Figure 25:
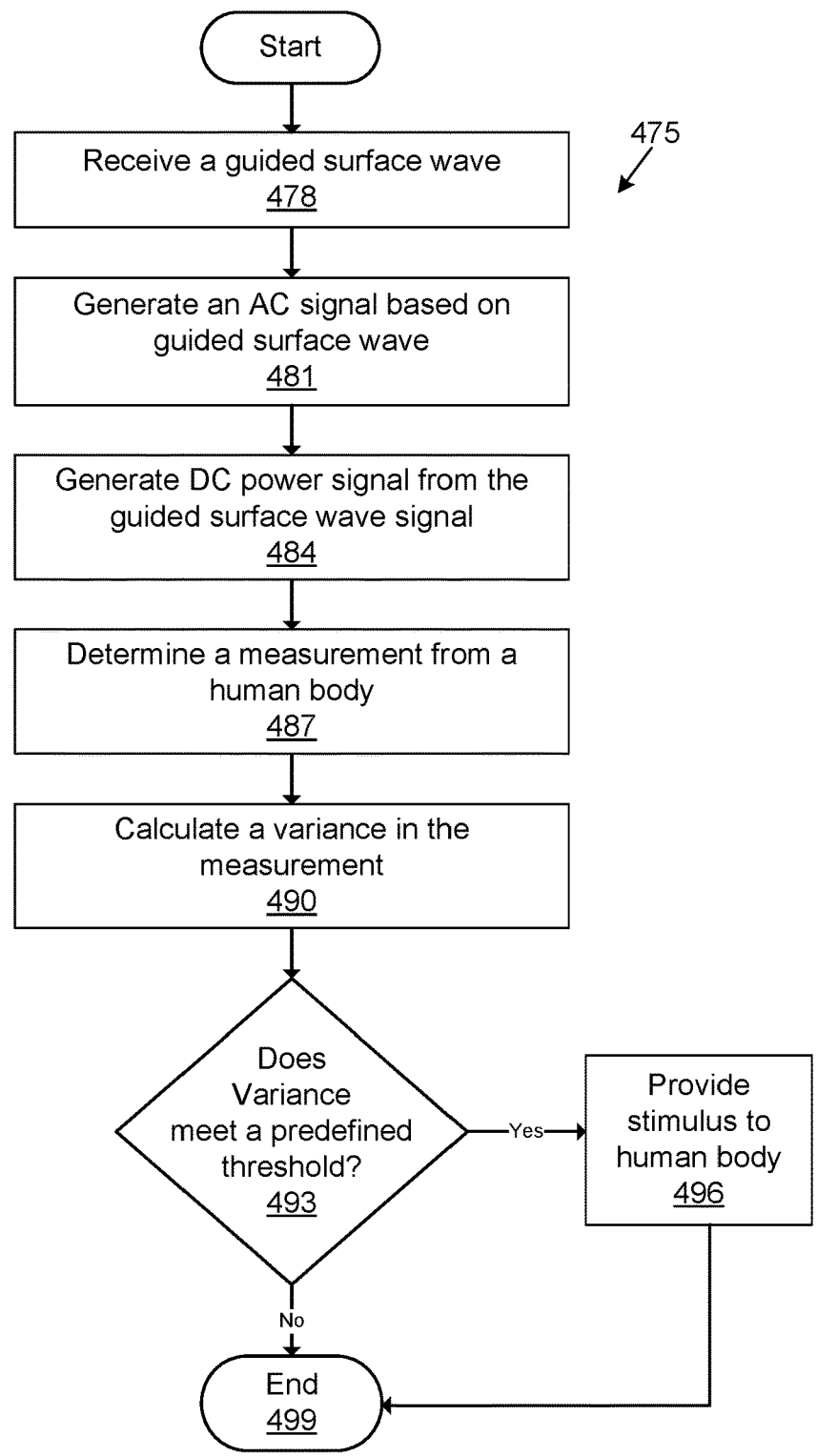
FIG. 25 is a flowchart illustrating one example of functionality implemented as portions of logic in a medical device of FIG. 21 according to various embodiments of the present disclosure.

Referring next to FIG. 25, shown is a flowchart of a medical stimulus process 475 that provides one example of the operation of a portion of the medical device 415 according to various embodiments. It is understood that the flowchart of FIG. 25 provides merely an example of the many different types of functional and/or physical arrangements that may be employed to implement the operation of the portion of the medical device 415 as described herein. As an alternative, the flowchart of FIG. 25 may be viewed as depicting an example of steps of a method implemented in the medical device 415 (FIG. 21) according to one or more embodiments.

At box 478, the medical stimulus process 475 includes receiving energy from a guided surface wave transmitted by a guided surface waveguide probe P. For example, the medical device 415 receives energy from a guided surface wave 409 (FIG. 21) by way of guided surface wave receive structure $R_M$ (FIG. 21). At box 481, the medical stimulus process 475 includes generating a power signal based on the received guided surface wave. For example, the guided surface wave receive structure $R_M$ outputs a power signal to the power circuitry 433 (FIG. 21) through the impedance matching circuitry 439. At box 484, the medical stimulus process 475 includes generating a power signal from the AC signal obtained from the guided surface wave receive structure $R_M$. For example, the power circuitry 433 may generate a DC power signal from the AC power signal generated by the guided surface wave receive structure $R_M$. The DC power signal may be used to power the medical device 415 in real time or by storing the generated power signal in a power storage device, such as the power storage circuitry 442 (FIG. 22). The power storage circuitry 442 may provide power stored from the power signal to the medical device 415.

At box 487, the medical stimulus process 475 includes determining a measurement from a human body. For example, monitoring circuit 454 (FIG. 23) of medical device 415 may obtain one or more measurements from a human body 412 (FIG. 21) via one or more sensing elements. The monitoring circuit 454 may include the one or more sensing elements and/or the one or more sensing elements may be separate elements. The monitoring circuit 454 may transmit the one or more measurements to the computing device 457 (FIG. 23). The measurements may be transmitted via a messaging protocol implemented in both the monitoring circuit 454 and computing device 457. The measurements may be transmitted by one or more outputs of monitoring circuit 454 being connected to one or more General Purpose Input/Output ("GPIO") lines of computing device 457. The output may be an analog signal and require an Analog-to-Digital converter circuit between the GPIO line of the computing device 457 and monitoring circuit 454. Each of the one or more outputs of the monitoring circuit 454 may correspond to a different measurement from a different sensing element. A single output of the monitoring circuit 454 may send more than one measurement from more than one sensing elements.

At box 490, the medical stimulus process 475 includes calculating a variance in the measurement. For example, the computing device 457 may process one or more measurements from the monitoring circuit 454 and one or more historical measurements stored in a memory device associated with the computing device 457 to determine a variance in one or more measurements. The variance may be a statistical measure. For example, the computing device 457 may compute an average value for one of the measurements over a history and calculate a standard deviation of the current measurement from the average value. The computing device 457 may perform a regression analysis on the history of measurements in memory, determine a predicted value of the current measurement based on the regression analysis, and determine a variance between the predicted value and the current measurement. For example, the regression analysis may identify a history of a blood pressure spike of 20% after eating at 5:00 PM, but determine a large variance if a measurement at 5:00 PM shows an increase of 50%, whereas an increase of only 20% would have no variance.

At box 493 the medical stimulus process 475 includes determining whether the variance meets a predefined threshold. For example, computing device 457 may compare a variance, such as the variance calculated in box 490, to determine whether the variance meets a predefined threshold. The predefined threshold may be stored in a memory device associated with the computing device 457. The predefined threshold may be modified, updated, or changed based in part on one or more characteristics of the human body the medical device 415 is implanted into. For example, the computing device 457 may store measurements of the effect of a dosage of insulin on the level of glucose in the body adjust a threshold for injecting insulin based in part on the effect. The effect of the dosage may change over time based in part on an increased resistance of the body to insulin, and thus the threshold may be changed over time by the computing device 457. A remote server, such as computing environment 403 (FIG. 21), may transmit a message via a network, such as network 406 (FIG. 21), to the medical device 415 instructing the computing device 457 to adjust the threshold stored in memory. If the threshold is met (e.g. Yes), the medical stimulus process 475 proceeds to box 496. If the threshold is not met (e.g. No), the medical stimulus process 475 proceeds to box 499.

At box 496, the medical stimulus process 475 includes providing a stimulus to the human body. For example, the computing device 457 may transmit an indication to a stimulus circuit 451 (FIG. 23) to cause the stimulus circuit 451 to provide or output a stimulus. For example, the computing device 457 may raise and/or lower a GPIO line connected to the stimulus circuit 451 to indicate that a stimulus should be provided. The computing device 457 may need to transmit a message to stimulus circuit 451 with parameters describing characteristics of the stimulus to be output. The stimulus circuit 451 may respond with a message confirming the instructions and the stimulus circuit 451 may require an acknowledgement from the computing device 457 before applying the stimulus. The communication between the stimulus circuit 451 and the computing device 457 may be encrypted. The stimulus circuit 451 provides the stimulus in response to receiving the indication from the computing device 457.

Figure 26:
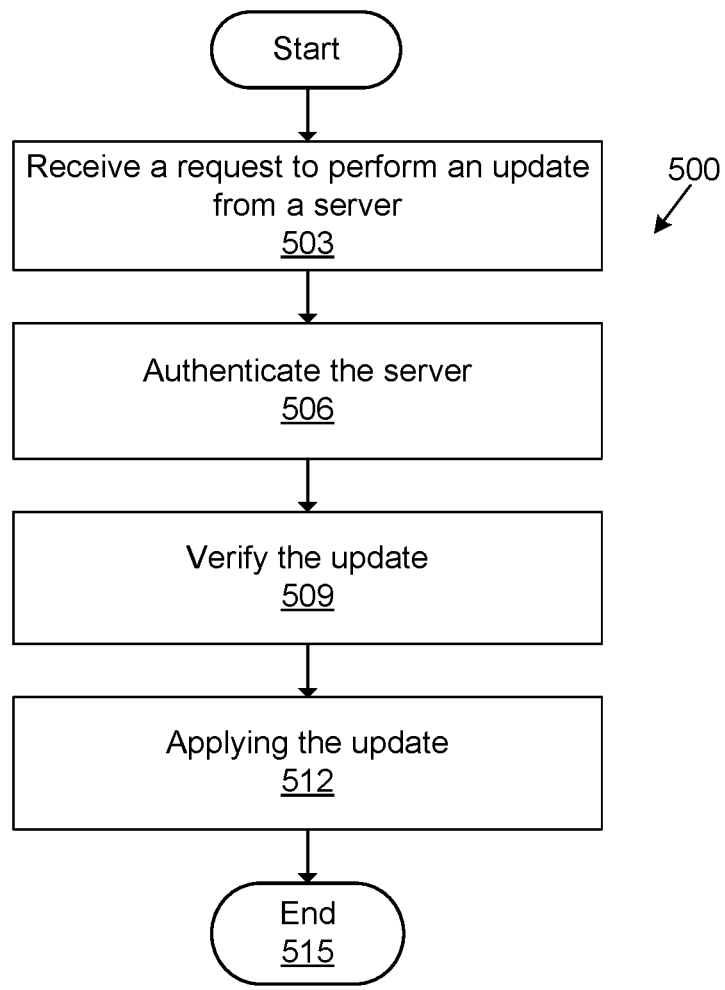
FIG. 26 is a flowchart illustrating one example of functionality implemented as portions of logic in a medical device of FIG. 21 according to various embodiments of the present disclosure.

Referring next to FIG. 26, shown is a flowchart of an update process 500 that provides one example of the operation of a portion of the medical device 415 according to various embodiments. It is understood that the flowchart of FIG. 26 provides merely an example of the many different types of functional arrangements that may be employed to implement the operation of the portion of the medical device 415 as described herein. As an alternative, the flowchart of FIG. 26 may be viewed as depicting an example of steps of a method implemented in the medical device 415 (FIG. 21) according to one or more embodiments.

At box 503, the update process 500 includes receiving a request to perform an update from a server. For example, the medical application 421 (FIG. 21) of computing environment 403 (FIG. 21) may transmit a message via network 406 (FIG. 21) to medical device 415. The request may be a request for the medical device 415 to transmit a history of measurements to the medical application 421 from a memory device associated with the computing device 457 (FIG. 23). The request may be to update or modify one or more thresholds for providing a stimulus including data describing the new or modified thresholds. The request may be a request to update software or firmware associated with the computing device 457. For example, the medical application 421 may request that the computing device 457 update firmware and set thresholds, for example, for a specific patient prior to installing the device and/or in an existing patient when updates become necessary or desirable.

At box 506, the update process 500 includes authenticating the server. For example, the computing device 457 may authenticate the medical application 421 prior to responding to any requests. The authentication may be based in part on one or more of a security credential, a digital signature, and/or a biometric feedback. The medical device 415 may be programmed prior to being implanted with a trusted security key known only to a doctor of the patient. The patient may be asked to specify security credentials to the doctor prior to the implant and those security credentials may be preloaded into the medical device 415.

The patient may authenticate the server based in part on flexing a muscle in a predefined manner, such as repeatedly flexing a chest muscle 3 times sequentially and a bicep two times. The computing device 457 may transmit a series of required biometric feedback steps required to authenticate the request to the medical application 421. The medical application 421 may render a user interface instructing the patient to perform the steps in order to validate the server. The biometric feedback may include pressing a button on the medical device 415 through the skin of the patient.

The wireless networking device 460 (FIG. 23) may be configured to communicate only within a preconfigured range, such as by using Near Field Communication (NFC). The wireless networking device 460 may limit a range that a wireless transmitter of network 406 must be within in order to communicate with the computing device 457. For example, the wireless networking device 460 may be an NFC transceiver that only transmits within a 1 foot radius of the medical device 415.

At box 509, the update process 500 includes verifying the update. For example, the computing device 457 may verify a hash of an update received from medical application 421. The computing device 457 may calculate a signature for a software update downloaded from the medical application 421, such as an MD5, checksum, and/or CRC. The signature may be compared to a signature embedded within the software update. The computing device 457 may transmit the signature to the medical application 421, and the medical application 421 may acknowledge the signature and/or instruct the computing device 457 to apply the software update, download the software update again, discard the software update, and/or cancel the software update. The computing device 457 may transmit a confirmation message and receive an acknowledgement prior to applying an update to one or more thresholds. The computing device 457 may verify the request by transmitting a history of measurements to the medical application 421 when requested.

At box 512, the update process 500 includes applying the update. For example, the computing device 457 may store an update to a memory device. The computing device 457 may store a software update to a memory device associated with the computing device 457. The computing device 457 may execute the stored software update in response to successfully saving the update. The computing device 457 may store an update to one or more thresholds to memory locations preconfigured to store the one or more thresholds. For example, the computing device 457 may store a new variance threshold in a specific address in a Non-Volatile Ram (NV Ram) assigned to the variance threshold. The specific address may be an address used when determining if a threshold is exceeded, such as in box 493 (FIG. 25).

With reference to FIG. 27, shown is a schematic block diagram of the computing environment 403 (FIG. 21) and/or computing device 457 (FIG. 27) according to an embodiment of the present disclosure. The computing environment 403 and/or computing device 457 include one or more computing devices 518. Each computing device 518 includes at least one processor circuit, for example, having a processor 521 and a memory 524/533, both of which are coupled to a local interface 530. To this end, each computing device 518 may comprise, for example, at least one server computer or like device. The local interface 530 may comprise, for example, a data bus with an accompanying address/control bus or other bus structure as can be appreciated. The computing device 518 may include one or more I/O 527, such as a serial port, a network port, a GPIO, a USB port, among other known I/O.

Stored in the memory 524/533 are both data and several components that are executable by the processor 521. In particular, stored in the memory 524/533 and executable by the processor 521 are one or more application including an application executed in computing device 457 and the medical application 421, and potentially other applications. Also stored in the memory 524/533 may be a data store 418 (FIG. 21) and other data. In addition, an operating system may be stored in the memory 524/533 and executable by the processor 521.

It is understood that there may be other applications that are stored in the memory 524/533 and are executable by the processor 521 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 524/533 and are executable by the processor 521. In this respect, the term "executable" means a program file that is in a form that can ultimately be run by the processor 521. Examples of executable programs may be, for example, a compiled program that can be translated into machine code in a format that can be loaded into a random access portion of the memory 524/533 and run by the processor 521, source code that may be expressed in proper format such as object code that is capable of being loaded into a random access portion of the memory 524/533 and executed by the processor 521, or source code that may be interpreted by another executable program to generate instructions in a random access portion of the memory 524/533 to be executed by the processor 521, etc. An executable program may be stored in any portion or component of the memory 524/533 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 524/533 is defined herein as including both volatile and nonvolatile memory and data storage components. Volatile components are those that do not retain data values upon loss of power. Nonvolatile components are those that retain data upon a loss of power. Thus, the memory 524/533 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 521 may represent multiple processors 521 and/or multiple processor cores and the memory 524/533 may represent multiple memories 524/533 that operate in parallel processing circuits, respectively. In such a case, the local interface 530 may be an appropriate network that facilitates communication between any two of the multiple processors 521, between any processor 521 and any of the memories 524/533, or between any two of the memories 524/533, etc. The local interface 530 may comprise additional systems designed to coordinate this communication, including, for example, performing load balancing. The processor 521 may be of electrical or of some other available construction.

Although an application executed in computing device 457 and the medical application 421, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowcharts of FIGS. 25 and 26 show the functionality and operation of an implementation of portions of the application executed in computing device 457 and/or functionality of the hardware in computing device 457. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 521 in a computer system or other system. The machine code may be converted from the source code, etc. If embodied in hardware, each block may represent a circuit or a number of interconnected circuits to implement the specified logical function(s).

Although the flowcharts of FIGS. 25 and 26 show a specific order of execution, it is understood that the order of execution may differ from that which is depicted. For example, the order of execution of two or more blocks may be scrambled relative to the order shown. Also, two or more blocks shown in succession in FIGS. 25 and 26 may be executed concurrently or with partial concurrence. Further, in some embodiments, one or more of the blocks shown in FIGS. 25 and 26 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including an application executed in computing device 457 and the medical application 421, that comprises software or code can be embodied in any non-transitory computer-readable medium for use by or in connection with an instruction execution system such as, for example, a processor 521 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including an application executed in computing device 457 and the medical application 421, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 518 or in multiple computing devices 518 in the same computing environment 403 and/or computing device 457. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims. In addition, all optional and preferred features and modifications of the described embodiments and dependent claims are usable in all aspects of the disclosure taught herein. Furthermore, the individual features of the dependent claims, as well as all optional and preferred features and modifications of the described embodiments are combinable and interchangeable with one another.

Therefore, the following is claimed:

1. An apparatus, comprising:
   a guided surface wave receive structure configured to receive a guided surface wave traveling along a terrestrial medium, the guided surface wave being generated by an electromagnetic field excited by a guided surface waveguide probe, the electromagnetic field synthesizing a wave front incident at a complex Brewster angle of incidence of the terrestrial medium;
   a power circuit electrically coupled to the guided surface wave receive structure, the power circuit generating a power signal from an alternating current signal generated by the guided surface wave receive structure; and
   a medical circuit configured to receive electrical energy from the power signal generated by the power circuit, the medical circuit comprising a monitoring circuit configured to receive measure a characteristic of a human body.

2. The apparatus of claim 1, wherein the medical circuit comprises a stimulus circuit configured to provide a stimulus to the human body.

3. The apparatus of claim 2, wherein the stimulus circuit is configured to stimulate the human body in response to a change in value of at least one measurement by the monitoring circuit.

4. The apparatus of claim 2, wherein the medical circuit further comprises a computing device coupled to the stimulus circuit and the monitoring circuit, the computing device configured to at least:
   receive at least one measurement from the monitoring circuit; and
   cause the stimulus circuit to provide the stimulus to the human body.

5. The apparatus of claim 2, wherein the stimulus comprises at least one of: an electrical stimulus to a peroneal nerve, an electrical stimulus to a heart chamber, an electrical stimulus to a surface of a stomach, an electrical stimulus to an auditory nerve, or a secretion of insulin.

6. The apparatus of claim 2, wherein the medical circuit comprises a computing device connected to the power circuit.

7. The apparatus of claim 6, wherein the computing device is configured to obtain a measurement from a sensing device and initiate the stimulus to the human body based at least in part on the measurement.

8. The apparatus of claim 2, wherein the guided surface wave receive structure further comprises a coil wrapped around a high-mu material.

9. The apparatus of claim 1, wherein the apparatus is configured to be implanted in the human body.

10. The apparatus of claim 1, wherein the power circuit comprises a power storage circuit configured to store the power signal.

11. The apparatus of claim 1, wherein the monitoring circuit is configured to measure at least one of: a pulse, a blood pressure, a temperature, a respiration rate, an electric signal, a nerve impulse, a muscle twitch, a resistance value, a protein turnover level, or an oxygen level.

12. The apparatus of claim 1, wherein the guided surface wave receive structure is coupled to the power circuit through an impedance matching network, the impedance matching network configured to minimize a reflection of the alternating current signal back to the guided surface wave receive structure.

13. A system comprising:
   a guided surface waveguide probe configured to generate an electromagnetic field when excited by an excitation source, wherein the electromagnetic field synthesizes a wave front incident at a complex Brewster angle of incidence of a terrestrial medium to generate a guided surface wave that travels across the terrestrial medium; and
   a medical device comprising a guided surface wave receive structure, the guided surface wave receive structure being configured to generate an alternating current (AC) signal from the guided surface wave for the medical device, the medical device being experienced as a load at the excitation source coupled to the guided surface waveguide probe.

14. The system of claim 13, wherein the medical device is configured to stimulate a human body in response to a change in value of at least one measurement by the medical device.

15. The system of claim 13, wherein the medical device further comprises a rectifying circuit configured to convert the AC signal into a direct current (DC) signal.

16. The system of claim 15, wherein the rectifying circuit comprises a full-wave bridge rectifier.

17. The system of claim 15, wherein the medical device further comprises a power storage circuit configured to store energy from the DC signal in a storage device and provide stored power to the medical device from the storage device, the storage device comprising at least one of a battery or a capacity.

18. The system of claim 13, wherein the guided surface wave receive structure comprises a magnetic coil.

19. A method comprising:
generating an alternating current (AC) signal, via at least one guided wave receive structure, from at least one guided surface wave generated by an electromagnetic field excited by a guided surface waveguide probe, the electromagnetic field synthesizing a wave front incident at a complex Brewster angle of incidence of a terrestrial medium;
supplying, via power circuitry, electrical energy generated embodied in the AC signal to medical circuitry comprising a monitoring circuit and a stimulus circuit;
determining, via the monitoring circuit, at least one measurement from a human body; and
providing, via the stimulus circuit, a stimulus to the human body.

20. The method of claim 19, wherein the medical circuitry further comprises at least one computing device and the method further comprises:
receiving, via the at least one computing device, the at least one measurement from the monitoring circuit; and
causing, via the at least one computing device, the stimulus circuit to provide the stimulus.

21. The method of claim 20, further comprising:
receiving, via the at least one computing device, at least one preconfigured impulse; and
transmitting, via the at least one computing device, information describing at least one measurement from the monitoring circuit over a network connection.

22. The method of claim 20, further comprising:
receiving, via the at least one computing device, a request to modify at least one threshold for providing the stimulus;
modifying, via the at least one computing device, the at least one threshold based at least in part on the request to generate at least one modified threshold; and
causing, via the at least one computing device, the stimulus circuit to provide the stimulus based in part on the at least one modified threshold.

23. The method of claim 20, further comprising:
receiving, via the at least one computing device, a software package via a network connection, the software package including a hash of the software package;
verifying, via the at least one computing device, the software packaged based at least in part on the hash;
receiving, via the at least one computing device, a request to program the software package into a memory associated with the computing device;
storing, via the at least one computing device, the software package in the memory;
validating, via the at least one computing device, the software package was successfully stored; and
executing, via the at least one computing device, the software package.

24. The method of claim 20, further comprising:
receiving, via the at least one computing device, a request from an server via a network connection; and
authenticating, via the at least one computing device, the request based at least in part on at least one security credential.

* * * * *

UNITED STATES PATENT AND TRADEMARK OFFICE
CERTIFICATE OF CORRECTION

PATENT NO. : 10,230,270 B2
APPLICATION NO. : 15/239507
DATED : March 12, 2019
INVENTOR(S) : Corum et al.

Page 1 of 1

It is certified that error appears in the above-identified patent and that said Letters Patent is hereby corrected as shown below:

In the Specification

At Column 50, Line 10, delete "calculate a benzometabolic rate," and replace with --calculate a basal metabolic rate--

Signed and Sealed this
Seventeenth Day of September, 2019

Andrei Iancu
*Director of the United States Patent and Trademark Office*